United States Patent
Velzy et al.

(10) Patent No.: US 10,092,716 B2
(45) Date of Patent: Oct. 9, 2018

(54) FLOW GENERATOR

(71) Applicant: RESMED MOTOR TECHNOLOGIES INC., Chatsworth, CA (US)

(72) Inventors: Allan Freas Velzy, Burlingame, CA (US); Samuel Aziz Mebasser, Chatsworth, CA (US); Roman Vinokur, Woodland Hills, CA (US); Kevin Gene McCulloh, Simi Valley, CA (US); Michael David Bednar, Playa Del Ray, CA (US); Karl Yutaka Iwahashi, Granada Hills, CA (US); David Brent Sears, Woodland Hills, CA (US); Peter Jeffrey Thomas, Sylmar, CA (US); Yeu-chuan Hsia, Northridge, CA (US); Hiroshi Suzuki, Canyon Country, CA (US); Benjamin An Shing Chao, Jersey City, NJ (US)

(73) Assignee: ResMed Motor Technologies Inc., Chatsworth, CA (US)

( * ) Notice: Subject to any disclaimer, the term of this patent is extended or adjusted under 35 U.S.C. 154(b) by 487 days.

(21) Appl. No.: 14/382,694

(22) PCT Filed: Dec. 20, 2012

(86) PCT No.: PCT/US2012/070857
§ 371 (c)(1),
(2) Date: Sep. 3, 2014

(87) PCT Pub. No.: WO2013/133889
PCT Pub. Date: Sep. 12, 2013

(65) Prior Publication Data
US 2015/0023782 A1 Jan. 22, 2015

Related U.S. Application Data

(60) Provisional application No. 61/607,176, filed on Mar. 6, 2012.

(51) Int. Cl.
*F04D 29/40* (2006.01)
*A61M 16/00* (2006.01)
(Continued)

(52) U.S. Cl.
CPC .... *A61M 16/0066* (2013.01); *A61M 16/0069* (2014.02); *A61M 16/107* (2014.02);
(Continued)

(58) Field of Classification Search
CPC .............. A61M 16/066; A61M 16/069; A61M 16/107; A61M 16/0666; A61M 16/0683;
(Continued)

(56) References Cited

U.S. PATENT DOCUMENTS 4,568,243 A  2/1986  Schubert et al.
6,315,526 B1 11/2001 Jones
(Continued)

FOREIGN PATENT DOCUMENTS

CN  101008407  8/2007
CN  101296722  10/2008
(Continued)

OTHER PUBLICATIONS

Extended European Search Report issued in corresponding European Application No. 12 87 0338.6 dated Oct. 12, 2015.
(Continued)

*Primary Examiner* — Dominick L Plakkoottam
*Assistant Examiner* — Philip Stimpert
(74) *Attorney, Agent, or Firm* — Nixon & Vanderhye P.C.

(57) ABSTRACT

A flow generator includes a housing, a blower structured to generate a flow of pressurized breathable air, and a suspension device to support the blower within the housing and provide a pressure seal between low and high pressure sides of the blower. The suspension device includes a bellows-like portion provided along the perimeter of the blower to absorb
(Continued)

shock applied at least radially to the blower and one or more cones provided along upper and/or lower sides of the blower to absorb shock applied at least axially to the blower.

27 Claims, 87 Drawing Sheets

(51) Int. Cl.
*A61M 16/10* (2006.01)
*F04D 29/66* (2006.01)
*A61M 16/06* (2006.01)
*A61M 16/08* (2006.01)

(52) U.S. Cl.
CPC ......... *F04D 29/403* (2013.01); *F04D 29/667* (2013.01); *A61M 16/0666* (2013.01); *A61M 16/0683* (2013.01); *A61M 16/0875* (2013.01); *A61M 2205/42* (2013.01); *A61M 2205/502* (2013.01)

(58) Field of Classification Search
CPC .............. A61M 16/42; A61M 2205/42; A61M 2205/502
USPC ......... 415/213.1, 214.1, 215.1, 119; 267/141
See application file for complete search history.

(56) References Cited

U.S. PATENT DOCUMENTS

| | | | |
|---|---|---|---|
| 6,474,960 B1 | 11/2002 | Hansmann | |
| 6,644,311 B1 | 11/2003 | Truitt et al. | |
| 6,837,260 B1 | 1/2005 | Kuehn | |
| 7,975,688 B1 | 7/2011 | Truitt | |
| 8,016,275 B2* | 9/2011 | Ting | F16F 1/3732 165/69 |
| 8,839,786 B2 | 9/2014 | Heidmann et al. | |
| 2005/0103339 A1 | 5/2005 | Daly et al. | |
| 2006/0250039 A1* | 11/2006 | Yamamoto | F04D 25/082 310/90 |
| 2007/0169781 A1* | 7/2007 | Tang | A61M 16/00 128/206.21 |
| 2007/0247009 A1 | 10/2007 | Hoffman et al. | |
| 2008/0072900 A1* | 3/2008 | Kenyon | A61M 16/0051 128/204.18 |
| 2009/0007912 A1* | 1/2009 | Lindell | A61M 16/10 128/204.18 |
| 2009/0044808 A1 | 2/2009 | Guney et al. | |
| 2009/0191054 A1* | 7/2009 | Winkler | F04D 29/526 415/215.1 |
| 2009/0301485 A1 | 12/2009 | Kenyon et al. | |
| 2010/0132708 A1 | 6/2010 | Martin et al. | |
| 2010/0307498 A1 | 12/2010 | Jones et al. | |
| 2012/0057959 A1 | 3/2012 | Hodgson et al. | |
| 2014/0069432 A1 | 3/2014 | Mebasser et al. | |
| 2014/0137870 A1 | 5/2014 | Barlow et al. | |
| 2014/0352696 A1 | 12/2014 | Heidmann et al. | |

FOREIGN PATENT DOCUMENTS

| | | |
|---|---|---|
| CN | 101553667 | 10/2009 |
| EP | 2 000 675 | 12/2008 |
| JP | 2008-303876 A | 12/2008 |
| JP | 2010-508009 A | 3/2010 |
| JP | 58-72700 A | 10/2014 |
| WO | 2007/024955 A2 | 3/2007 |
| WO | 2007/087599 A1 | 8/2007 |
| WO | WO 2008/051534 | 5/2008 |
| WO | WO 2010/028121 | 3/2010 |
| WO | PCT/AU2010/001031 | 8/2010 |
| WO | PCT/AU2010/001106 | 8/2010 |
| WO | 2011/006206 A1 | 1/2011 |
| WO | WO 2012/145358 | 10/2012 |
| WO | WO 2012/174602 | 12/2012 |
| WO | WO 2013/133889 A1 | 9/2013 |

OTHER PUBLICATIONS

Further Examination Report issued in corresponding New Zealand Application No. 629662 dated Apr. 4, 2016.
International Preliminary Report on Patentability dated Sep. 9, 2014 including a Written Opinion of the International Searching Authority dated Apr. 22, 2013 issued in corresponding PCT Application No. PCT/US2012/070857.
First Examination Report issued in corresponding New Zealand Application No. 718377 dated Apr. 4, 2016.
Office Action dated Oct. 7, 2016 issued in Japanese Application No. 2014-560906 with English translation (10 pages).
First Examination Report issued in corresponding New Zealand Application No. 629662 dated Apr. 20, 2015.
International Search Report issued in PCT Appln. No. PCT/US2012/070857 dated Apr. 22, 2013.
U.S. Appl. No. 61/607,176, filed Mar. 2012, Velzy et al.
U.S. Appl. No. 61/457,273, filed Feb. 2011, Davidson et al.
U.S. Appl. No. 61/457,858, filed Jun. 2011, Davidson et al.
U.S. Appl. No. 61/457,526, filed Apr. 2011, Lane et al.
U.S. Appl. No. 61/630,920, filed Dec. 2011, Lane et al.
First Office Action issued in corresponding Chinese Application No. 201280073027.2 dated Dec. 4, 2015, with English translation thereof.
Office Action dated Jun. 12, 2017 issued in Japanese Application No. 2014-560906 with English translation (12 pages).
Further Examination Report dated Sep. 4, 2017 issued in New Zealand Application No. 718377 (2 pages).
First Examination Report dated Oct. 9, 2017 issued in New Zealand Application No. 735666 (2 pages).
Extended European Search Report dated Mar. 5, 2018 issued in European Application No. 17193282.5 (11 pages).

\* cited by examiner

2427

FLOW GENERATOR

CROSS-REFERENCE TO APPLICATION

This application is the U.S. national phase of International Application No. PCT/US2012/070857 filed 20 Dec. 2012 which designated the U.S. and claims the benefit of U.S. Provisional Application No. 61/607,176, filed Mar. 6, 2012, the entire contents of each of which are incorporated herein by reference in their entirety.

FIELD OF TECHNOLOGY

The present technology relates to a flow generator for generating a flow of breathable gas to be delivered to a patient. In an example, the flow generator may be used in a positive airway pressure (PAP) device used for the delivery of respiratory therapy to a patient. Examples of such therapies are Continuous Positive Airway Pressure (CPAP) treatment, Non-Invasive Positive Pressure Ventilation (NIPPV), Variable Positive Airway Pressure (VPAP), and Bi-Level Positive Airway Pressure. The therapy is used for treatment of various respiratory conditions including Sleep Disordered Breathing (SDB) and more particularly Obstructive Sleep Apnea (OSA).

BACKGROUND OF TECHNOLOGY

Flow generators are used to generate a flow of breathable gas for treatment of various respiratory conditions. The flow generator may be configured to be connected to a patient interface, for example a mask, to deliver the flow of breathable gas to the patient's airways.

A blower is provided in the flow generator to generate the flow of breathable gas. A blower may comprise a motor comprising a rotating part including, for example, a shaft having an impeller(s) mounted thereon, and a non-rotating part. The operation of the motor may generate noise and vibration. As the therapy may be delivered to the patient during sleep, the generation of noise and vibration may reduce the effectiveness of the therapy.

SUMMARY OF TECHNOLOGY

An aspect of the disclosed technology relates to a flow generator including a suspension device structured to support a blower within the housing and provide a pressure seal between low and high pressure sides of the blower.

Another aspect of the disclosed technology relates to a flow generator including a suspension device structured to support a blower within the housing to allow operation of the flow generator in any orientation.

Another aspect of the disclosed technology relates to a flow generator including a suspension device structured to support a blower within the housing and absorb shock applied radially and axially to the blower. In an example, the suspension device may include a bellows-like portion provided along the perimeter of the blower to absorb shock applied at least radially to the blower and one or more cones provided along upper and/or lower sides of the blower to absorb shock applied at least axially to the blower.

Another aspect of the disclosed technology relates to a flow generator including a housing having a blower chamber to support a blower, the blower chamber including at least one opening to allow air to enter the blower on the low pressure side thereof and at least one opening to allow air to exit the blower chamber on the high pressure side thereof.

Another aspect of the disclosed technology relates to a flow generator including a housing structured to receive and support a PCB outside the air flow path.

Another aspect of the disclosed technology relates to a flow generator including a housing having one or more ribs along the perimeter of its side wall, e.g., to reduce turbulence/high frequency noise during air intake, for aesthetics, to hide or otherwise blend an air filter at the inlet.

Another aspect of the disclosed technology relates to a flow generator in which the power cord connection includes a lead wire extending directly from the PCB to outside the housing.

Another aspect of the disclosed technology relates to a flow generator including a housing having an interface button movably mounted, e.g., by a living hinge, to the top cover of the housing to allow the button to activate a switch provided to the PCB enclosed within the top cover.

Another aspect of the disclosed technology relates to a flow generator including a blower having magnet wire directly connected to the PCB, e.g., rather than using a lead wire.

Another aspect of the disclosed technology relates to a flow generator including an air flow path providing cross-sectional areas of a suitable size to prevent turbulent airflow.

Another aspect of the disclosed technology relates to a flow generator including an air flow path providing reflective surfaces to reduce noise.

Another aspect of the disclosed technology relates to a flow generator including a removable air filter at the inlet to filter incoming air.

Another aspect of the disclosed technology relates to a flow generator including one or more foam pieces along the air flow path to direct air and provide sound absorption.

Another aspect of the disclosed technology relates to a flow generator including a housing, a blower structured to generate a flow of pressurized breathable air, and a suspension device to support the blower within the housing and provide a pressure seal between low and high pressure sides of the blower. The suspension device may include a bellows-like portion provided along the perimeter of the blower to absorb shock applied at least radially to the blower and one or more cones provided along upper and/or lower sides of the blower to absorb shock applied at least axially to the blower.

Another aspect of the disclosed technology relates to a flow generator including a housing including an inlet and an outlet and a blower provided to the housing and structured to generate a flow of pressurized breathable air. The housing includes an air flow path from the inlet to the outlet providing cross-sectional areas along its length of a sufficient size to prevent turbulent airflow. The cross-sectional areas may be of sufficient size to provide a flow rate less than 10 m/s, e.g., a flow rate of about 5-6 m/s.

Another aspect of the disclosed technology relates to a flow generator including a housing including an inlet and an outlet and a blower provided to the housing and structured to generate a flow of pressurized breathable air. The housing includes an air flow path from the inlet to the outlet providing one or more reflective surfaces along its length to reduce noise. The housing may include one or more air flow vanes including the reflective surfaces to provide a noise barrier for the blower and/or reflect noise from the blower so as to prevent noise emitted back through the inlet. The one or more air flow vanes may be provided adjacent the inlet to direct incoming air flow from the inlet.

Another aspect of the disclosed technology relates to a flow generator including a housing, a blower structured to generate a flow of pressurized breathable air, and a suspension device configured to, at least in part, support the blower within the housing to allow operation (e.g., for normal patient therapy) of the flow generator in any or substantially any orientation.

Another aspect of the disclosed technology relates to a flow generator including a housing including an inlet and an outlet, a blower provided to or within the housing and structured to generate a flow of pressurized breathable air, and an air filter cartridge, e.g., provided to the inlet, to filter air drawn into the housing by the blower. The air filter cartridge may include a cartridge body and a filter supported by the cartridge body. The cartridge body may include structure to at least partly direct airflow away from a blower inlet of the blower.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIGS. 23-1 to 23-7 show various views of a flow generator according to another example of the present technology;

FIGS. 24-1 and 24-2 show cross-sectional views of a flow generator including a suspension device according to another example of the present technology;

FIGS. 25-1 to 25-11 show various views of a flow generator according to another example of the present technology;

FIGS. 26-1 to 26-3 show various views of a flow generator according to another example of the present technology;

FIGS. 27-1 to 27-3 show various views of a flow generator according to another example of the present technology;

FIGS. 29-1 to 29-3 show various views of a flow generator according to another example of the present technology;

FIGS. 31-1 and 31-2 show various views of a flow generator according to another example of the present technology;

FIGS. 32-1 to 32-3 show various views of a flow generator according to another example of the present technology;

FIGS. 34-1 and 34-2 show various views of a flow generator according to another example of the present technology;

FIGS. 35-1 and 35-2 show various views of a flow generator according to another example of the present technology;

FIGS. 36-1 to 35-3 show various views of a flow generator according to another example of the present technology;

FIGS. 48-1 to 52-2 show interface buttons for a flow generator according to alternative examples of the present technology;

FIGS. 80-1 to 80-5 show a flow generator according to another example of the present technology;

FIGS. 81-1 to 81-5 show a flow generator according to another example of the present technology;

FIGS. 82-1 to 82-3 show a flow generator according to another example of the present technology;

FIGS. 83-1 to 83-3 show a flow generator according to another example of the present technology;

FIGS. 92-1 to 95 show air filter arrangements for a flow generator according to alternative examples of the present technology;

FIGS. 101-1 to 101-11 show various views of a flow generator according to an example of the present technology;

FIGS. 102-1 to 102-9 show various views of an air filter according to an example of the present technology;

FIGS. 103-1 to 103-3 show various views of an air filter arrangement for a flow generator according to an example of the present technology;

FIGS. 103-4 to 103-5 show perspective views of an air filter of the air filter arrangement shown in FIGS. 103-1 to 103-3.

DETAILED DESCRIPTION OF ILLUSTRATED EXAMPLES

Figure 1:
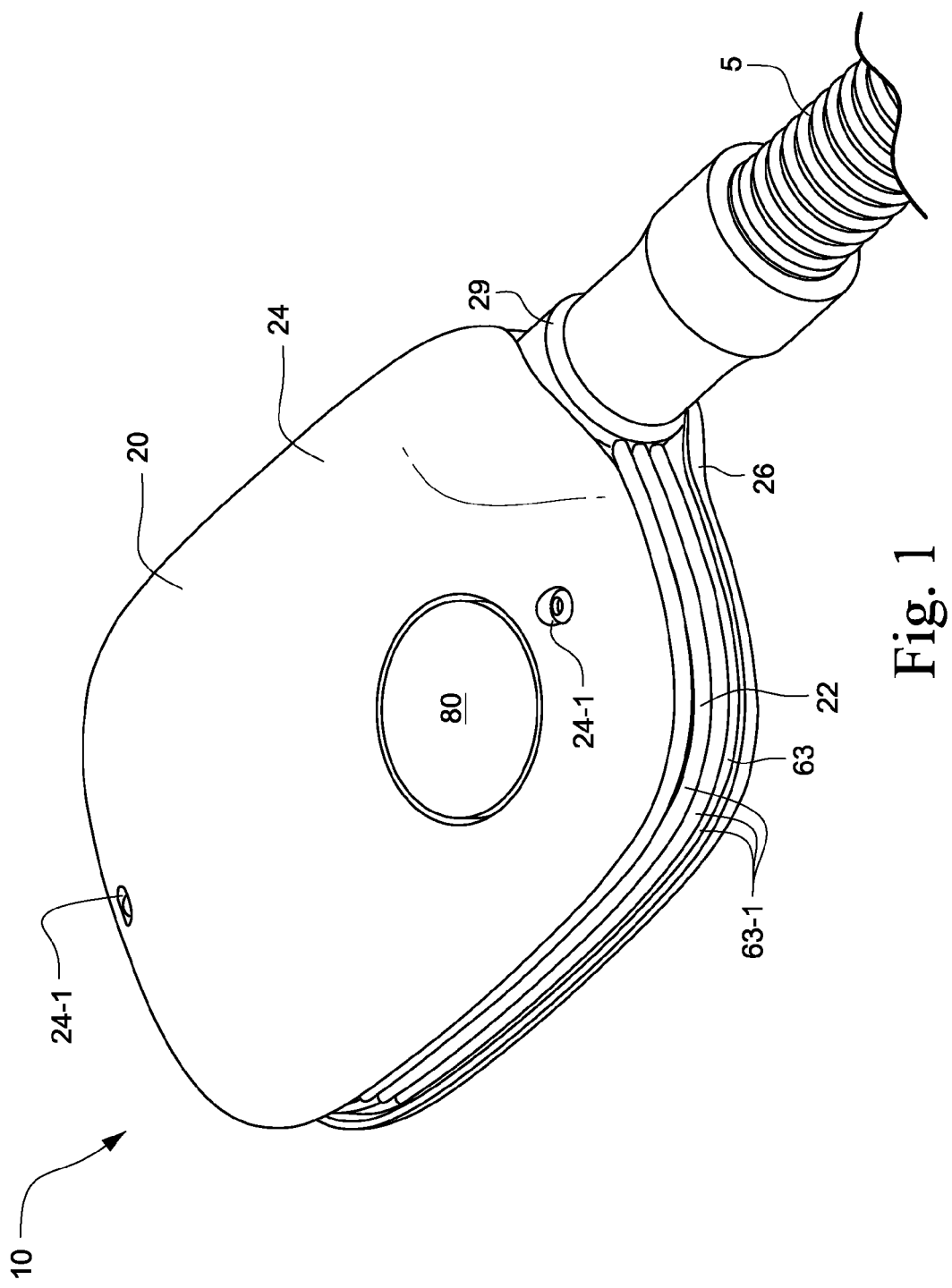
FIG. 1 is a top perspective view of a flow generator according to an example of the present technology.

The following description is provided in relation to several examples (most of which are illustrated, some of which may not) which may share common characteristics and features. It is to be understood that one or more features of any one example may be combinable with one or more features of the other examples. In addition, any single feature or combination of features in any example or examples may constitute patentable subject matter.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. PAP System

A PAP system typically includes a flow generator or PAP device (including a blower for generating air at positive pressure), an air delivery conduit (also referred to as a tube or tubing), and a patient interface (e.g., mask). In use, the flow generator generates a supply of pressurized air (e.g., 2-30 cm H₂O) that is delivered to the patient interface via the air delivery conduit. The patient interface or mask may have suitable configurations as is known in the art, e.g., full-face mask, nasal mask, oro-nasal mask, mouth mask, nozzles, nasal prongs, nasal pillows, cannula, etc. Also, headgear may be utilized to comfortably support the patient interface in a desired position on the patient's face.

Certain examples relate to PAP systems in which the flow generator is adapted to be worn on the patient's head, is built into or incorporated into the patient interface or mask, is wearable or carried by the patient, is portable, is reduced in size or combinations thereof. In certain examples, the PAP system may be of the type described in PCT Application Nos. PCT/AU2010/001031 and/or PCT/AU2010/001106, each of which is incorporated herein by reference in their entirety.

In another example, the PAP system may be of the wearable type described in U.S. Provisional Application Nos. 61/457,273, filed Feb. 16, 2011, and 61/457,858, filed Jun. 21, 2011, each of which is incorporated herein by reference in its entirety.

2. Flow Generator

FIGS. 1-22 illustrate a flow generator 10 according to an example of the present technology. As illustrated, the flow generator 10 includes a housing 20 that encloses and supports a blower 30 for generating a supply of pressurized air. Along with the blower 30, the housing encloses or otherwise supports other internal components, e.g., a suspension device 40, a printed circuit board (PCB) 50 for controlling the blower, and/or an air filter 70. The flow generator may include a power supply or preferably is coupled to an external power via a power cord.

2.1 Housing

The flow generator (FG) housing 20 includes a chassis or main housing 22, a first or top cover 24 provided to one side of the chassis, and a second or bottom cover 26 provided to the opposite side of the chassis. As illustrated, the FG housing 20 has a generally rectangular shape with preferably curved edges or corners and has a relatively low profile, i.e., the first or top cover 24 and the second or bottom cover 26 have relatively larger surface areas compared to each of the two side surfaces and the two end surfaces. However, the FG housing 20 may be formed in a variety of different shapes.

In an example, the chassis 22, top cover 24, and bottom cover 24 may be formed (e.g., molded) of a plastic material. However, it should be appreciated that other suitable materials are possible.

As illustrated, the chassis 22 and bottom cover 26 cooperate to define a blower chamber 25 adapted to receive and support the blower 30 within the FG housing 20 as described in more detail below. The blower chamber 25 includes at least one opening to allow air to enter the blower on the low pressure side thereof and at least one opening to allow air to exit the blower chamber 25 on the high pressure side thereof.

The blower 30 is configured to generate a flow of pressurized breathable air, e.g., in the range of about 2-30 cm H₂O. In an example, the blower 30 may be of the type described in U.S. Provisional Application Nos. 61/457,526, filed Apr. 18, 2011, and 61/630,920, filed Dec. 22, 2011, each of which is incorporated herein by reference in its entirety. However, it should be appreciated that the housing may be structured to receive and support other suitable blowers.

Air is drawn into the FG housing 20 by the blower 30 through an air flow inlet 27 (and air filter 70 at the air flow inlet 27) into an inlet chamber 33 and the supply of pressurized air exits the FG housing 20 through an air flow outlet 29. As described below, the blower 30 is supported within the blower chamber 25 by a suspension or support device 40 (e.g., constructed of a flexible elastomeric material such as silicone), which resiliently supports the blower and provides a seal (e.g., 360° seal) between the lower pressure side, inlet side or inlet 32 and the high pressure side, outlet side or outlet 34 of the blower 30 (see FIGS. 9 and 16). The blower chamber 25 retains the blower and suspension device 40 within the FG housing 20. In an example, the suspension device may be constructed of a flexible material that is able to flex, bend, compress, and/or expand but sufficiently stiff and resilient to maintain structural integrity during use.

Also, as shown in FIGS. 5-8, the chassis 22 and top cover 24 cooperate to receive and support the printed circuit board (PCB) 50. As illustrated, the PCB 50 is supported outside the air flow path so air flow does not flow over the electronics.

Low Profile

Figure 11:
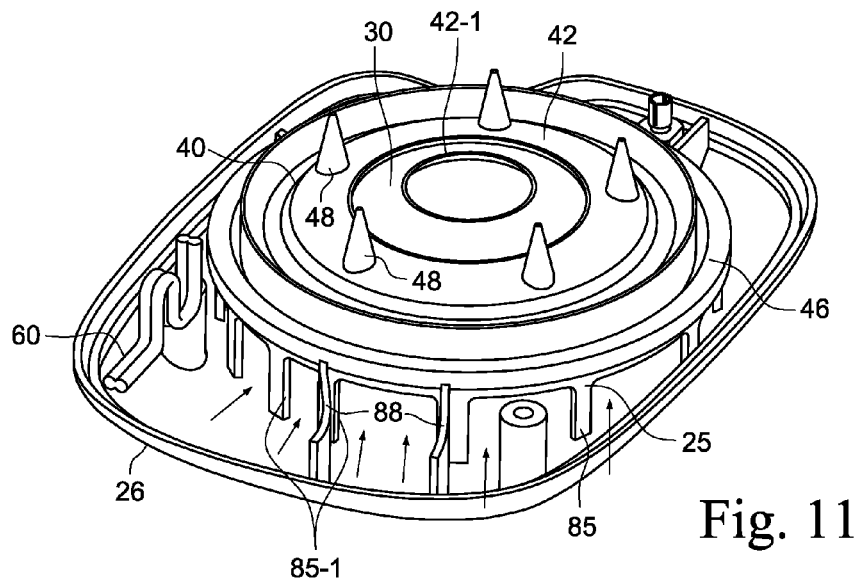
FIG. 11 is a perspective view of the bottom cover, blower, and suspension device of the flow generator of FIG. 1.
Figure 12:
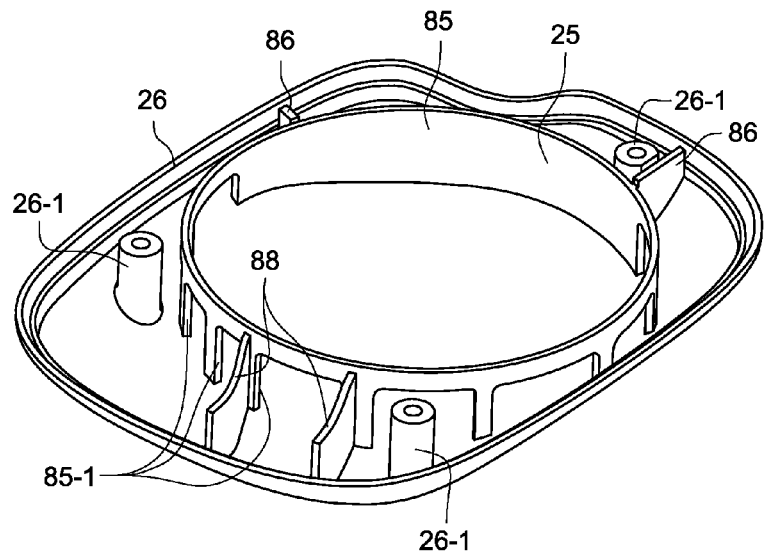
FIG. 12 is a perspective view of the bottom cover of the flow generator of FIG. 1.
Figure 13:
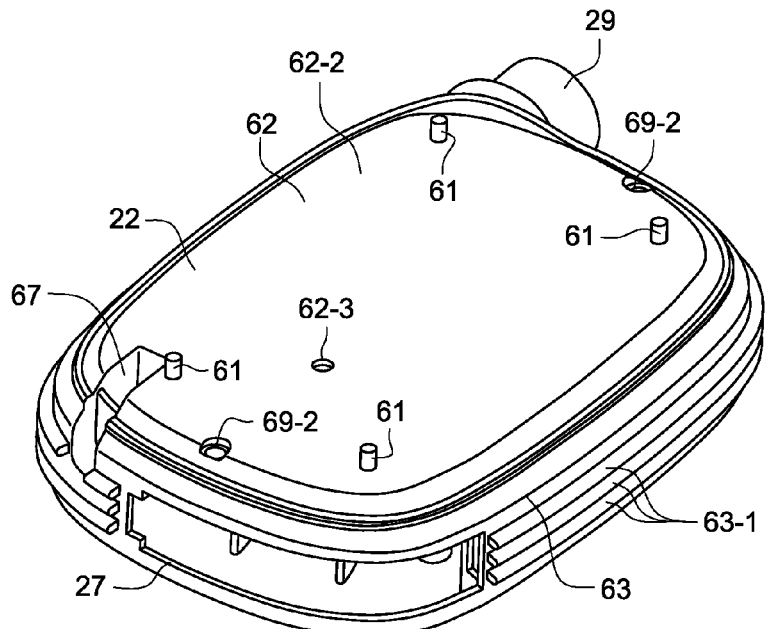
FIG. 13 is a perspective view of the chassis of the flow generator of FIG. 1.
Figures 1, 101:
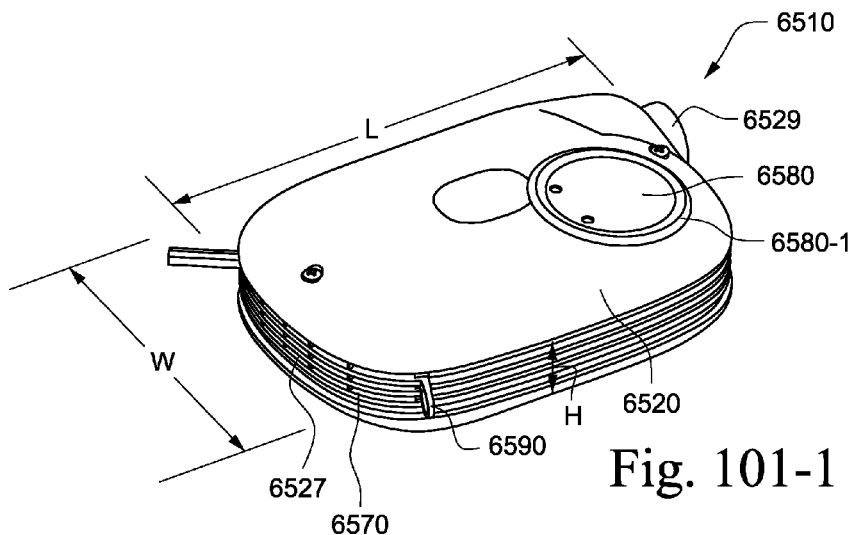
Figures 2, 101:
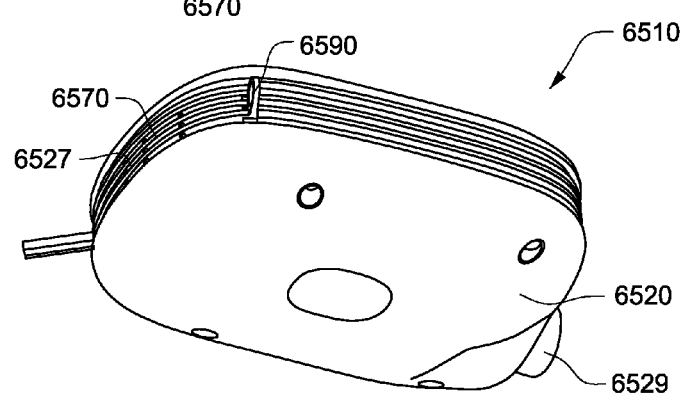
Figures 3, 101:
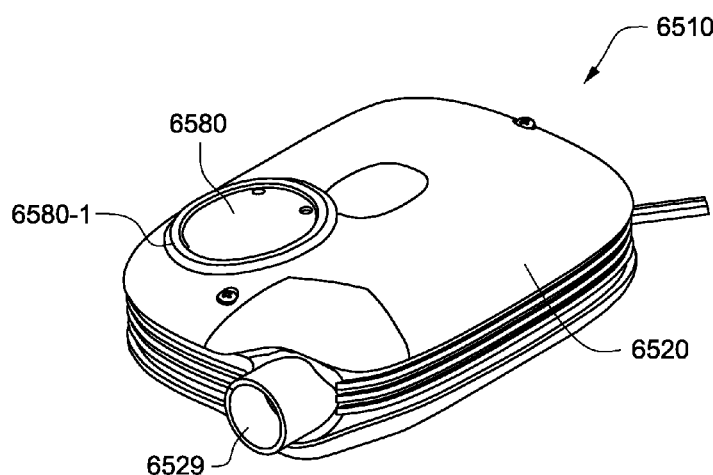
Figures 4, 101:
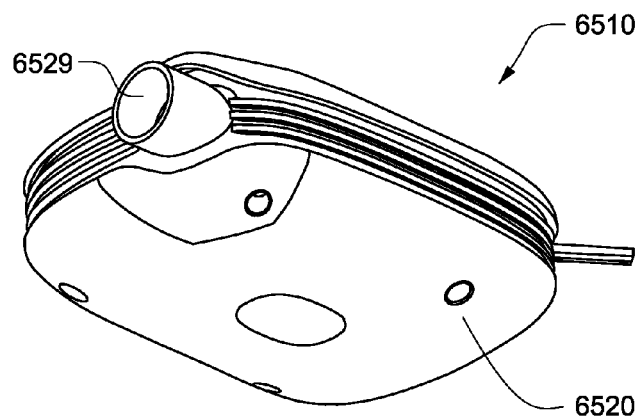
Figures 5, 101:
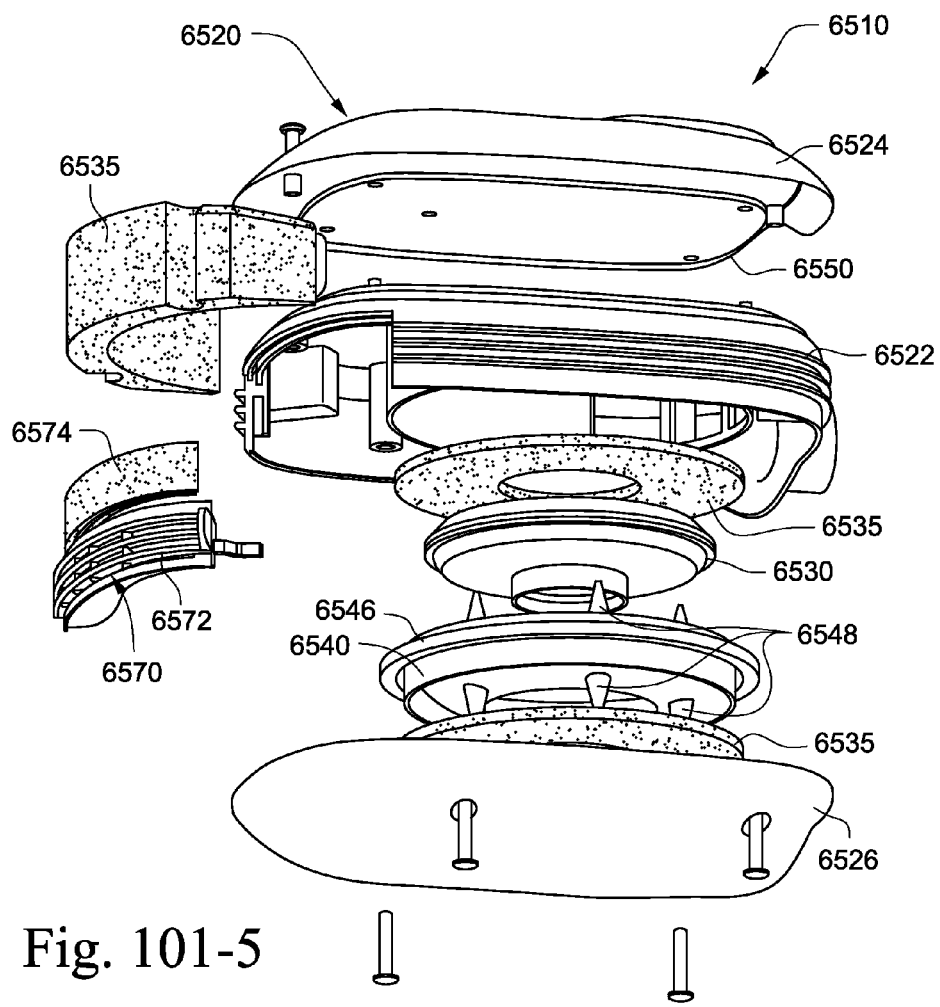
Figures 6, 101:
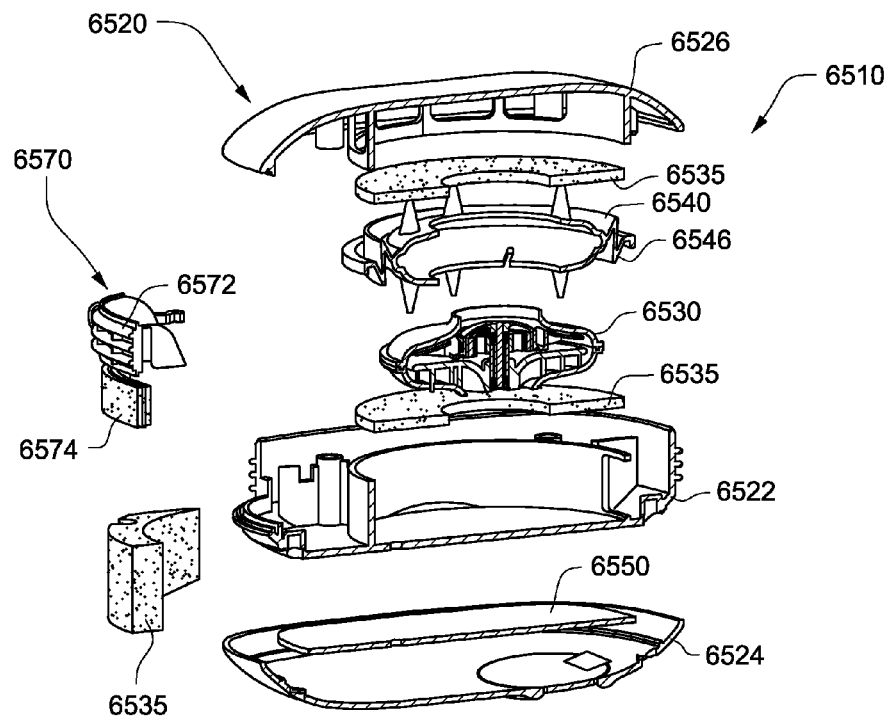
Figures 7, 101:
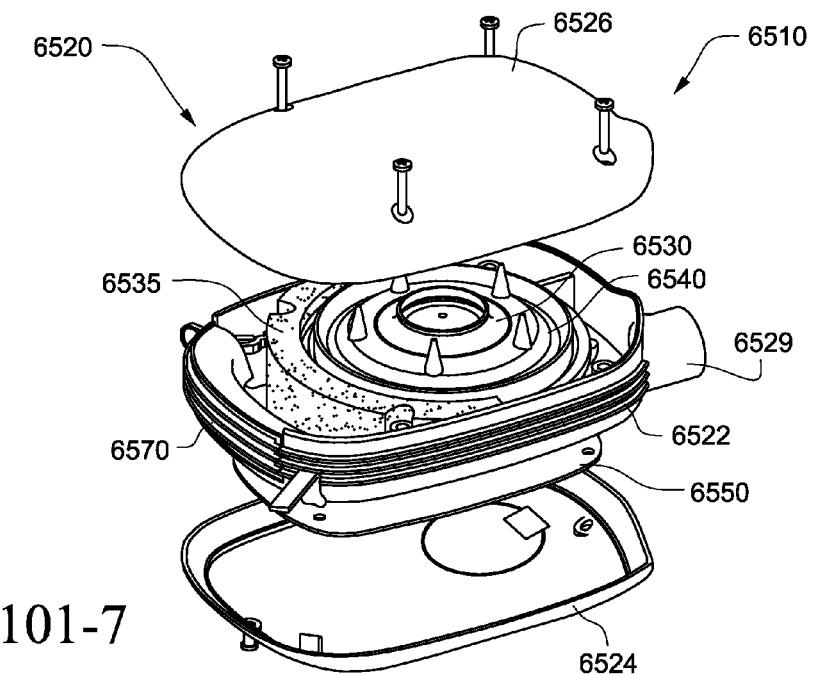
Figures 8, 101:
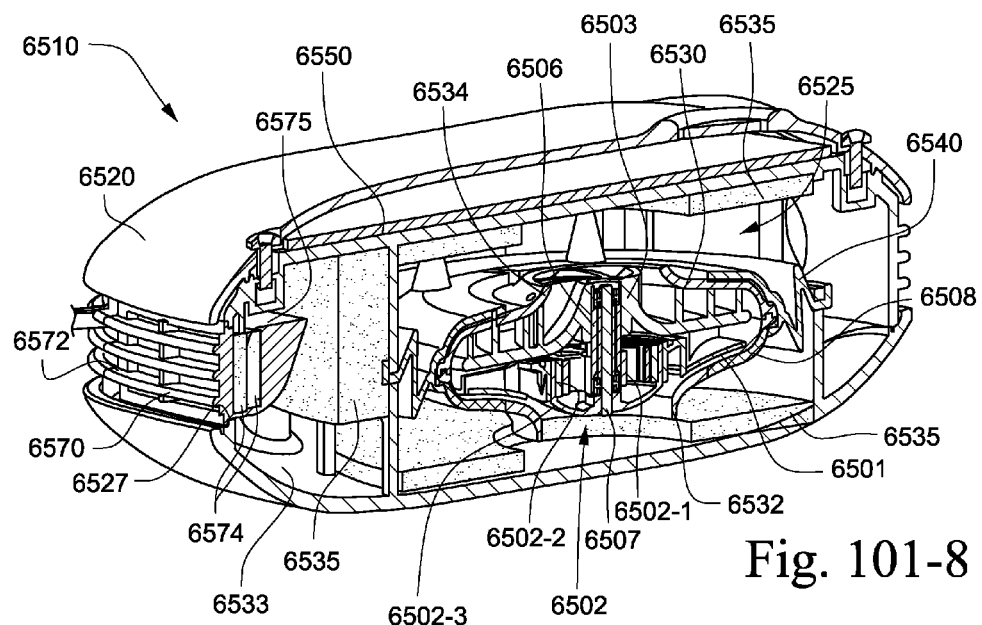
Figures 9, 101:
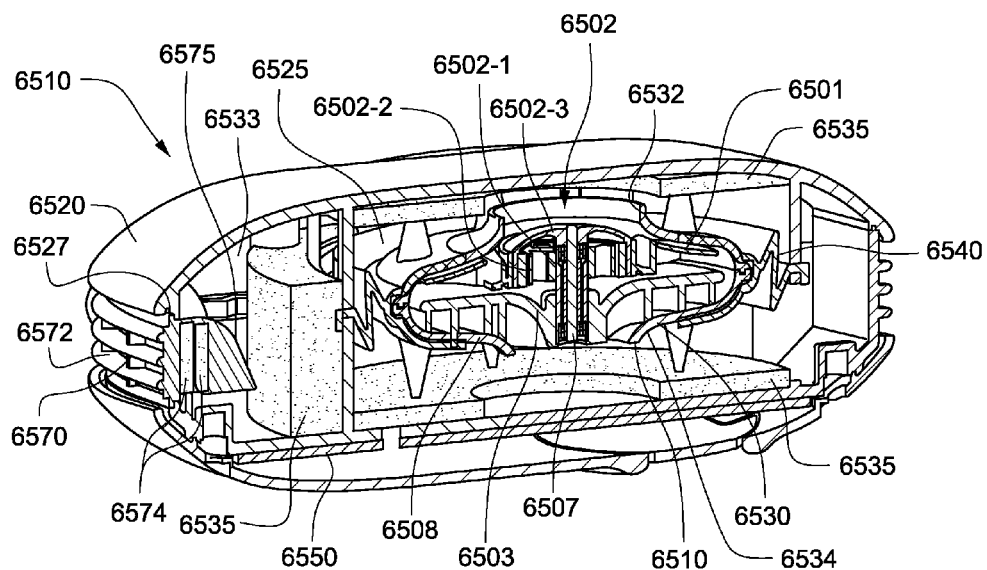
Figures 10, 101:
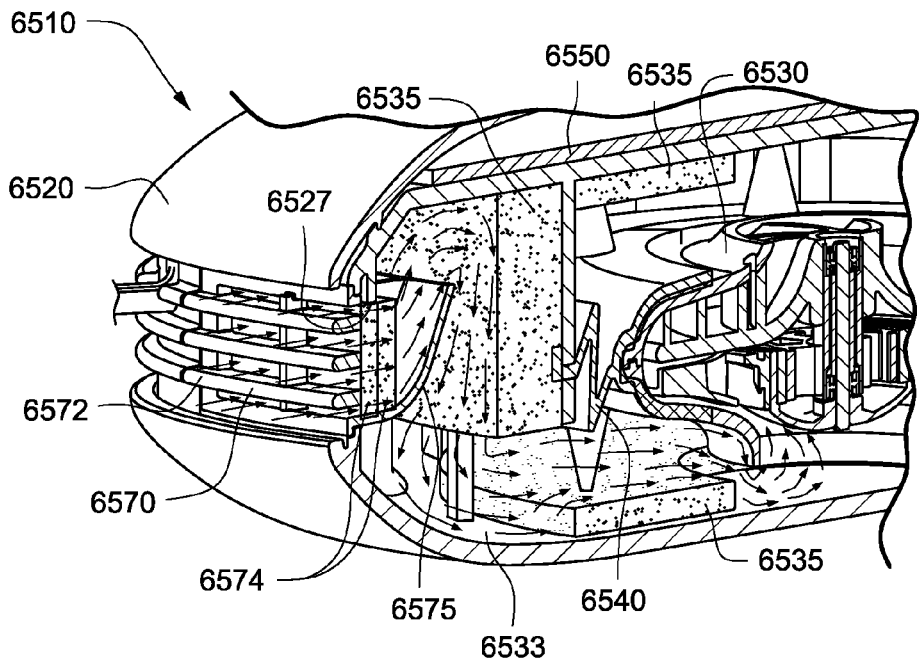
Figures 11, 101:
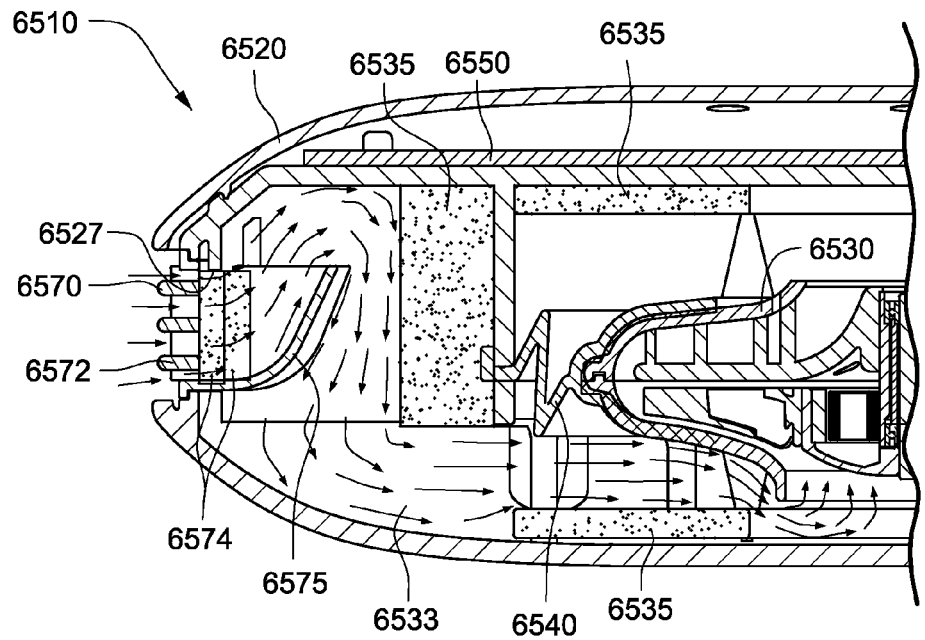

FIGS. 101-1 to 101-11 illustrate a flow generator 6510 according to an example of the present technology. Such example is similar to the flow generator 10. In contrast, this example shows further details of an exemplary blower (described in U.S. Provisional Application Nos. 61/457,526, filed Apr. 18, 2011, and 61/630,920, filed Dec. 22, 2011, each of which is incorporated herein by reference in its entirety), shows another example of an air filter or filter cartridge at the inlet opening, and shows exemplary positioning of acoustic foam, for example.

In the illustrated examples, the flow generators 10, 6510 are relatively small and flat, i.e., low profile configuration. In an example, as shown in FIG. 101-1, the flow generator may have a length L of about 130-150 mm (e.g., 139 mm), a width W of about 90-110 mm (e.g., 102 mm), and a height H of about 40-60 mm (e.g., 50 mm). However, it should be appreciated that other suitable dimensions are possible.

Figure 8:
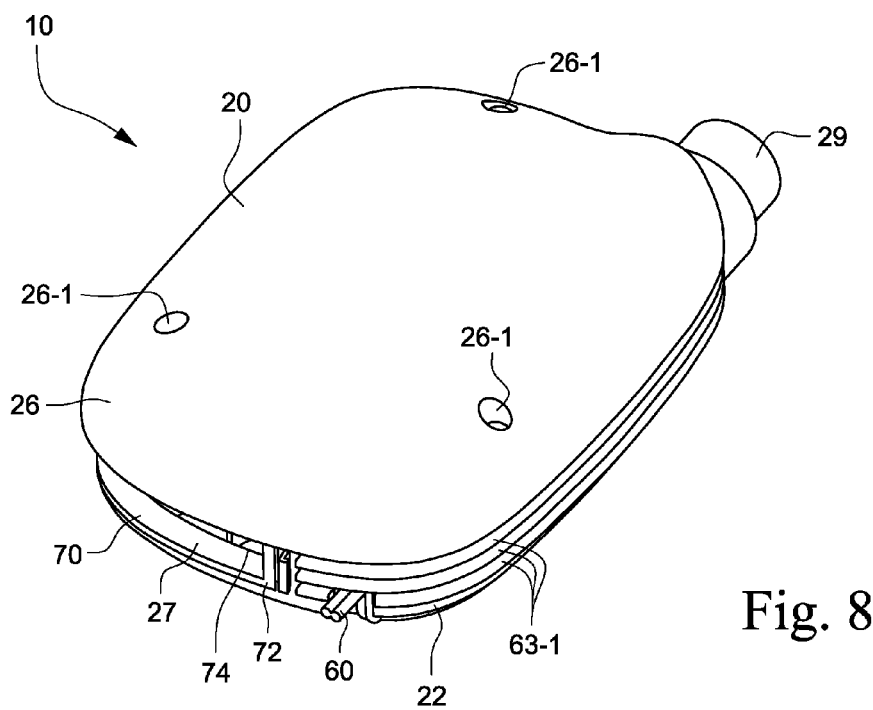
FIG. 8 is a bottom perspective view of the flow generator of FIG. 1.
Figure 9:
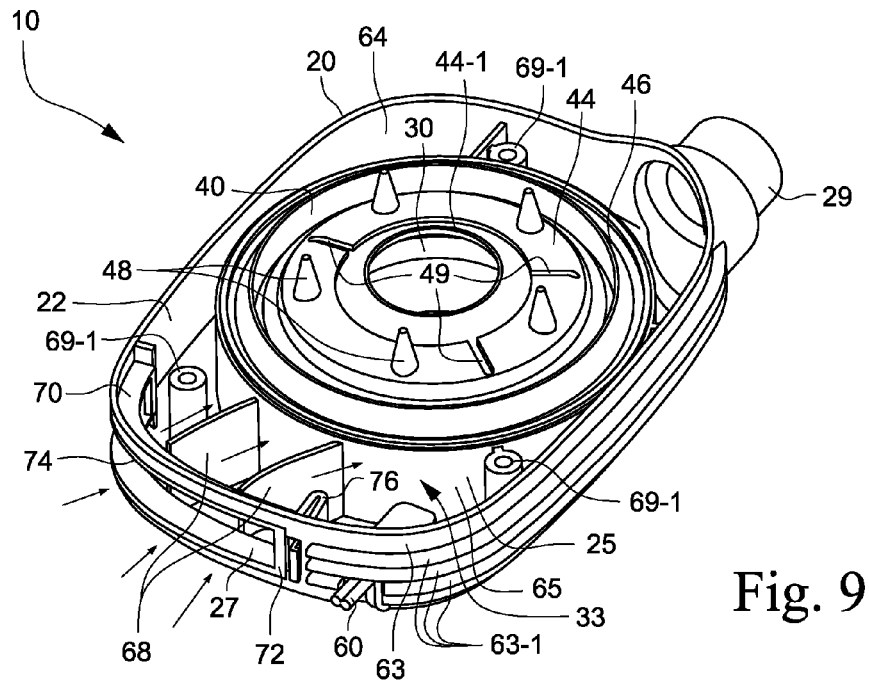
FIG. 9 is a bottom perspective view of the flow generator of FIG. 1 with the bottom cover removed to show the blower and suspension device.
Figure 10:
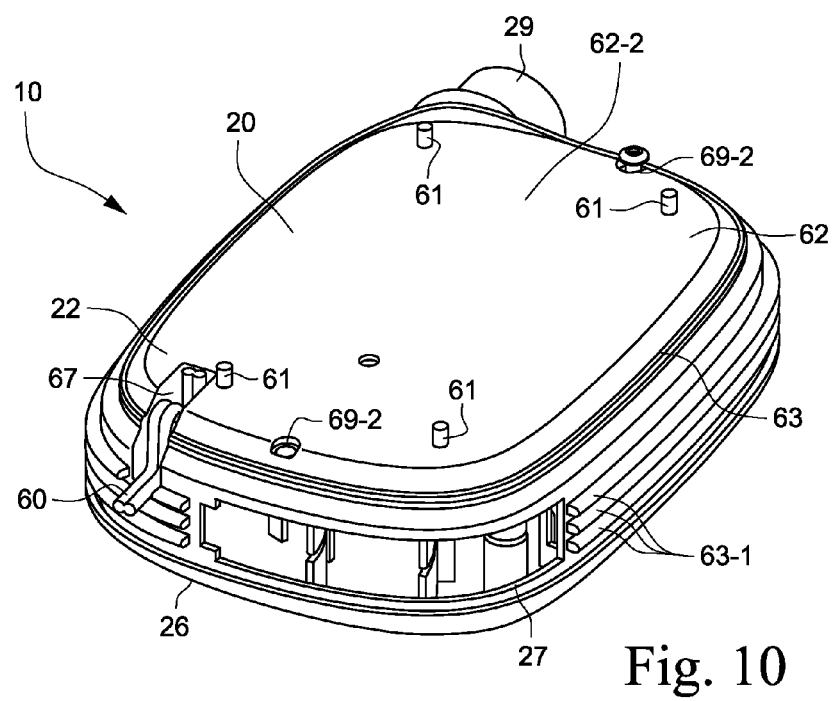
FIG. 10 is another perspective view of the flow generator of FIG. 1 with the top cover and PCB removed.

Exemplary aspects by which the flow generator is made smaller/flatter is detailed below. For example, as best shown in FIGS. 101-8 and 101-9, the blower 6530 integrates the motor components into the same plane as the impeller, i.e., at least some portion of one or more of the motor components is nested within the impeller. As illustrated, the impeller 6501 is positioned around the motor 6502 (including a stator component 6502-1, magnet 6502-2, and rotor cap 6502-3). A bearing-housing structure or diffuser 6503 directs air drawn into the blower inlet 6532 from the impeller 6501 to the blower outlet 6534. As illustrated the blower inlet 6532 and the blower outlet 6534 may be an axial inlet and an axial outlet. The bearing-housing structure 6503 also supports a bearing cartridge 6506 with miniature bearings to simplify the blower design and to act as a connection point between the stator component 6501-1, rotor assembly (rotor cap 6502-3, magnet 6502-2, and rotor 6507) and the blower housing 6508.

The flat blower 6530 is nested within a suspension or support device 6540 which has clearances between the blower inlet 6532 and blower outlet 6534 and the adjacent walls of the blower housing. The suspension device 6540 is preferably constructed of a flexible elastomeric material such as silicone. In an example, this clearance or spacing distance is about 10 mm, as described in more detail below. The suspension device includes cones 6548 that are used as shock absorbers in the axial direction, while a radial bellows-like portion 6546 acts as a shock absorber in the radial direction as described in greater detail below. The suspension device 6540 is structured to be symmetric so that the flow generator 6510 may be operated in any orientation.

Acoustic foam 6535 is used as noise absorption adjacent the blower 6530. As illustrated, a piece of acoustic foam 6535 is provided along the FG housing 6520 adjacent the blower inlet 6532 and a piece of acoustic foam 6535 is provided along the FG housing 6520 adjacent the blower outlet 6534. Holes are cut in each piece of acoustic foam to allow for appropriate clearance for air flow. However, in an alternative example, the acoustic foam pieces may cover the entire FG housing surface adjacent the blower inlet 6532 and blower outlet 6534. In an example, each piece of acoustic foam 6535 includes a thickness of about 5 mm however other suitable thicknesses are possible, e.g., 5 mm or more, greater than 10 mm.

The flow generator 6510 has an inlet chamber 6533 which provides an air filter 6570, acoustic foam 6535 for acoustic noise absorption, and a semi-torturous path to reduce radiated noise (e.g., see FIGS. 101-10 and 101-11), as described in more detail below.

The printed circuit board (PCB) 6550 contains the majority or all the hardware for the blower control and user interface. The PCB 6550 is located outside the flow generator air path to allow maximum size with minimal influence on the air flow and noise reduction features. As described above, the flow generator (FG) housing 6520 includes a chassis 6522, a top cover 6524 provided to one side of the chassis 6522, and a bottom cover 6526 provided to the opposite side of the chassis 6522.

The power supply is located outside the flow generator to minimize flow generator size.

The suspension device 6540 was designed to be symmetric so that the flow generator may be operated in any orientation (right side up, upside down, oblique and/or on edge, etc.), e.g., as the flow generator 6510 may potentially be located in the bed with the user and consequently may be bumped or moved during the night. A button rim 6580-1 (e.g., see FIGS. 101-1, 101-3) was designed around the button 6580 for the user interface to reduce chance inadvertent activation or deactivation in case the flow generator was rolled onto by the user in the bed during use. The user interface also includes a "double-click" deactivation function or the like, such that the user must intentionally deactivate the flow generator and the flow generator is less likely to be deactivated in case the user or bed partner roll over the flow generator in their sleep.

The air flow inlet 6527 is located on the center section of the flow generator 6510 to decrease the chance of the air flow inlet being blocked when in the bed, and in particular the air flow inlet is not located on the largest sides of the flow generator which are likely to be the surfaces that the flow generator rests on. The air flow outlet 6529 may be located on an opposing side of the flow generator 6510 as shown or on any side of the flow generator 6510 including the same side as the air flow inlet 6527 (not shown).

The small, low profile flow generator 6510 includes several noise reduction features. The main noise reduction started at the noise source, i.e., the blower. For example, the diameter of the blower inlet 6532 was tuned to minimize radiated noise from the blower 6530. The height of the chimney of the blower inlet 6543 was also tuned to reduce the air volume resonance of the blower. As noted above, acoustic noise absorption foam was used in the blower chamber 6525 and in the inlet chamber 6533 of the flow generator housing and structured to include lower limits of size but still provide effective noise reduction. A thicker air filter media 6574 was used in conjunction with the air filter 6570 that directs the air away from the blower inlet 6527, and then through a number of vanes 6577 which act as manifolds to reduce the turbulence through the blower.

2.1.1 Chassis

Referring to FIGS. 1-14, the chassis 22 includes a main chassis wall 62 and a side wall 63 extending from the main chassis wall 62 to define a chassis interior 64. The main chassis wall 62 includes an interior side 62-1 (see FIG. 14) that defines the chassis interior and an exterior side 62-2.

Figure 14:
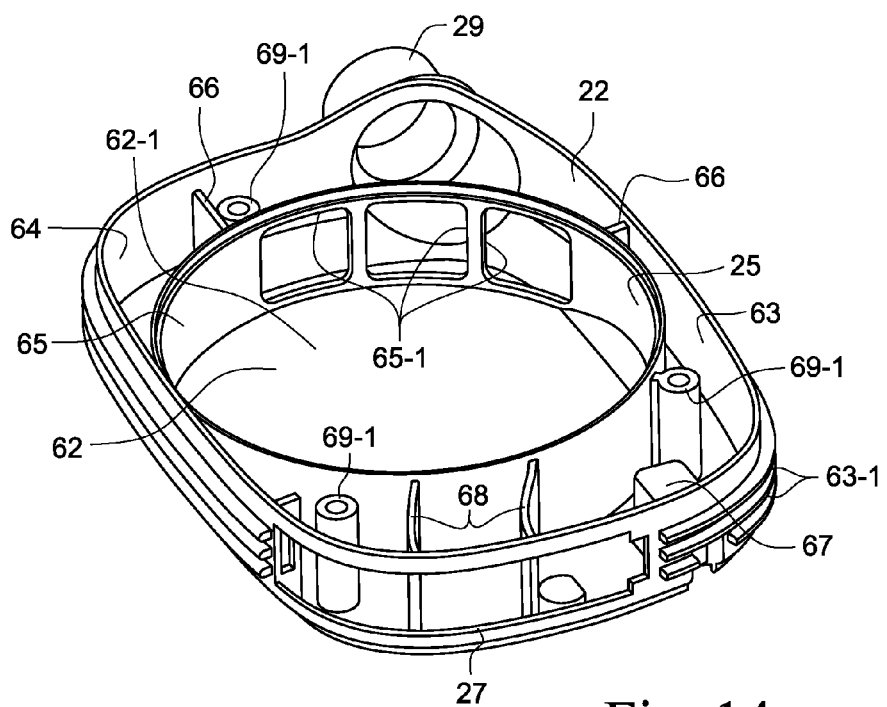
FIG. 14 is another perspective view of the chassis of the flow generator of FIG. 1.
Figure 15:
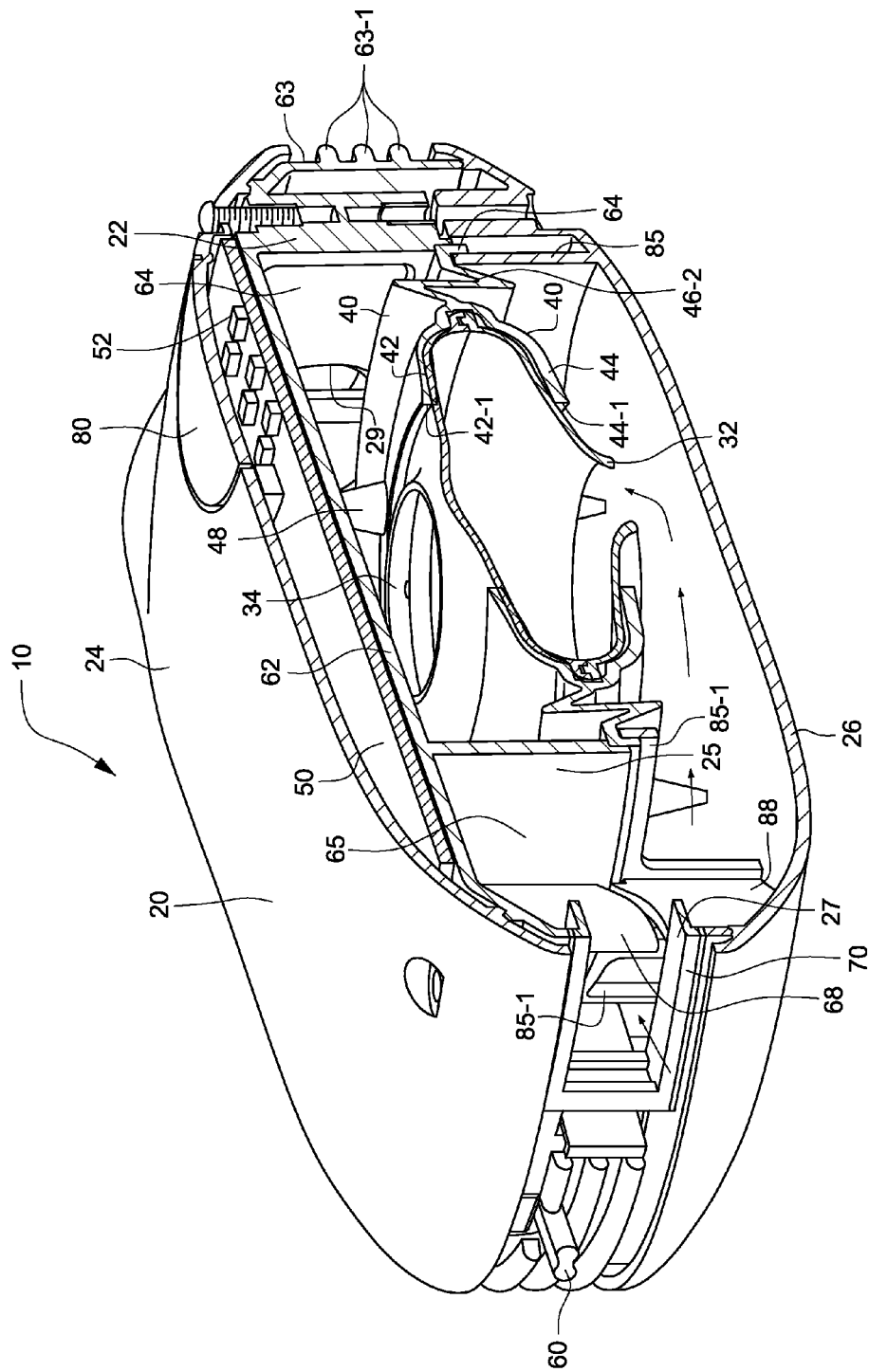
FIGS. 15-22 are various cross-sectional views of the flow generator of FIG. 1.
Figure 16:
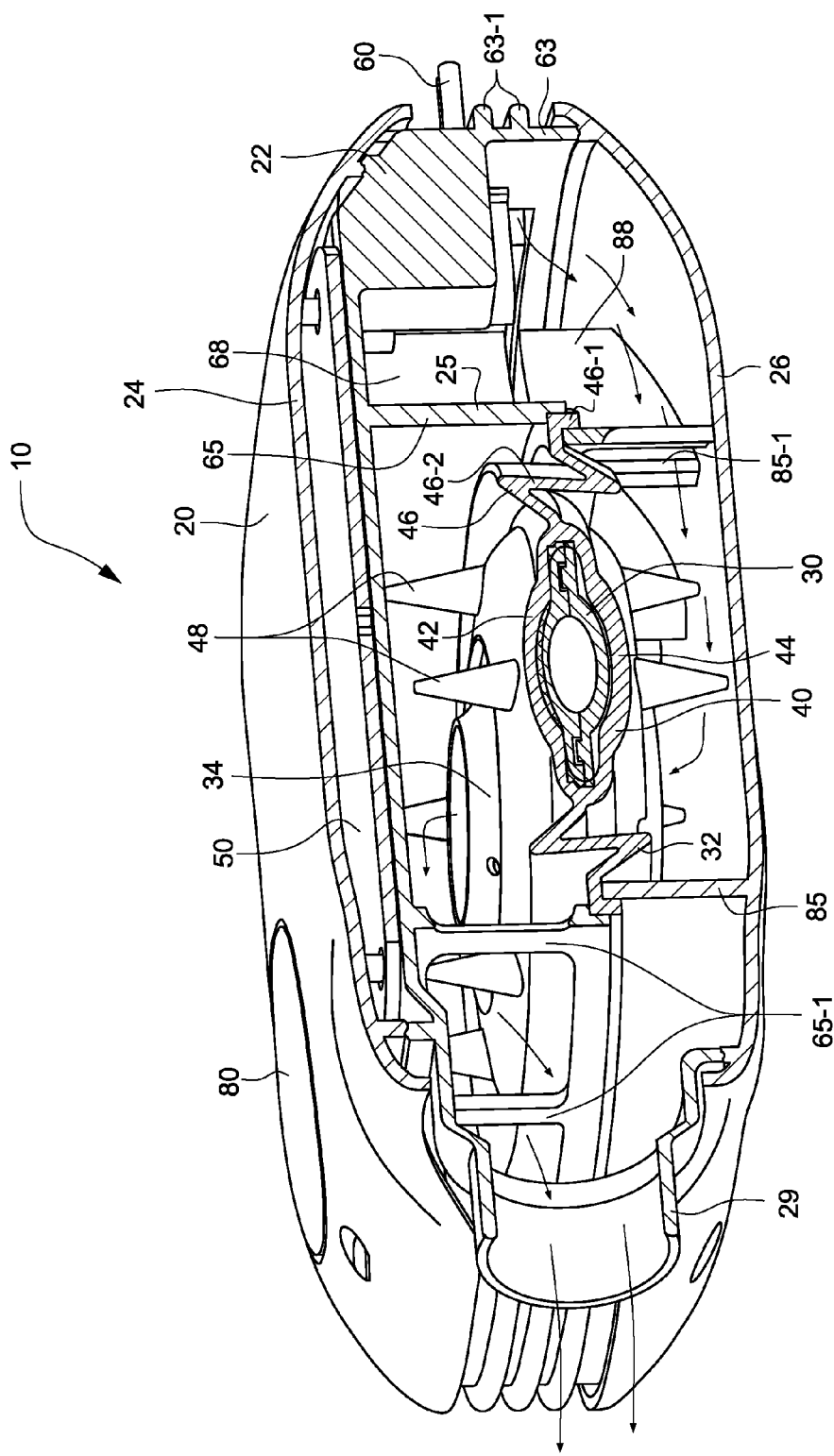
Figure 17:
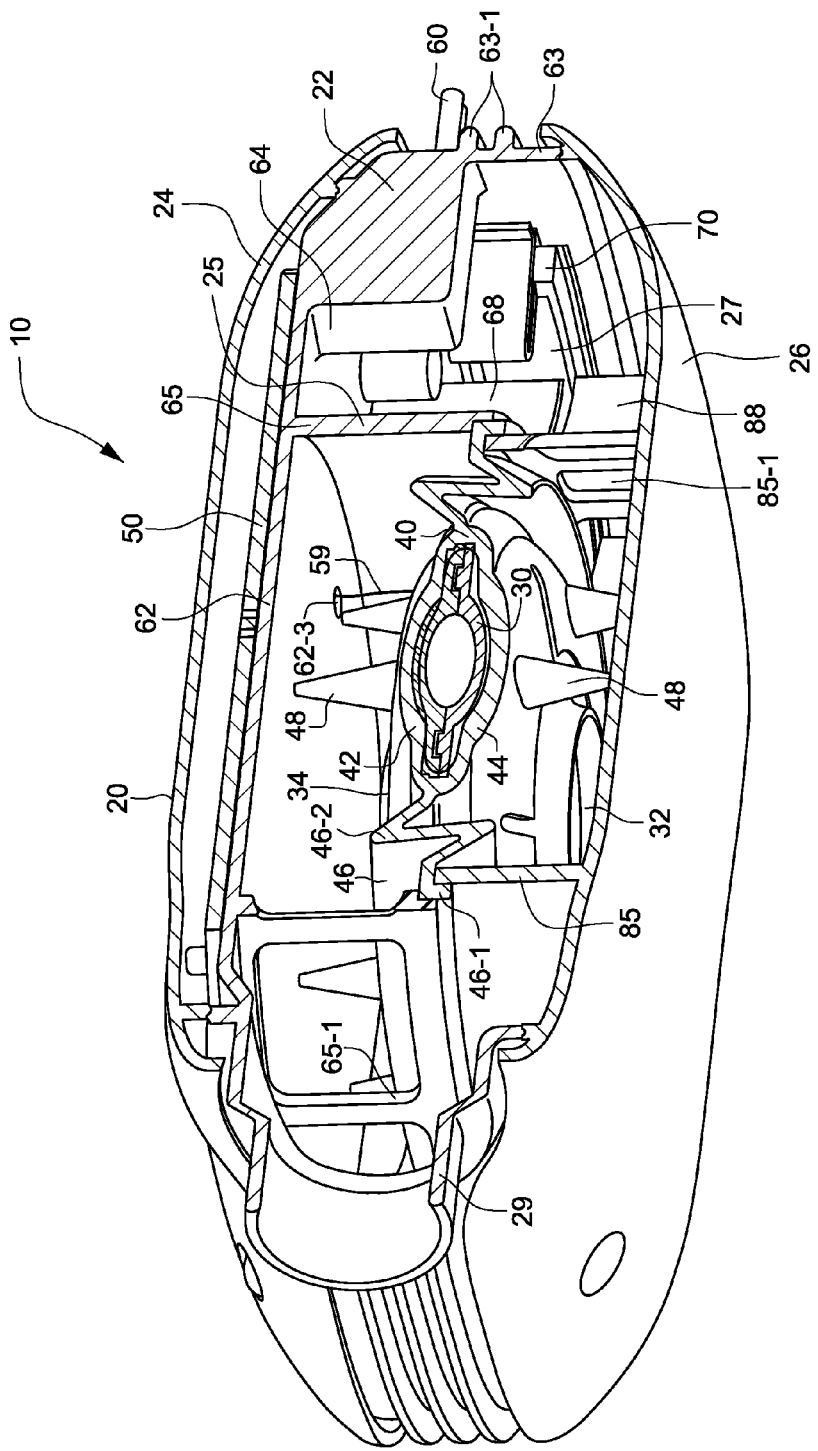

Fastener receptacles 69-1 are provided within the chassis interior and configured to receive fasteners adapted to secure the bottom cover 26 to the chassis 22 (e.g., see FIGS. 9 and 14). Also, fastener receptacles 69-2 are provided to the chassis and configured to receive fasteners adapted to secure the top cover 24 to the chassis (e.g., see FIGS. 10 and 13).

Outlet

Referring to FIGS. 1-22, the air flow outlet 29 is provided to the side wall 63 and adapted to be connected to an air delivery tube or conduit 5 for delivery of a flow of breathable gas to a patient interface. As illustrated, the air flow outlet 29 is offset or asymmetrical with respect to a longitudinal axis of the FG housing 20. However, it should be appreciated that the air flow outlet 29 may be arranged in other suitable manners, e.g., a central or symmetrical outlet.

Figure 104:
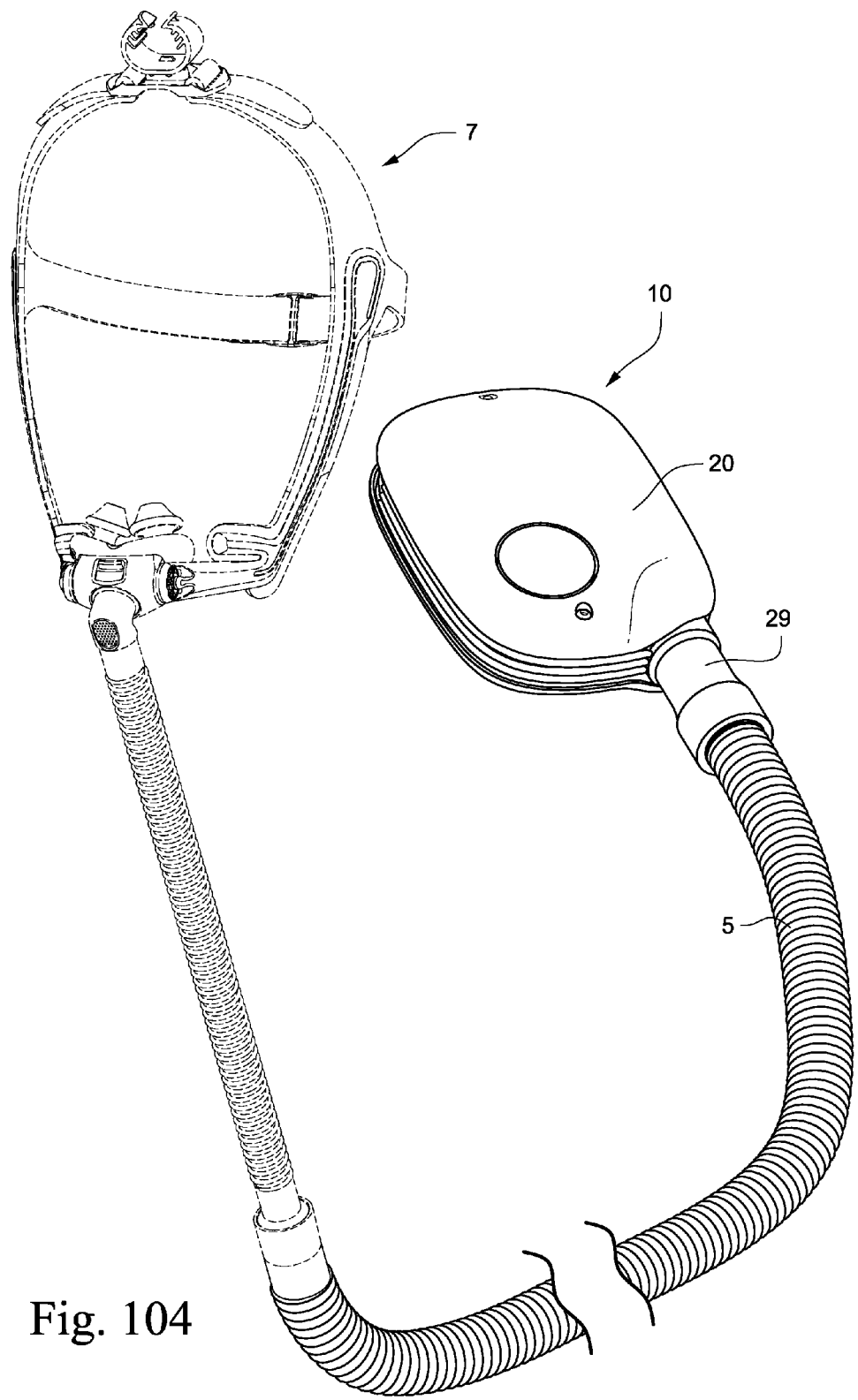
FIG. 104 is a perspective view showing a flow generator communicated with a patient interface or mask via an air delivery conduit according to an example of the present technology.

FIG. 104 shows an example of the flow generator 10 communicated with a patient interface or mask 7 via air delivery conduit 5. In the illustrated example, the patient interface includes a nasal prong assembly, e.g., as disclosed in U.S. Patent Publication No. US-2009-0044808 which is incorporated herein by reference in its entirety. However, it should be appreciated that the patient interface or mask may have other suitable configurations as is known in the art, e.g., full-face mask, nasal mask, oro-nasal mask, mouth mask, nozzles, nasal prongs, nasal pillows, cannula, etc.

Inlet

The air flow inlet 27 is provided to the side wall 63. As illustrated, the air flow inlet 27 is provided on a side of the chassis 22 opposite to the air flow outlet 29. The air flow inlet 27 receives or otherwise supports the air filter 70. However, it should be appreciated that the air flow inlet 27 may be arranged in other suitable manners. In an example, the air flow inlet is structured to ensure that it does not become blocked, e.g., by bed sheets, etc. in use as the flow generator may be located within the bed or under bedding.

Figure 7:
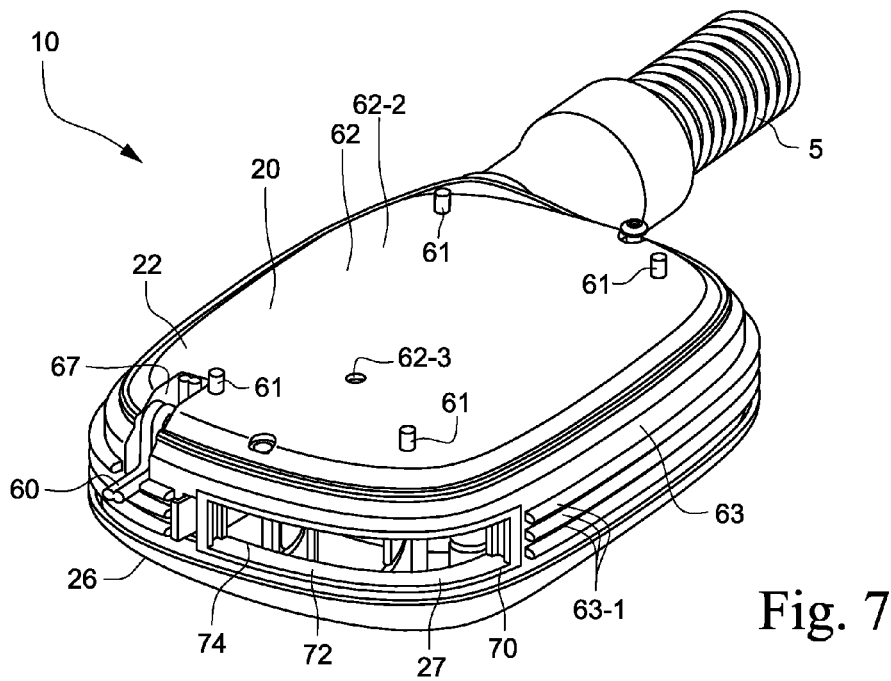
FIG. 7 is another perspective view of the flow generator of FIG. 1 with the top cover and PCB removed.
Figures 1, 23:
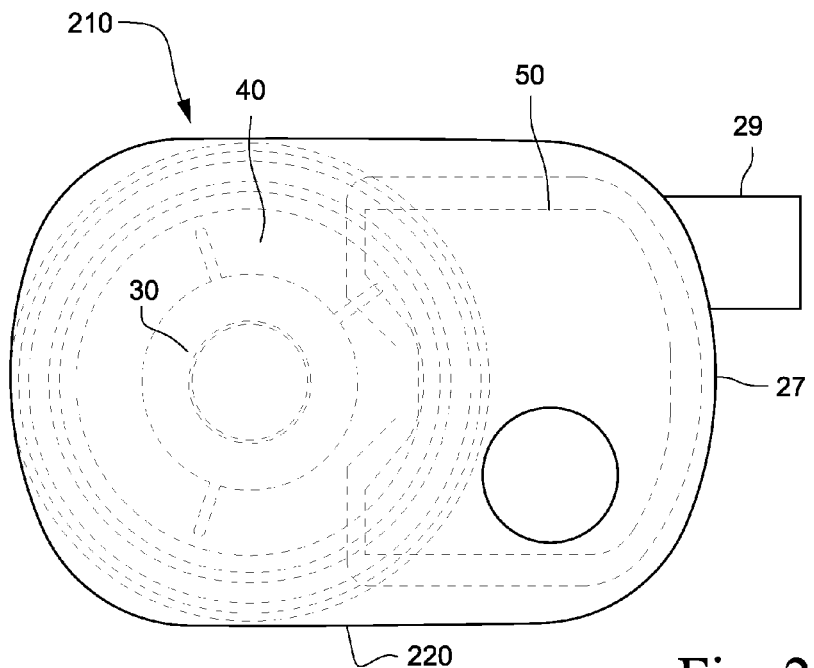
Figures 2, 23:
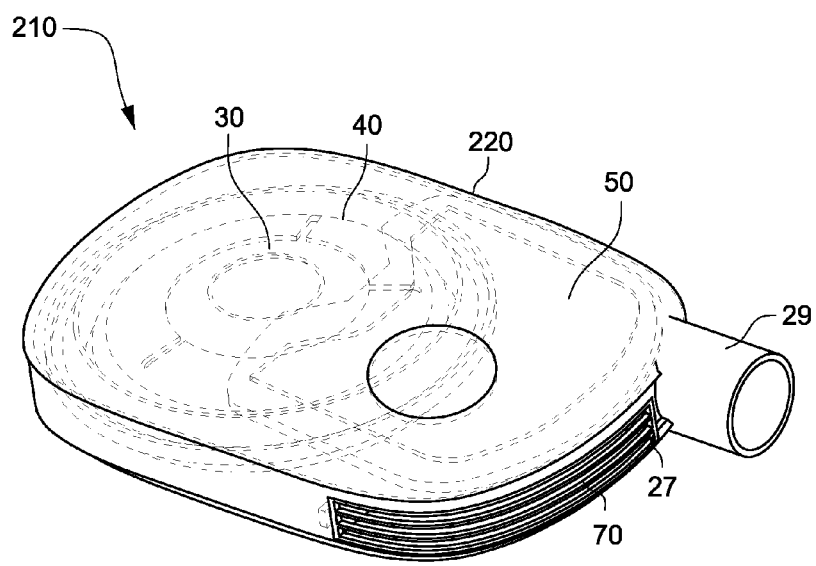
Figures 3, 23:
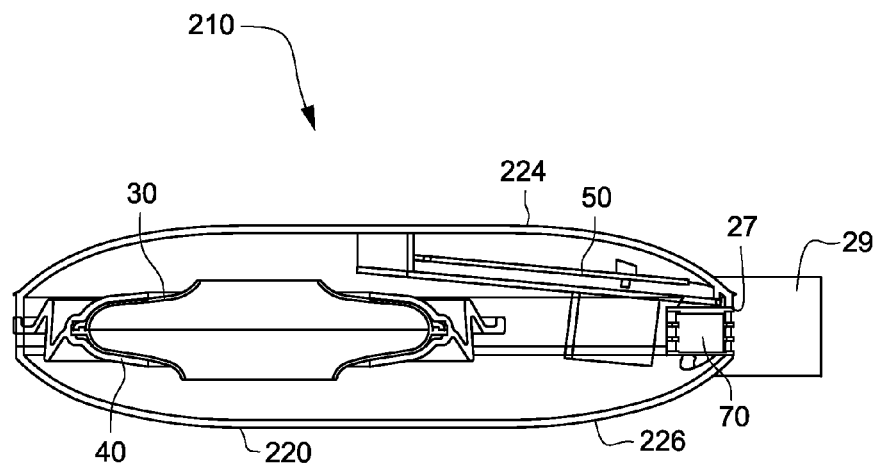
Figures 4, 23:
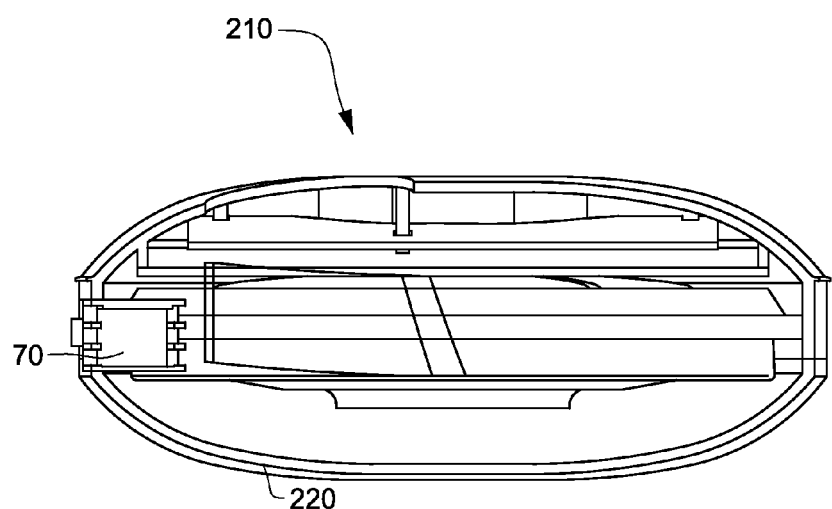
Figures 5, 23:
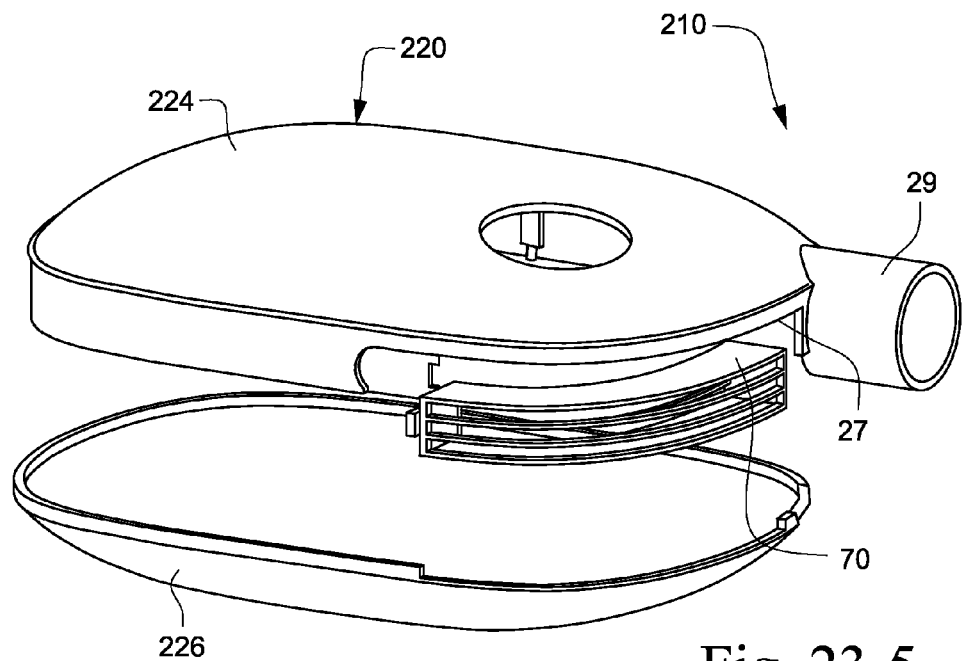
Figures 6, 23:
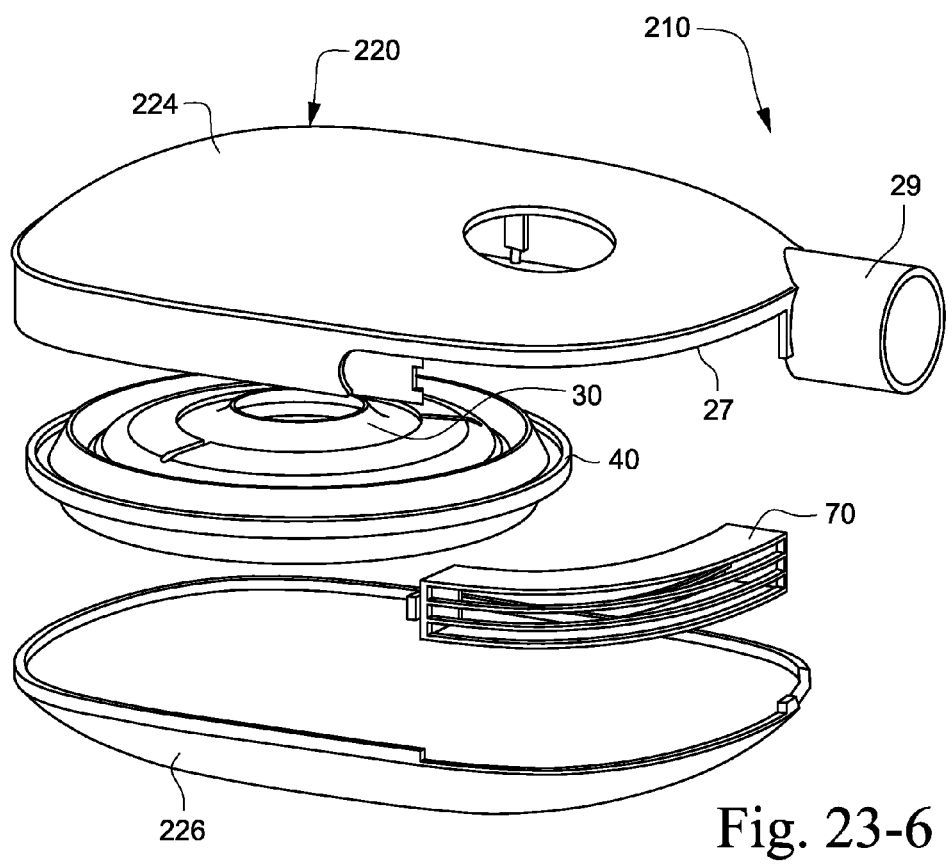
Figures 7, 23:
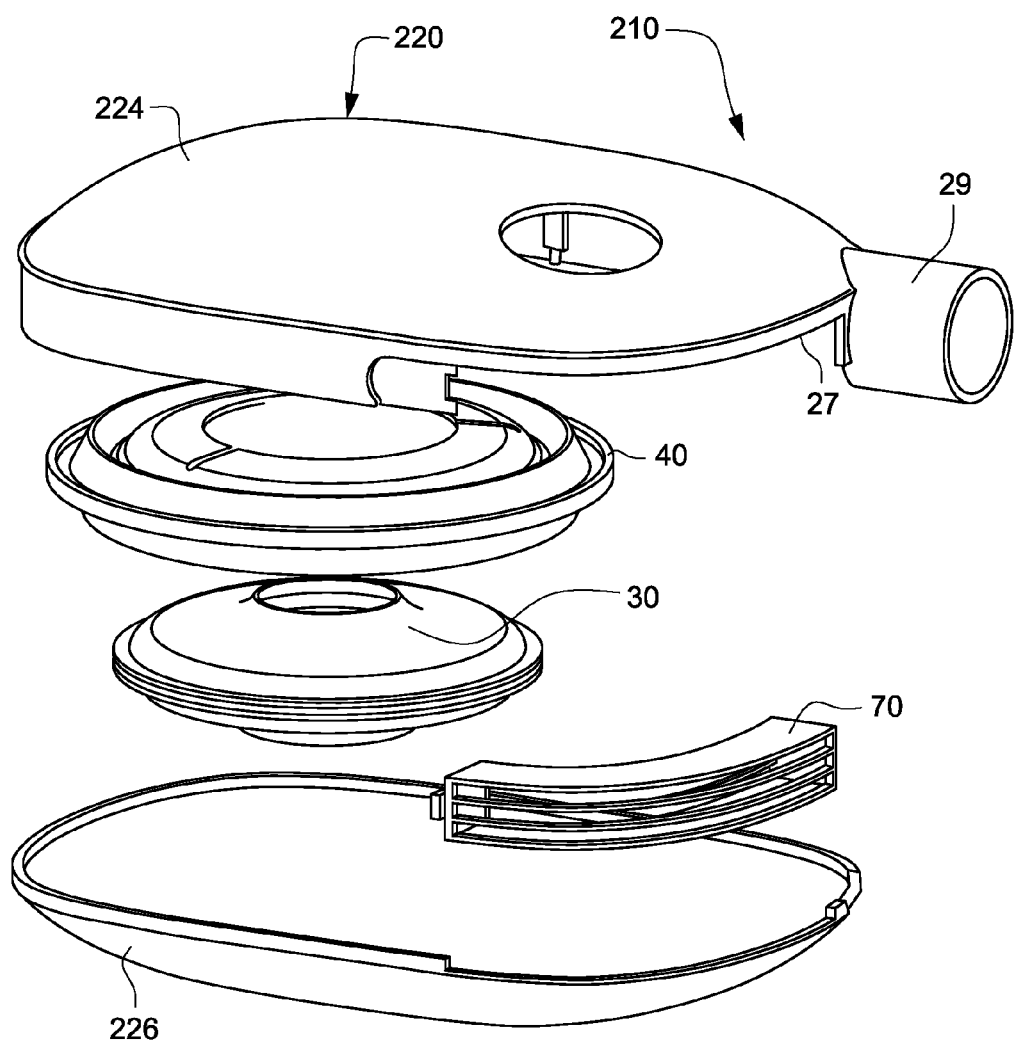

For example, FIGS. 23-1 to 23-7 illustrate a flow generator 210 in which the air flow inlet 27 and air filter 70 supported therewithin are provided on the same side of the FG housing 220 as the air flow outlet 29. In this example, the FG housing 220 includes upper and lower housing parts 224, 226 that cooperate to support the blower 30 and suspension device 40. Also, the blower 30 and suspension device 40 are positioned along one side of the FG housing 220 and the PCB 50 is positioned along the other side of the FG housing 220.

Figure 3:
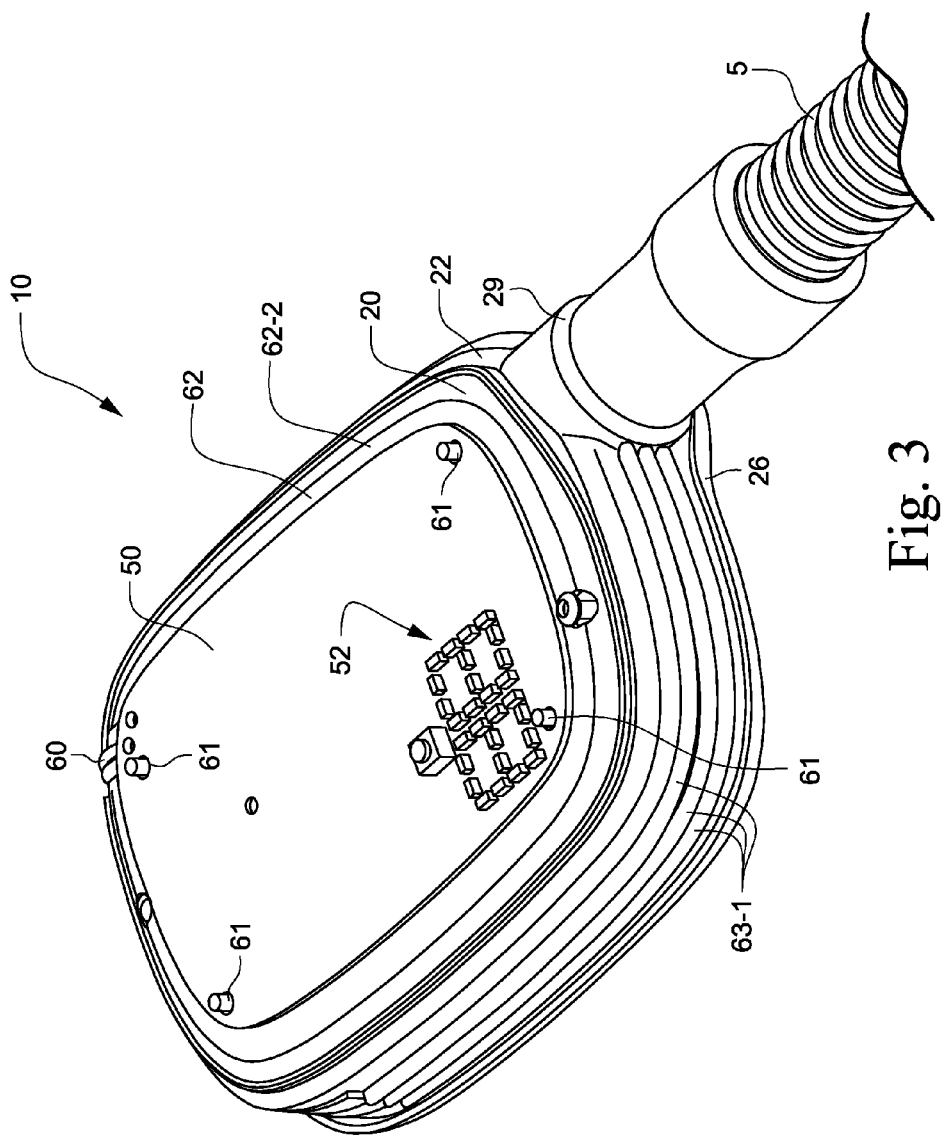
FIG. 3 is a perspective view of the flow generator of FIG. 1 with the top cover removed to show the PCB.
Figure 4:
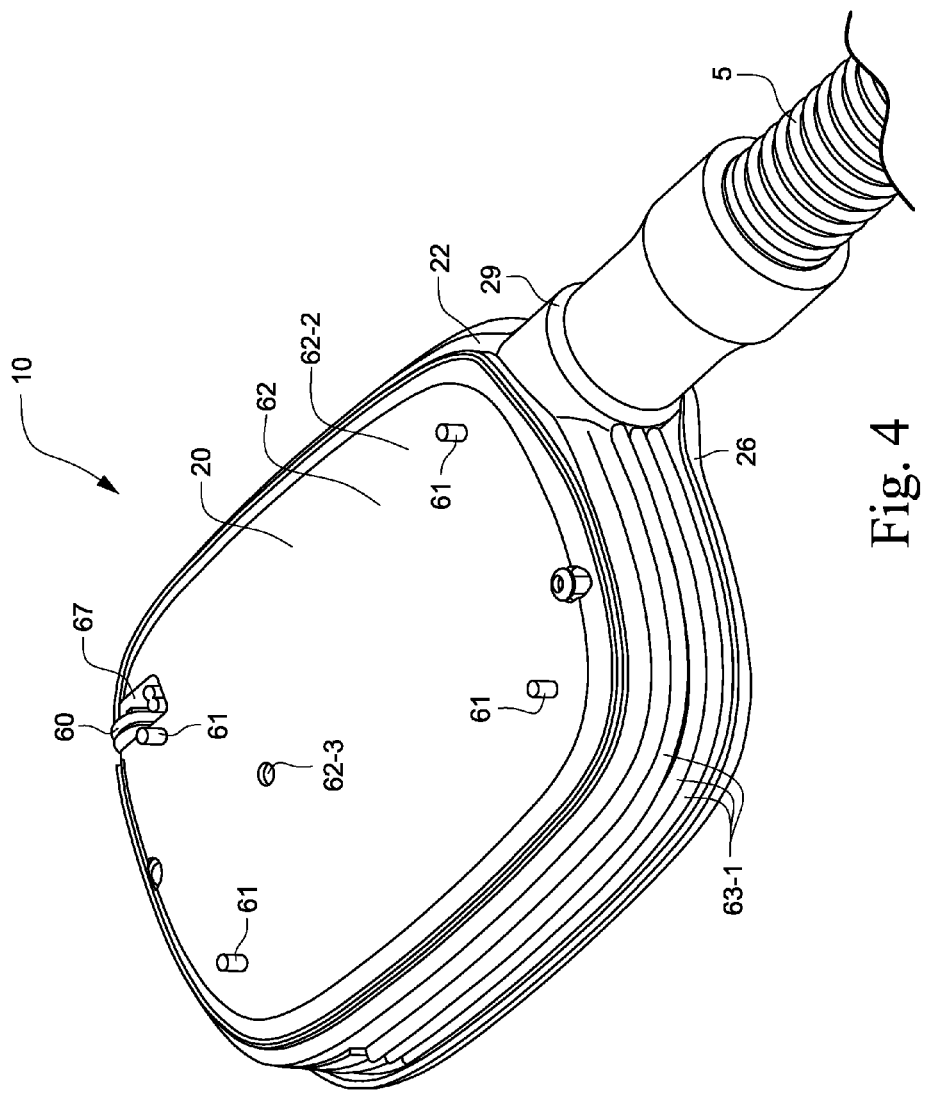
FIG. 4 is a perspective view of the flow generator of FIG. 1 with the top cover and PCB removed.
Figures 1, 25:
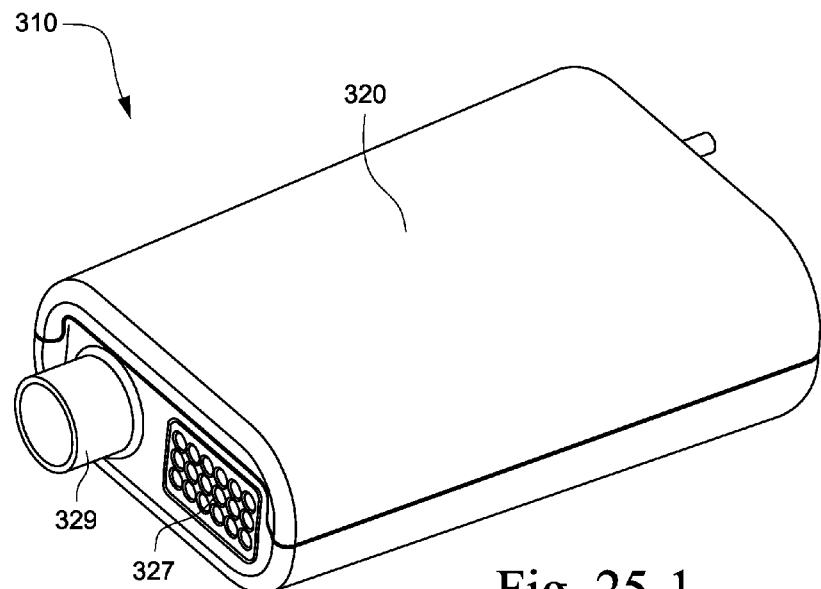
Figures 2, 25:
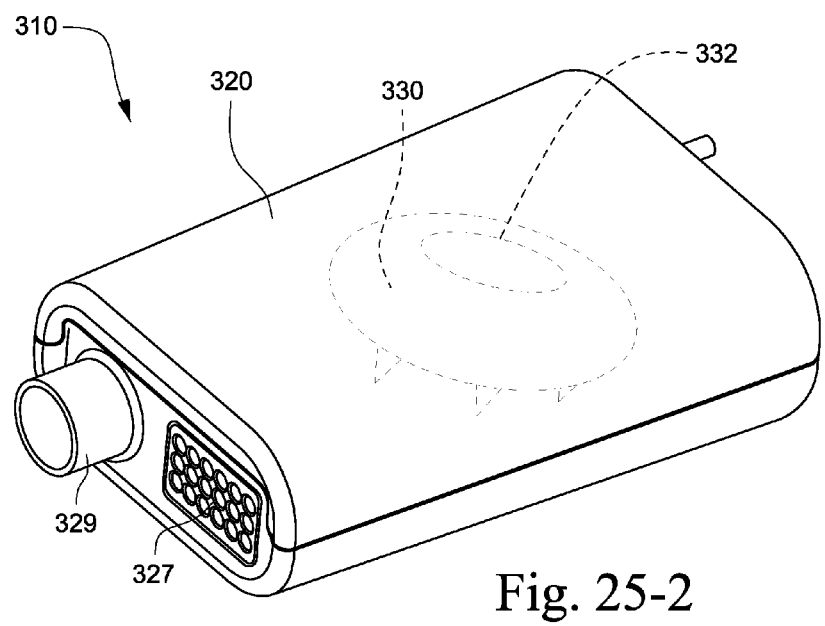
Figures 3, 25:
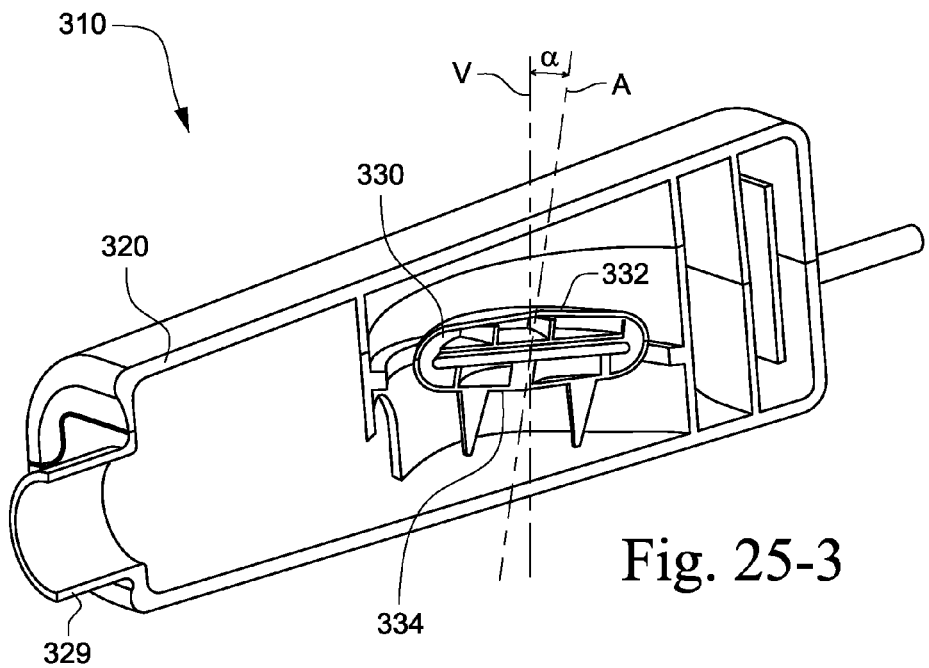
Figures 4, 25:
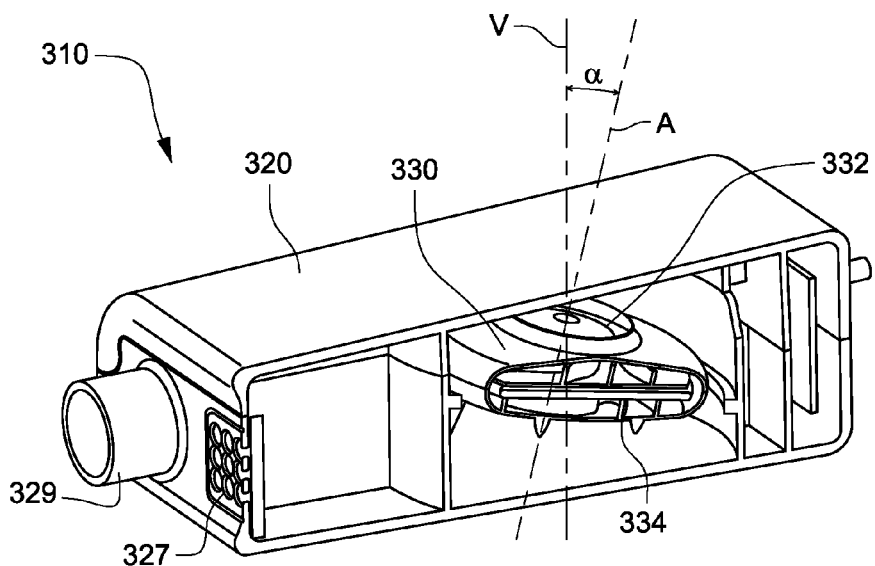
Figures 5, 25:
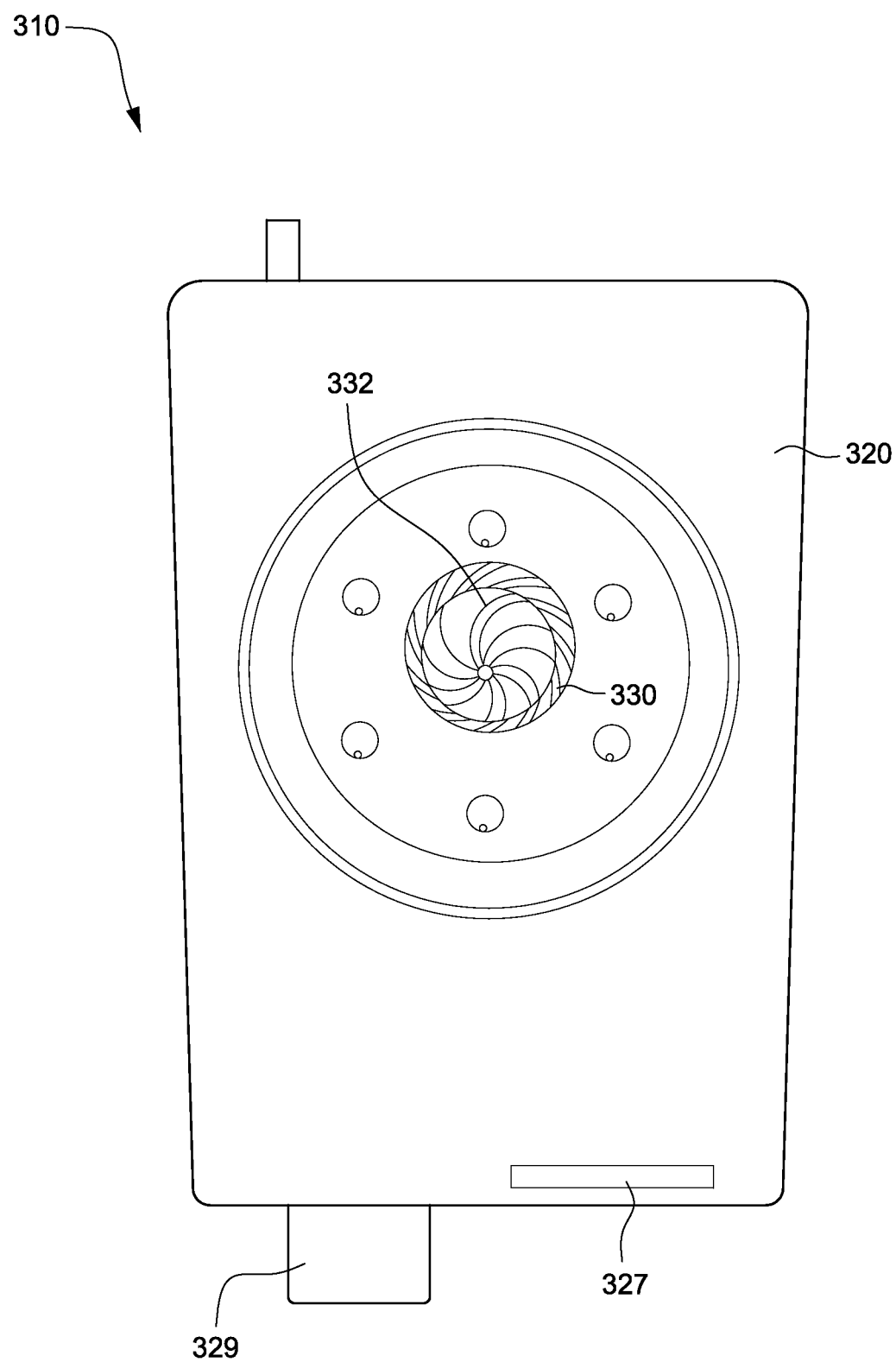
Figures 6, 25:
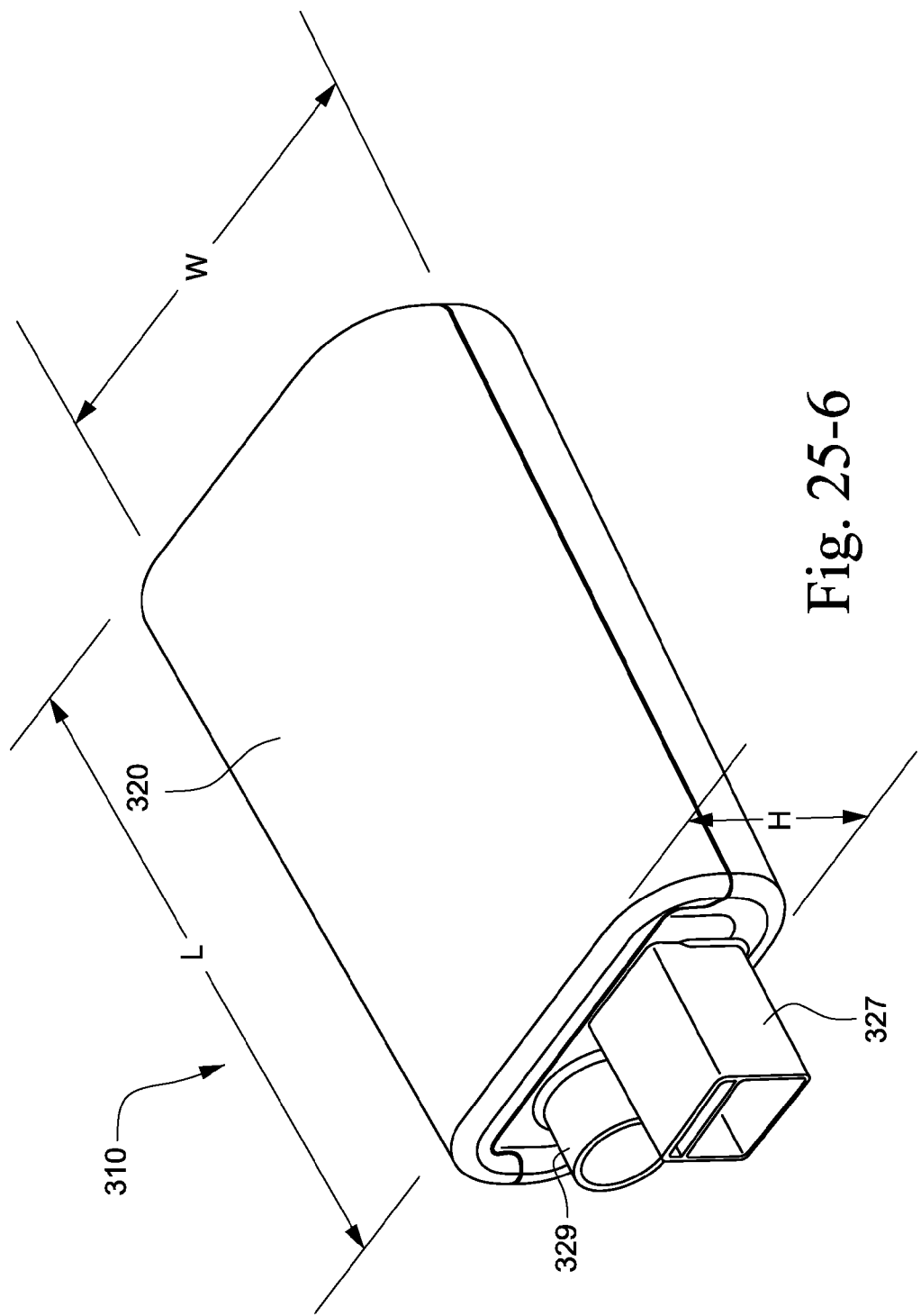
Figures 7, 25:
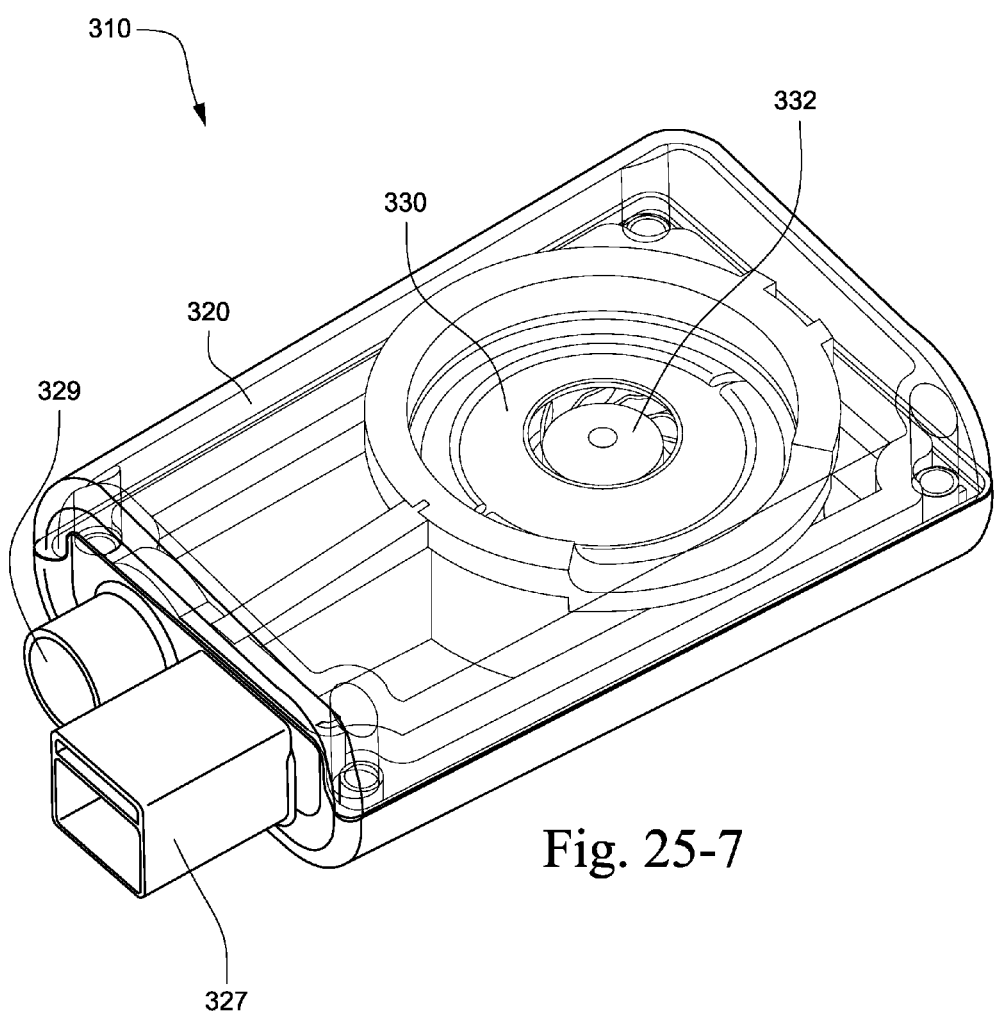
Figures 8, 25:
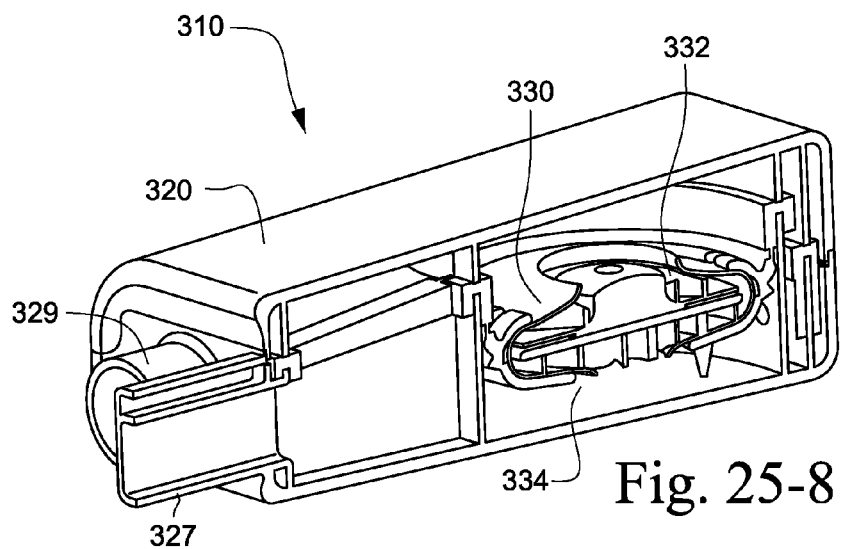
Figures 9, 25:
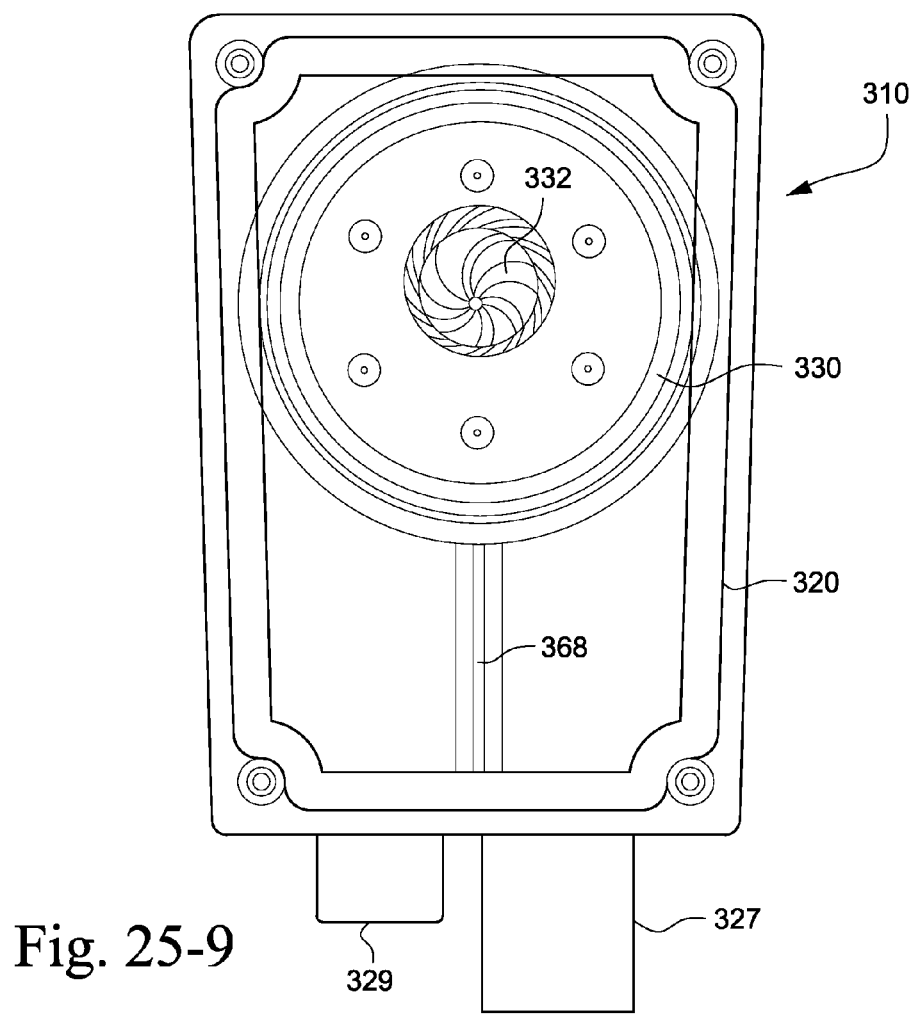
Figures 10, 25:
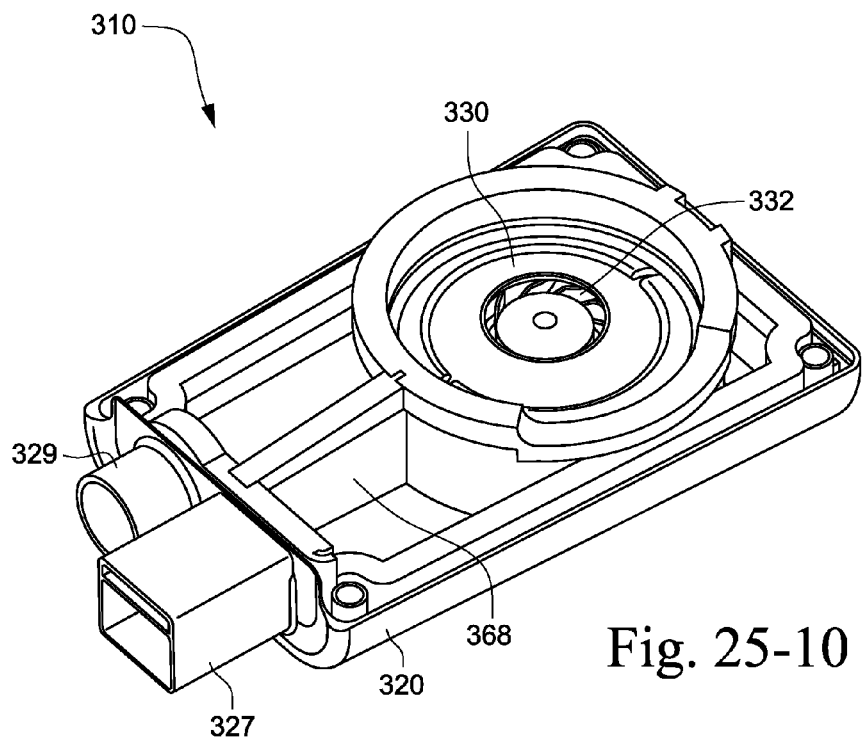
Figures 11, 25:
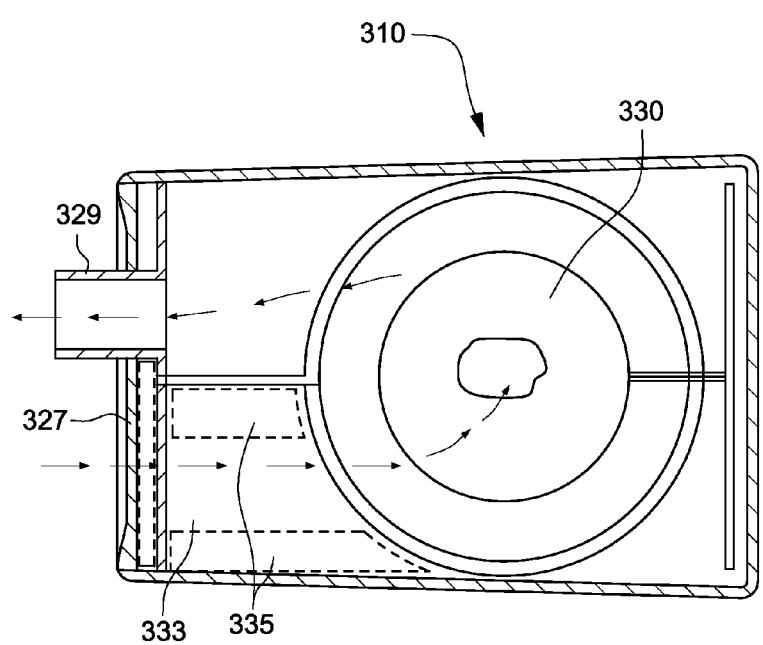

FIGS. 25-1 to 25-11 show a flow generator 310 according to another example of the present technology. In this example, the blower 330 is supported within the housing 320 at an angle such that the blower inlet 332 is oriented away from the inlet 327 of the housing. For example, as best shown in FIGS. 25-3 and 25-4, the central axis A of the blower may be angled by angle α of about 5-20° (e.g., 5°, 10°, 15°, 20°) with respect to a vertical axis V of the flow generator.

The orientation of the blower inlet 332 as well as the tortuous inlet airpath provided by the FG housing 320 makes it more difficult for noise to travel back out of the air flow inlet 327. In addition, the blower outlet 334 is angled towards the air flow outlet 329 of the FG housing 320 to provide a more direct flow path from the blower outlet 334 to the air flow outlet 329, e.g., see FIG. 25-3.

As illustrated, the air flow inlet 327 and the air flow outlet 329 are provided on the same side of the FG housing 320, which arrangement may help prevent the air flow inlet 327 from being blocked when an air delivery tube is attached to the air flow outlet 329. An inlet air flow vane 368 is provided adjacent the air flow inlet 327, which may be movable to adjust the volume of the inlet chamber 333. Also, as shown in FIG. 25-11, acoustic foam 335 may be provided within the inlet chamber 333 along the inlet flow path, e.g., to absorb sound.

Figure 6:
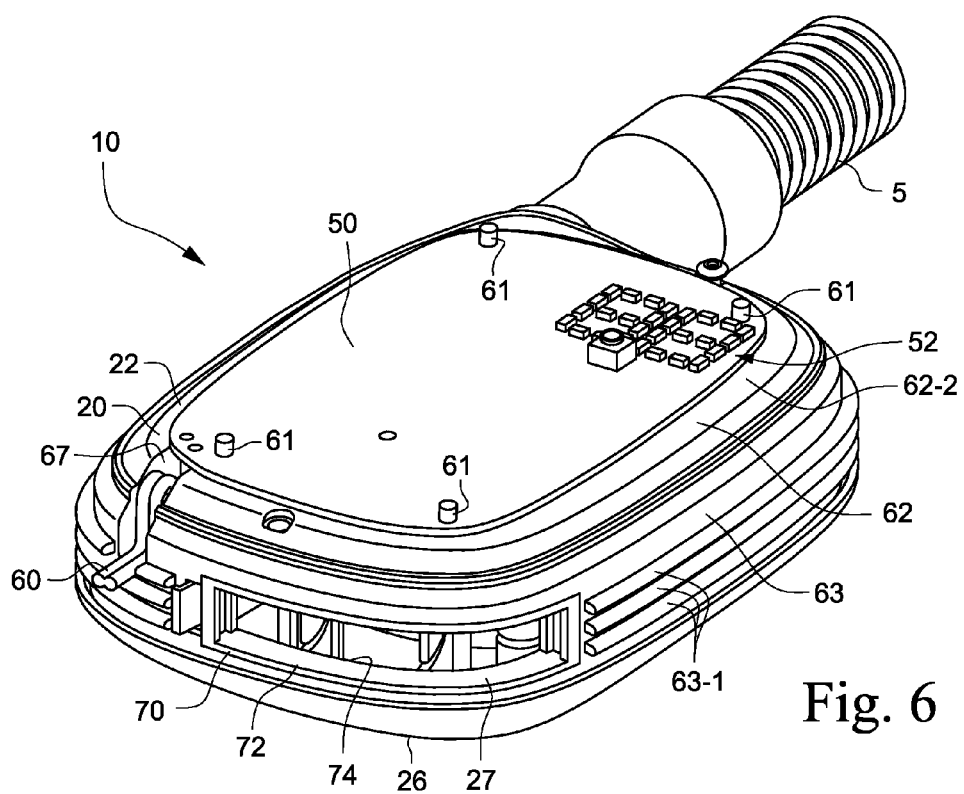
FIG. 6 is another perspective view of the flow generator of FIG. 1 with the top cover removed to show the PCB.

In an example, as shown in FIG. 25-6, the flow generator 310 may have a length L of about 130-160 mm (e.g., 144 mm), a width W of about 90-110 mm (e.g., 100 mm), and a height H of about 40-60 mm (e.g., 50 mm). However, it should be appreciated that other suitable dimensions are possible.

Figure 72:
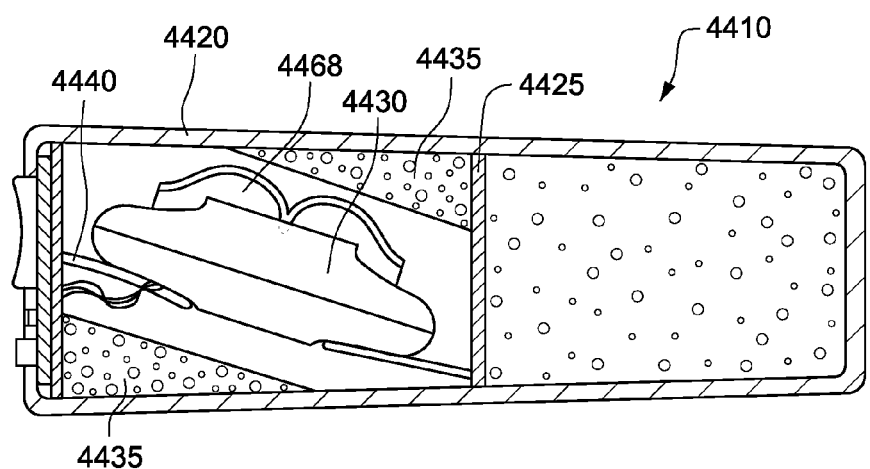
FIG. 72 shows a flow generator according to another example of the present technology.

FIG. 72 shows another example of a flow generator 4410 including a blower 4430 supported within the FG housing 4420 at an angle. A suspension 4440 (e.g., overmolded to one of the housing parts) may support the blower 4430 within the blower chamber 4425. An inlet cap 4468 including inlet vanes may be provided to the inlet side of the blower 4430. Also, one or more pieces of acoustic foam 4435 (e.g., wedge-like foam pieces) may be provided to inlet and outlet sides of the blower, e.g., to direct flow and provide acoustic and shock absorption.

Figure 2:
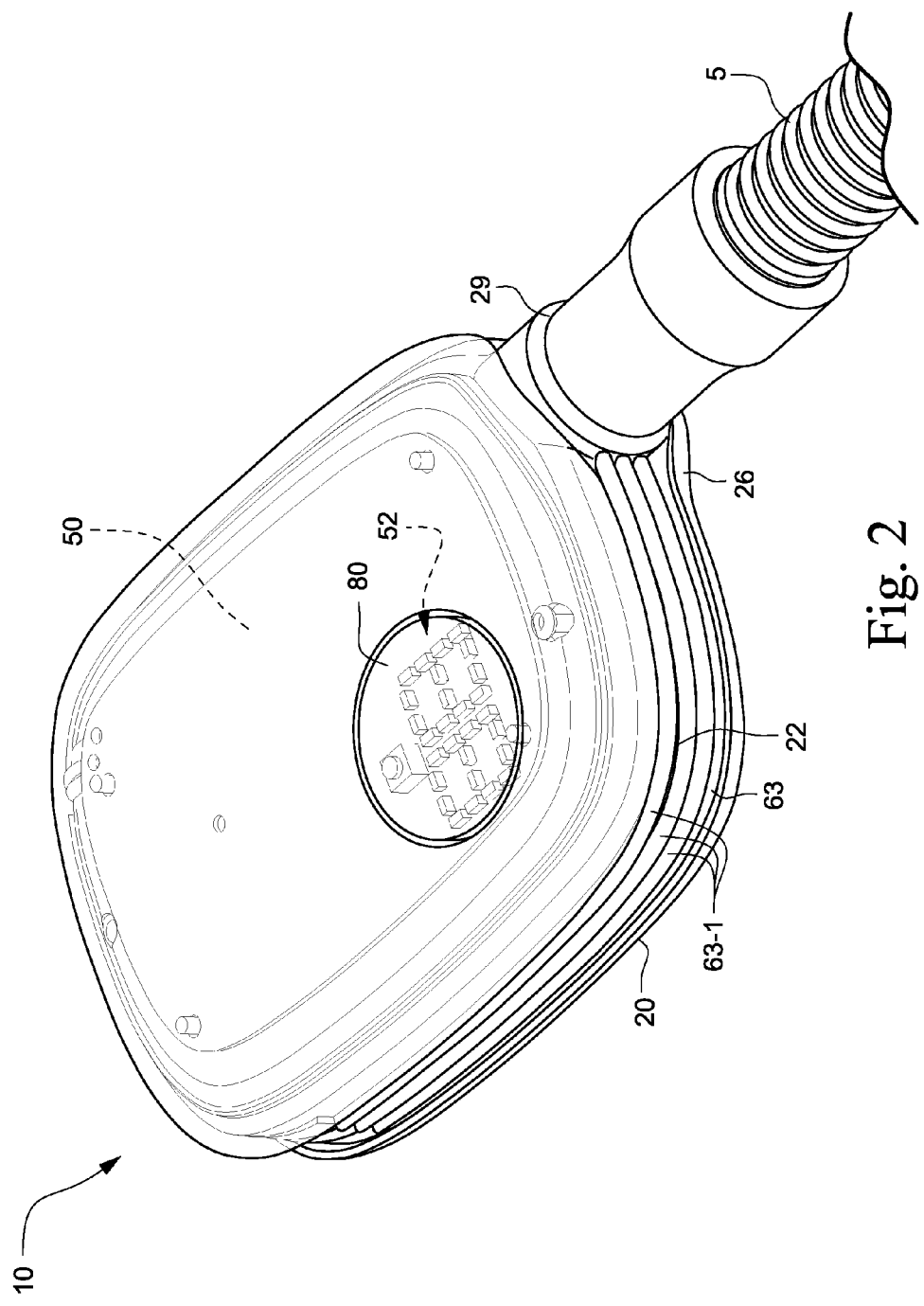
FIG. 2 is a perspective view of the flow generator of FIG. 1 with the top cover shown translucent.
Figures 1, 26:
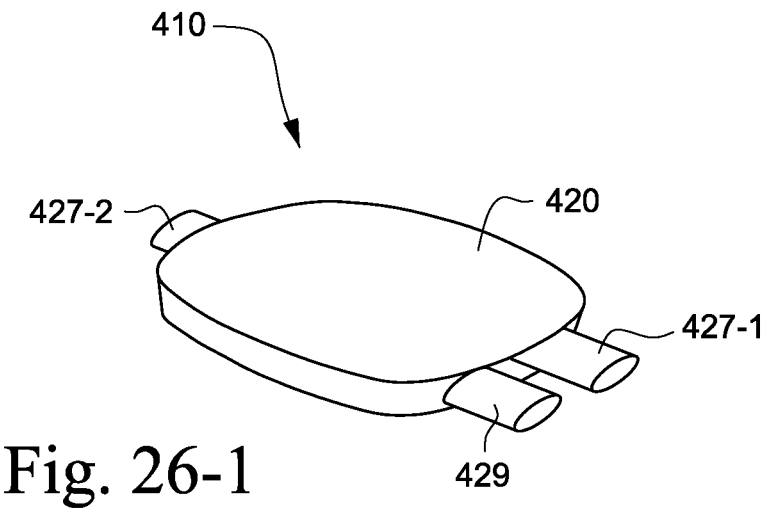
Figures 2, 26:
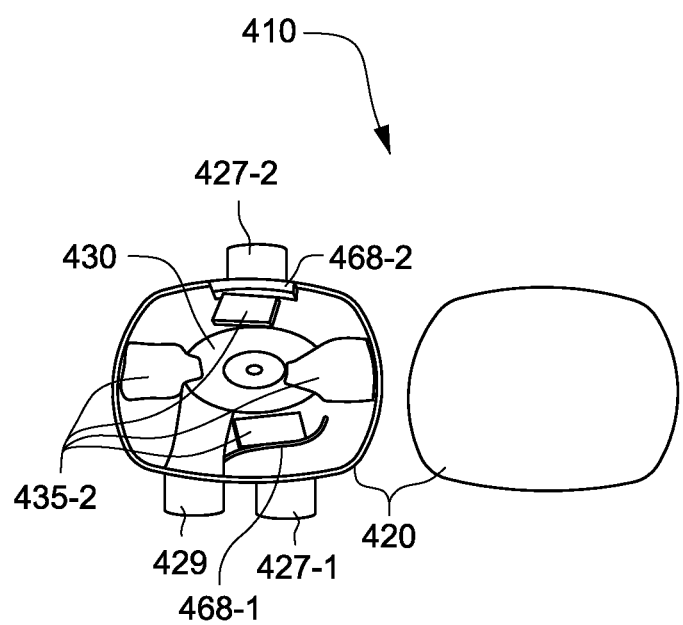
Figures 3, 26:
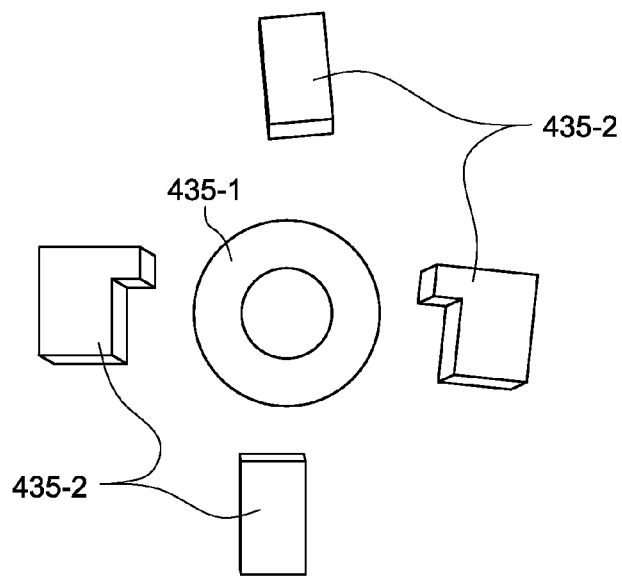

FIGS. 26-1 to 26-3 show a flow generator 410 according to another example of the present technology. In this example, the flow generator 410 includes a FG housing 420 including a air flow outlet 429 and two air flow inlets at different locations, i.e., a first inlet 427-1 provided on the same side of the housing as the outlet 429 and a second inlet 427-2 provided on a side of the housing opposite to the outlet 429. In use, one of the inlets 427-1, 427-2 is blocked off (e.g., by a cap) so that only one inlet is operative, which allows the patient the ability to select an inlet location. An air flow vane 468-1, 468-2 may be provided adjacent respective inlets 427-1, 427-2 for directing air flow. One or more pieces of acoustic foam may be provided to support the blower 430 within the housing 420 and provide sound absorption and suspension. For example, as shown in FIGS. 26-2 and 26-3, an annular or curved foam piece 435-1 may support the base of the blower within the housing and foam blocks 435-2 (e.g., 3, 4, 5, or more foam blocks) may support sides of the blower within the housing. Each of the two air flow inlets, 427-1, 427-2 may be structured to support a respective air filter cartridge (not shown) as described in more detail herein.

Figures 1, 27:
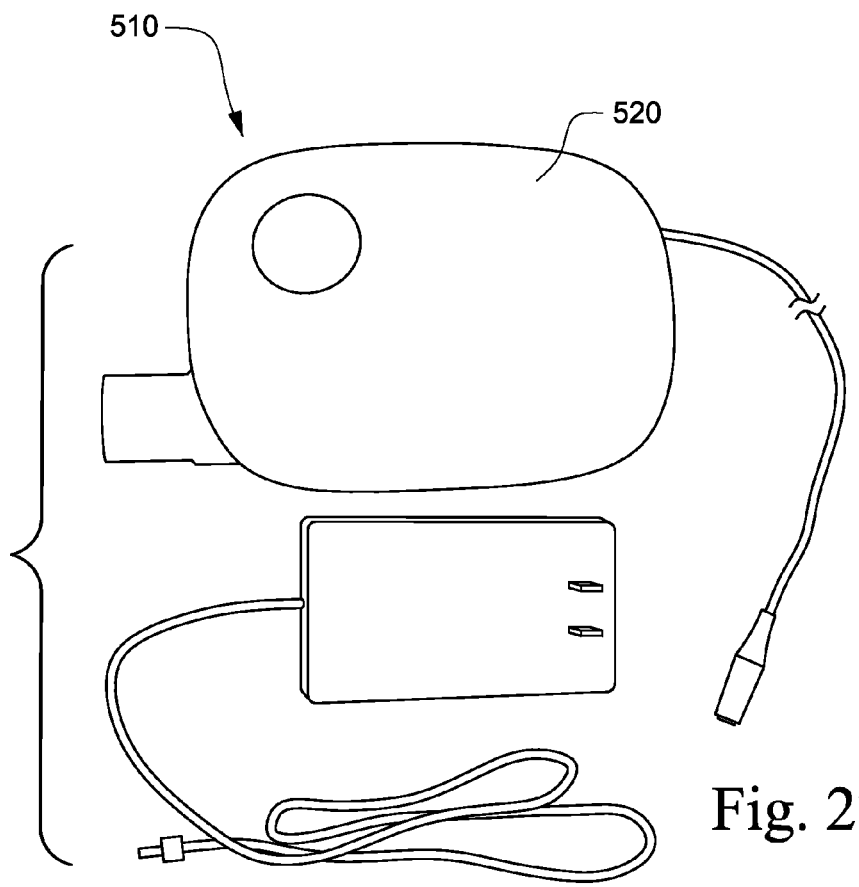
Figures 2, 27:
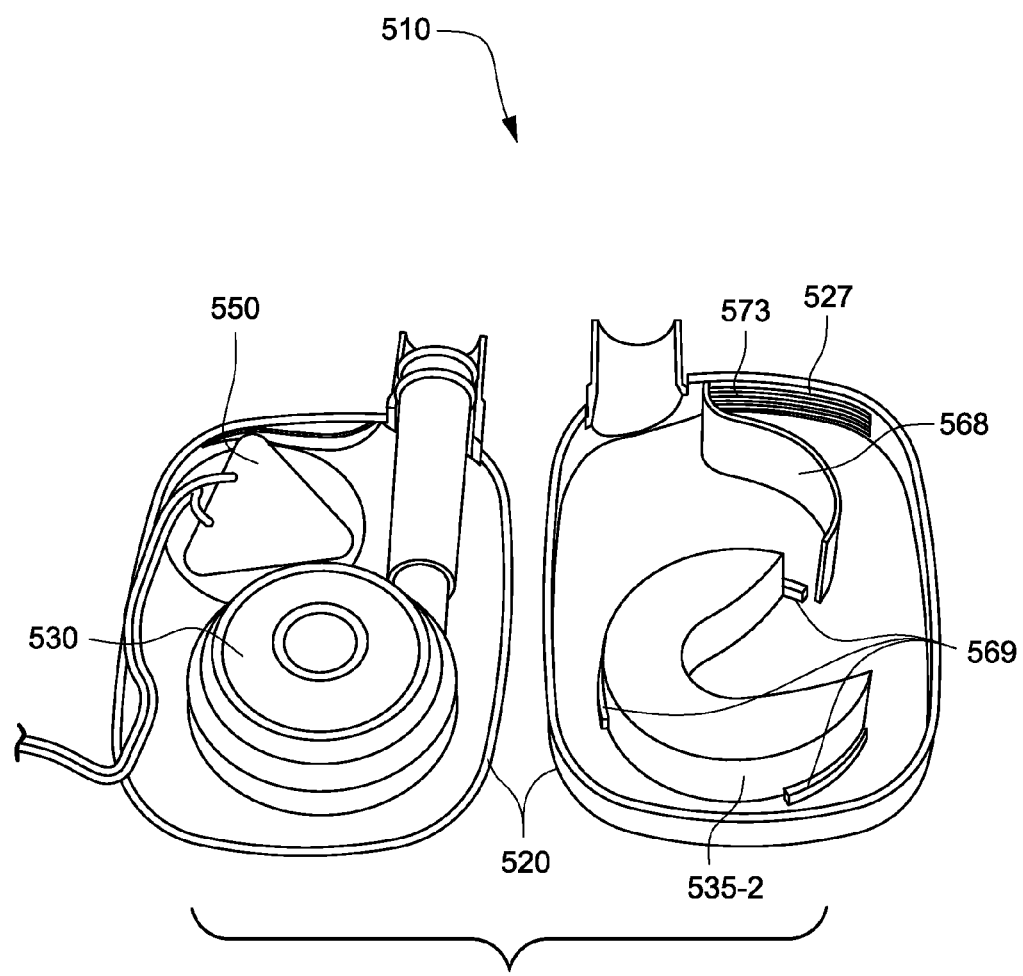
Figures 3, 27:
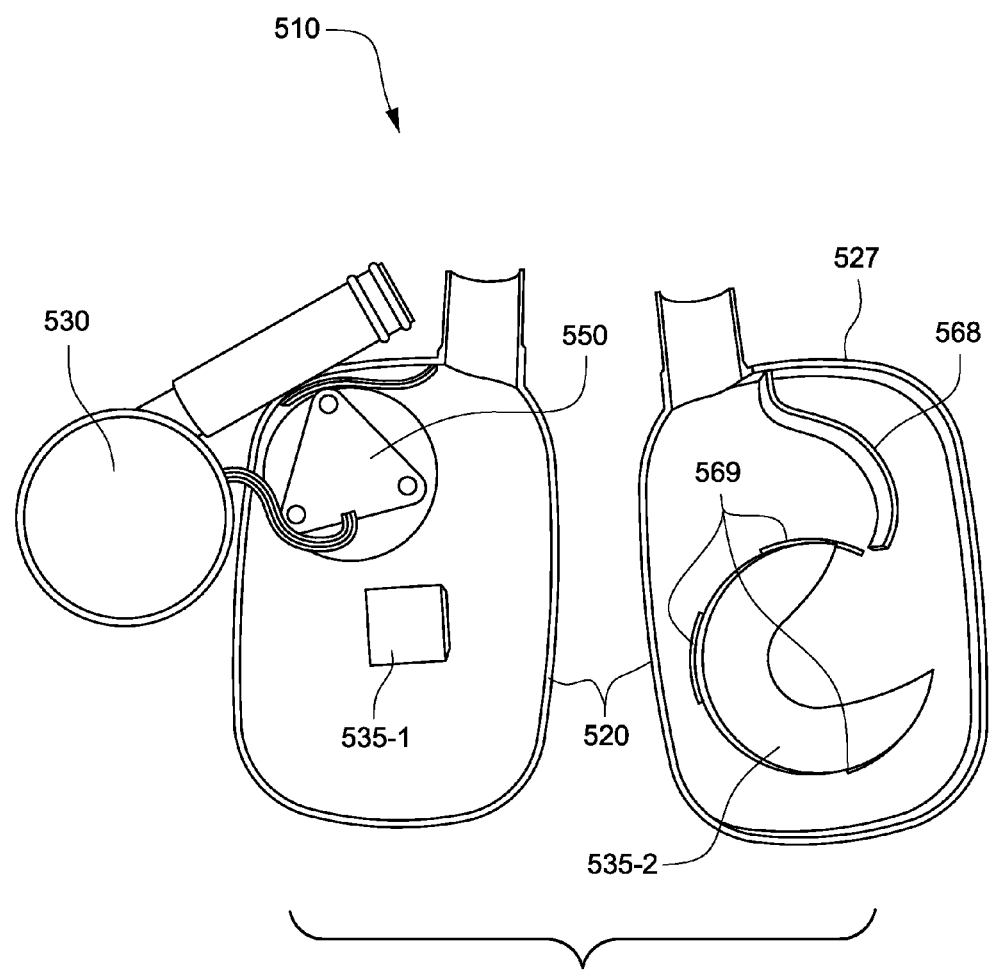

FIGS. 27-1 to 27-3 show a flow generator 510 (e.g., battery powered) according to another example of the present technology. In this example, a grate 573 is provided to the inlet 527 of the housing 520, e.g., to prevent access to the filter supported within the housing, prevent user's fingers from poking into the housing, and/or prevent large particles from be sucked into the housing through the inlet. A slight S-shaped sound baffle wall 568 is provided within the housing adjacent the inlet 527 to provide a noise barrier for the blower 530 and/or reflect noise from the blower 530 to prevent/reduce noise emitted back through the inlet 527. The sound baffle wall 568 also directs incoming airflow as sound waves are reflected or bounced back off the baffle wall. Curved blower baffle walls 569 are also provided to the housing and adapted to surround the blower 530 for guiding air to the blower inlet. One or more pieces of foam (e.g., silicone open cell foam) may be provided to support the blower 530 with the housing and provide sound absorption and suspension, e.g., pieces of foam block 535-2 to support the bottom of the blower and curved foam piece 535-1 to support the top of the blower and guide air to the blower inlet. The PCB 550 includes a triangular configuration and is supported within the housing adjacent the blower.

Figure 5:
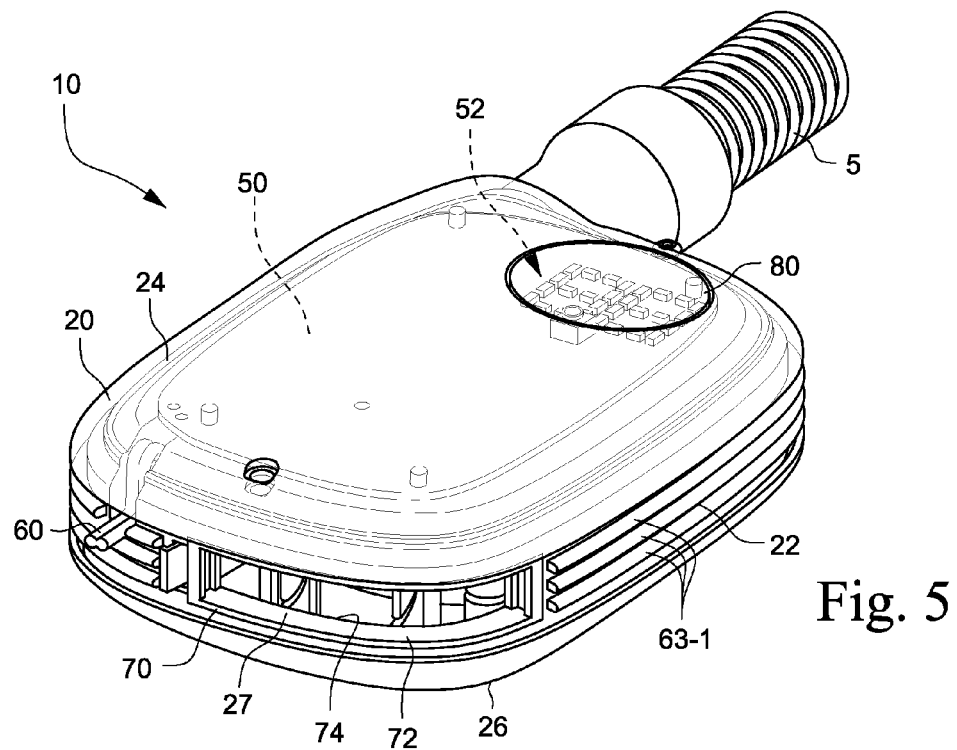
FIG. 5 is another perspective view of the flow generator of FIG. 1 with the top cover shown translucent.
Figures 1, 103:
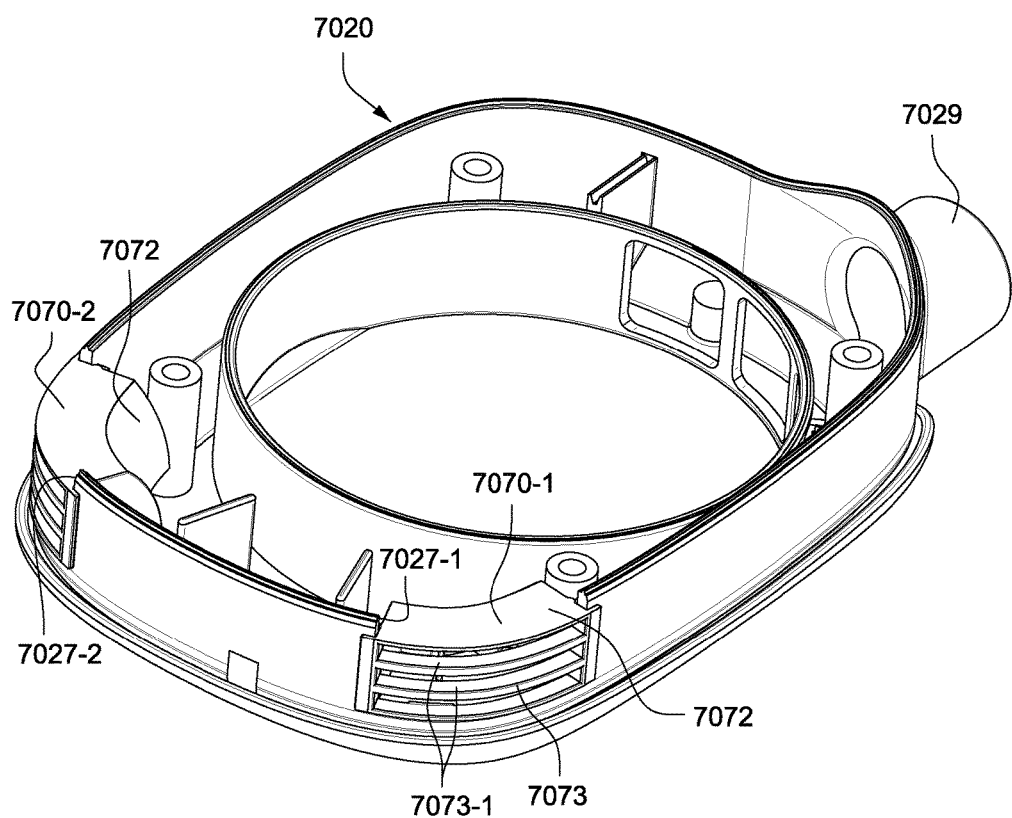
Figures 2, 103:
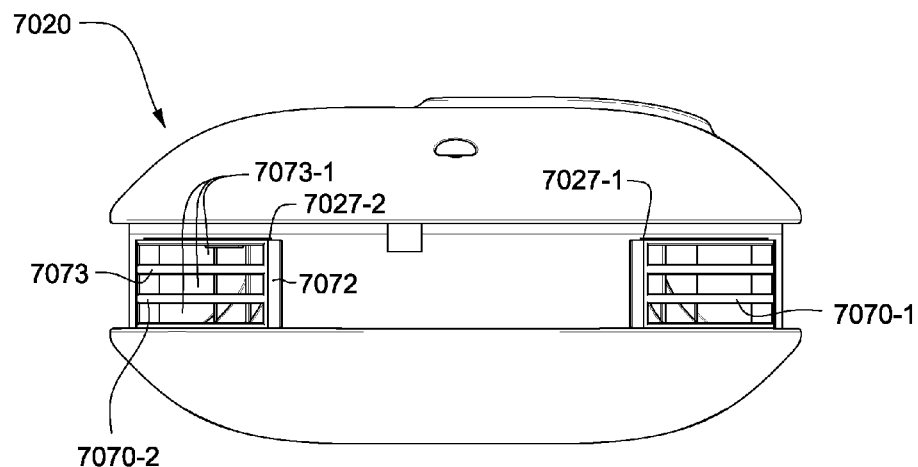
Figures 3, 103:
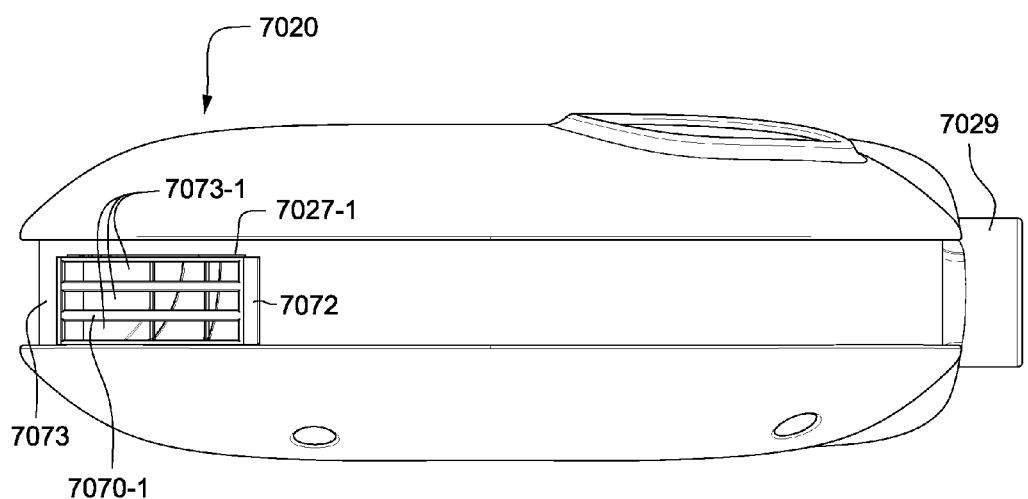
Figures 4, 103:
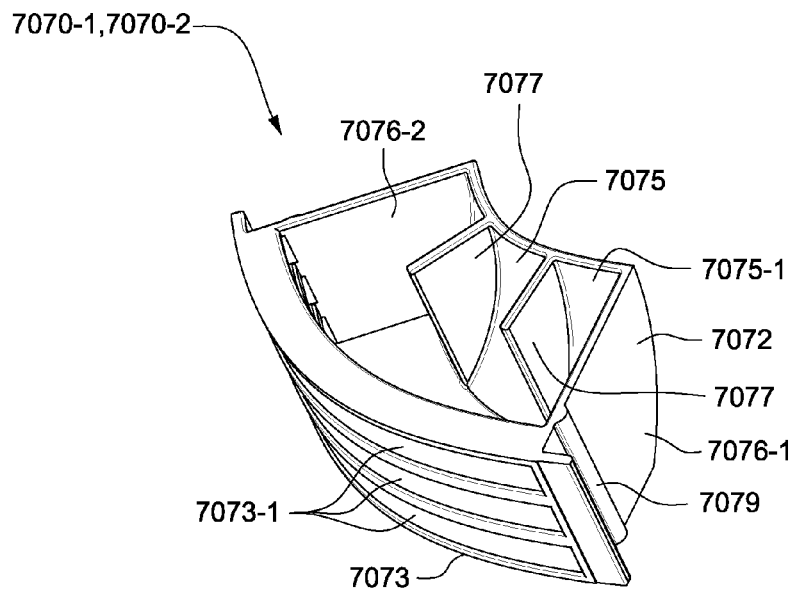
Figures 5, 103:
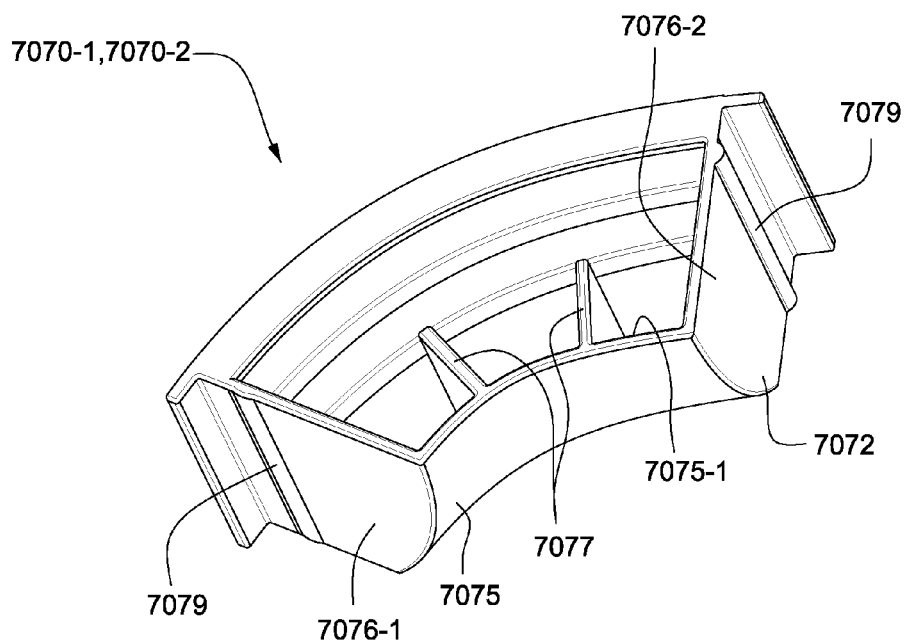

In an alternative example, as shown in FIGS. 103-1 to 103-5, the FG housing 7020 includes a air flow outlet 7029 and two air flow inlets, a first inlet 7027-1 and second inlet 7027-2 extending along respective corners of the housing opposite to the outlet 7029. Each of the first and second inlets 7027-1, 7027-2 receives or otherwise supports a respective first and second air filter 7070-1, 7070-2.

The dual inlet arrangement provides two air flow inlets, each of which is smaller (e.g., smaller length) than the single inlet of a single inlet arrangement, e.g., compared to air flow inlet in FIGS. 5 and 6. The smaller air flow inlet provides a smaller source for emitting noise from the blower.

Also, the two air flow inlets are located along opposite corners of the housing, which provides an arrangement to inhibit noise radiated from the blower, i.e., noise radiated from smaller air flow inlets along corners of the housing and not directly out a larger air flow inlet along a central wall section of the housing. In an example, acoustic noise radiated from the two air flow inlets may be lower at the low and mid frequencies (e.g., about 100-300 Hz and 700-1700 Hz) compared to a single inlet of the same total area.

In addition, the dual inlet arrangement provides two air flow inlets on opposite corners of the housing, which decreases the chance of the air flow inlet being blocked when in the bed, e.g., one of the air flow inlets may be operative even if the other air flow inlet is blocked (e.g., by bedding).

In an alternative example, the two air flow inlets may be located along opposite sides of the housing, rather than opposite corners. In an example, the two air flow inlets may be spaced at least 5-10 cm apart from another, e.g., at least 5 cm apart, at least 8 cm apart.

In an alternative example, the housing may provide a single elongated air flow inlet along a corner of the housing such that the air flow inlet extends along two adjacent sides of the housing. Such arrangement may decrease the chance of the air flow inlet being blocked when in the bed, e.g., a portion of the air flow inlet along one side of the housing may be operative even if the remaining portion of the air flow inlet on the adjacent side of the housing is blocked.

In the illustrated example, each of the first and second air filters 7070-1, 7070-2 is in the form of an air filter cartridge structured to be removable mounted within the respective first and second inlets 7027-1, 7027-2 of the FG housing 7020, e.g., to allow cleaning and/or replacement of the filter. As best shown in FIGS. 103-4 and 103-5, each of the first and second air filter cartridges 7070-1, 7070-2 includes a cartridge body 7072 that supports a filter to filter air drawn into the FG housing 7020 by the blower.

As illustrated, the cartridge body 7072 includes a grill-like front portion or grate 7073 including horizontally extending walls 7073 that define inlet openings 7073-1 into the air filter cartridge 7070-1, 7070-2, a rear portion with an arcuate-shaped filter air directing wall 7075, and end walls 7076-1, 7076-2 each including structure to retain the cartridge body within the inlet opening of the FG housing 7020. The arcuate-shaped air directing wall 7075 includes a generally concave surface 7075-1 along with a plurality of filter air directing vanes 7081 (e.g., 2 vanes illustrated however less than 2 vanes, such as 1 vanes, or more than 2 vanes, such as 3, 4, 5 or more are possible) to direct air flow. Further details of such arrangement along with exemplary filter media 6574 are described in further detail below with respect to the air filter 6570 shown in FIGS. 102-1 to 102-9.

In the illustrated example, each end wall 7076-1, 7076-2 of the cartridge body 7072 includes an elongated cartridge rib 7079 adapted to interlock or otherwise engage along respective sides of the inlet opening, e.g., with a snap fit. However, it should be appreciated that the air filter cartridge may be mounted within the inlet opening in other suitable manners, e.g., mounting arrangement shown in FIGS. 102-1 to 102-9.

Side Wall Ribs

In the illustrated example, see FIGS. 13-22, the side wall 63 includes one or more ribs 63-1 that extend around the perimeter of the side walls and/or the end walls or portions thereof, i.e., along side wall portions between the air flow inlet 27 and the air flow outlet 29. Such wall ribs 63-1 may help to reduce turbulence/high frequency noise during air intake through the air flow inlet. Also, such wall ribs 63-1 may be provided for aesthetics (e.g., allude to "folded" layers) and to hide or otherwise blend the air filter 70 at the air flow inlet 27 into the FG housing 20. Locating the air flow inlet 27 within the side wall ribs 63-1 decreases the risk of the air flow inlet being blocked when the flow generator 10 is located within the bed as the flow generator 10 is more likely to be positioned on one of the larger first cover 24 or second cover 26 surfaces when within the bed. More particularly, the air flow inlet may be located on one of the end surfaces of the FG housing 20.

Blower Chamber

As seen in FIGS. 9-22 a first blower chamber wall 65 is provided to the main chassis wall 62 and defines a portion of the blower chamber 25 configured to receive the blower. The first blower chamber wall 65 generally has an annular shape to hold the blower but the shape may vary to accommodate other shaped blowers. One or more apertures 65-1 are provided to the first blower chamber wall 65 (e.g., two, three, or more openings) to allow air to flow from the blower outlet 34 to the air flow outlet 29 of the FG housing 20. Top dividing walls 66 are provided on respective sides of the apertures 65-1 to direct or guide air towards the air flow outlet 29 (e.g., see FIGS. 14 and 22).

Air Flow Vanes

One or more inlet air flow vanes 68 are provided adjacent the air flow inlet 27 to direct or guide air towards the blower inlet 32. In the illustrated example, a pair of air flow vanes is provided, and each vane includes a generally curved or contoured profile. However, it should be appreciated that other suitable number of air flow vanes may be provided (e.g., 1, 3, 4 or more air flow vanes), and the air flow vanes may include other suitable shapes or profiles for directing flow. In use, the air flow vanes may pre-swirl the incoming air and may also assist in reducing radiated noise from the air flow inlet 27.

Wire Guide

The chassis also includes a support structure or wire guide 67 to route, guide or otherwise support power lead wire 60 for the power cord connection extending directly from the PCB 50 to outside the housing (e.g., see FIGS. 4, 6, 7, 10, 13, 14, and 22). Such arrangement helps to prevent a user from knocking out the cord, e.g. if flow generator 10 is used in the bed and user lies on the flow generator 10 during sleep.

The power lead wire or power cable 60 may be routed from the PCB 50 to outside the FG housing 20 in other suitable manners. For example, FIGS. 96 to 100 show alternative arrangements for routing the power lead wire 60, e.g., on centerline between top and bottom cover (FIG. 96), offset towards the top cover (FIGS. 97 to 100).

PCB Support

The exterior side 62-2 of the main chassis wall 62 is structured to support the PCB 50 outside the chassis interior and outside the air flow path. As best shown in FIGS. 3, 4, 6, 7, 10, and 13, a plurality of pegs (e.g., 3, 4, or more pegs) are provided to the chassis wall and adapted to engage within respective openings provided to the PCB 50 to support and align the PCB on the chassis wall. In an example, the pegs may be arranged to allow only one possible mounting position of the PCB on the chassis wall.

Also, as shown in FIGS. 4, 7, 13, and 17, an opening 62-3 is provided through the main chassis wall 62 to allow magnet wire 59 from the blower 30 within the chassis interior to be directly connected to the PCB 50, i.e., rather than using lead wires. This arrangement may reduce costs and is facilitated by the short distance between the blower 30 and PCB 50.

Figure 88:
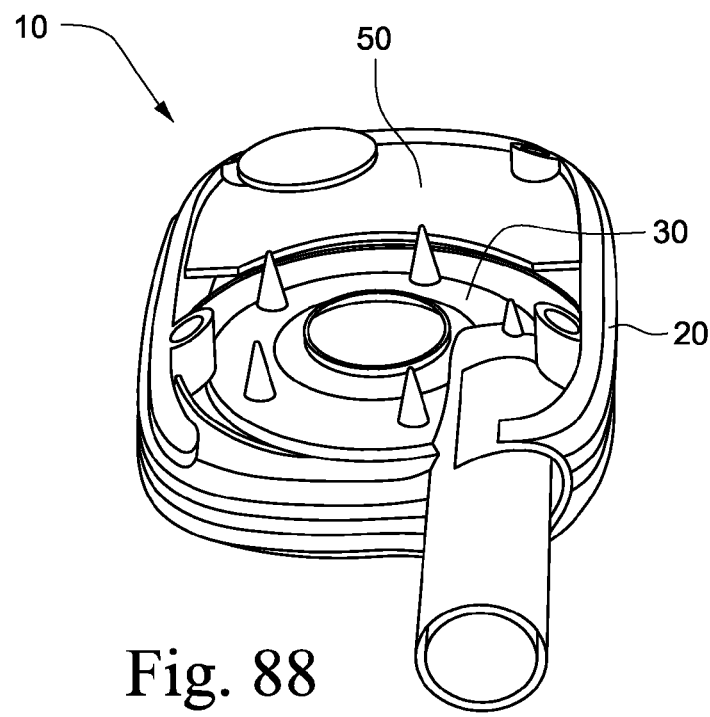
FIGS. 88 to 91 show alternative shapes and positions of a PCB for a flow generator according to alternative examples of the present technology.
Figure 89:
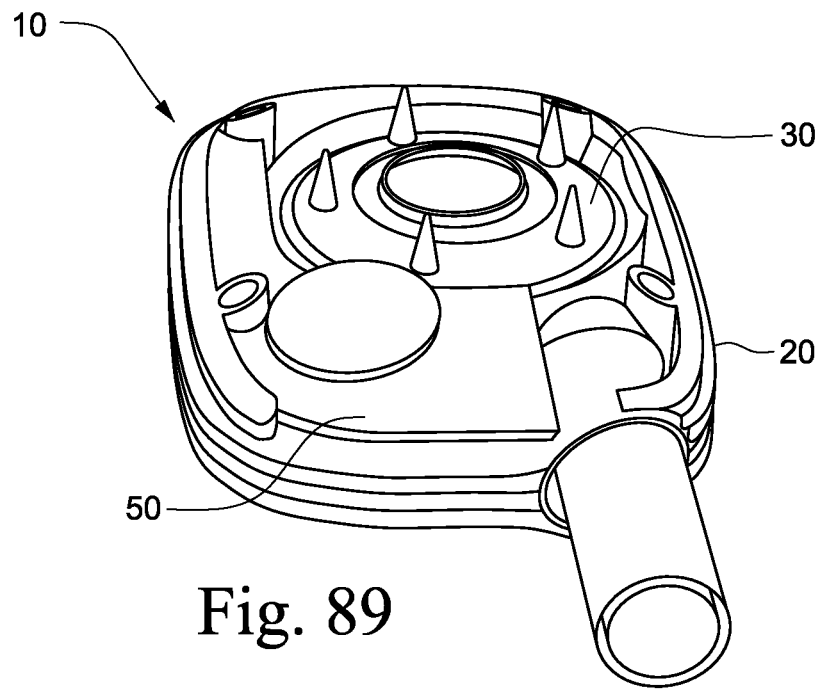
Figure 90:
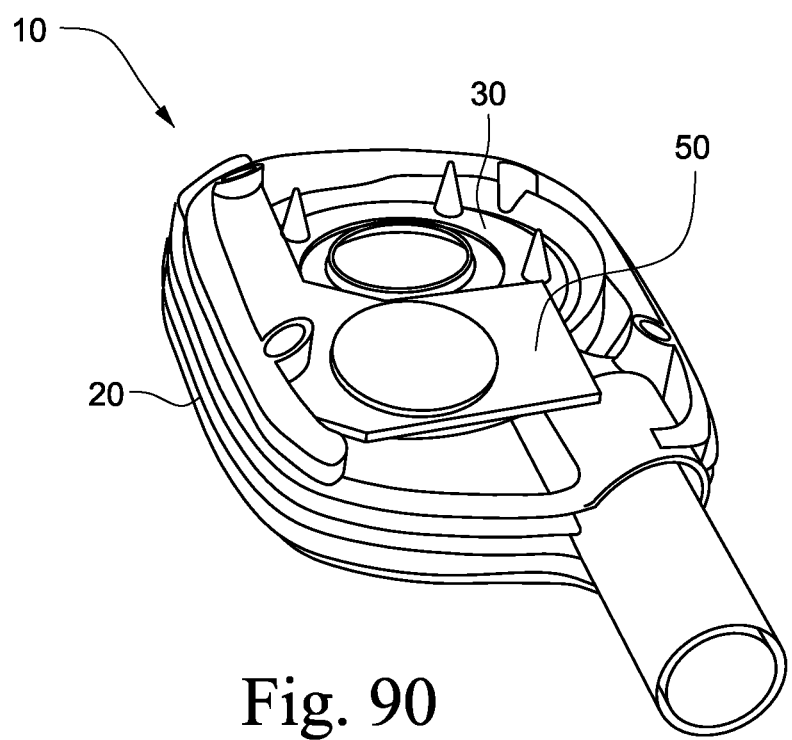
Figure 91:
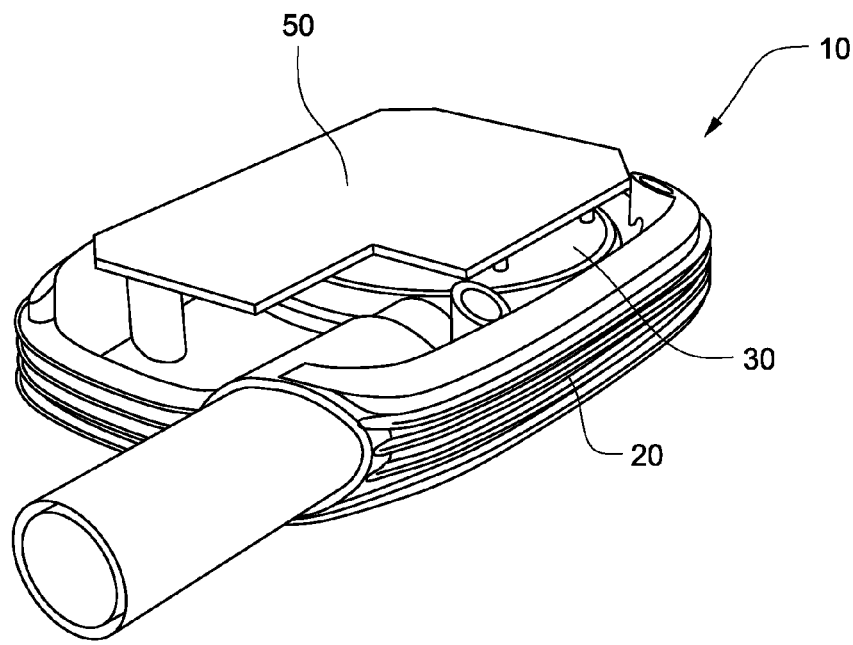

The PCB 50 may include alternative shapes and may be provided to the FG housing 20 in other suitable positions with respect to the FG housing 20 and/or blower 30. For example, FIG. 88 shows PCB 50 supported horizontally along a rear portion of the housing 20 and blower 30, FIG. 89 shows an L-shaped PCB 50 supported horizontally along a side and front portion of the FG housing 20 and blower 30, FIG. 90 shows an arrangement similar to FIG. 89 with the PCB 50 supported at an angle with respect to horizontal, and FIG. 91 shows PCB 50 supported horizontally above or over the blower 30. The shape and/or positioning of the PCB 50 may be selected in view of air inlet area, display positioning, display aesthetics, space for noise dampening, microphone/button positioning, housing thickness, cable exit, and/or heat dissipation, for example.

In an example, the flow generator 10 of FIG. 88 may have a length of about 120-140 mm (e.g., 129 mm), a width of about 80-100 mm (e.g., 91 mm), and a height of about 30-50 mm (e.g., 43 mm). In an example, the flow generator 10 of FIG. 89 may have a length of about 130-150 mm (e.g., 140 mm), a width of about 90-110 mm (e.g., 102 mm), and a height of about 30-50 mm (e.g., 43 mm). In an example, the flow generator 10 of FIG. 90 may have a length of about 120-140 mm (e.g., 129 mm), a width of about 80-100 mm (e.g., 93 mm), and a height of about 40-60 mm (e.g., 48 mm). In an example, the flow generator 10 of FIG. 91 may have a length of about 130-150 mm (e.g., 139 mm), a width of about 90-110 mm (e.g., 102 mm), and a height of about 40-60 mm (e.g., 50 mm). However, it should be appreciated that other suitable dimensions are possible.

2.1.2 Top Cover

The top cover 24 is secured to the chassis 22 to enclose the PCB 50 within the FG housing 20. One or more fastener openings 24-1 (e.g., see FIG. 1) are provided in the top cover to receive fasteners that engage respective fastener receptacles 69-2 (e.g., see FIGS. 10 and 13) provided to the chassis 22 to secure the top cover 24 to the chassis 22. However, the top cover 24 may be secured to the chassis 22 in other suitable manners.

Figure 33:
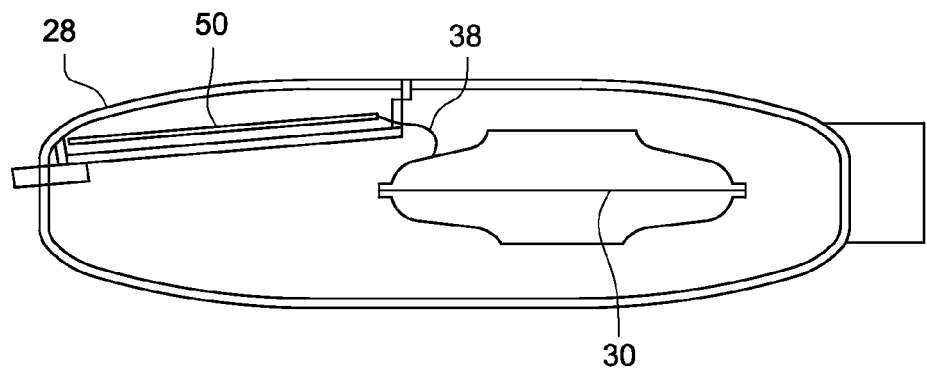
FIG. 33 shows a flow generator including a housing with a hood according to an example of the present technology.

In an alternative example, as shown in FIG. 33, the top cover 24 may include a PCB hood or removable portion 28 provided to the top cover 24 that may be opened to allow access to the PCB 50. FIG. 33 also shows blower lead wire 38 passing from the blower 30 to the PCB 50.

Interface Button

An interface button 80 is provided to the top cover 24 and adapted to align with a display 52 (e.g., numeric display) provided to the PCB 50. The button 80 may be translucent, clear, or otherwise structured to allow the display 52 to be visible through the button 80. Preferably, the interface button 80 is recessed in the top cover 24 or is surrounded by a button rim (e.g. see rim 6580-1 in FIGS. 101-1 and 101-3) to reduce the chance of inadvertent pressing of the button 80 if the device were located within the bed for use, for example to prevent the button 80 being pressed should the user roll onto the device in the bed in use. Furthermore, the interface button 80 may require a "double-click" deactivation and/or activation function to ensure the user must intentionally deactivate and/or activate the device to prevent accidental deactivation and/or activation of the device in use. The "double-click" may be required within a limited time period, such as less than 1, 2 or 3 seconds.

Figure 20:
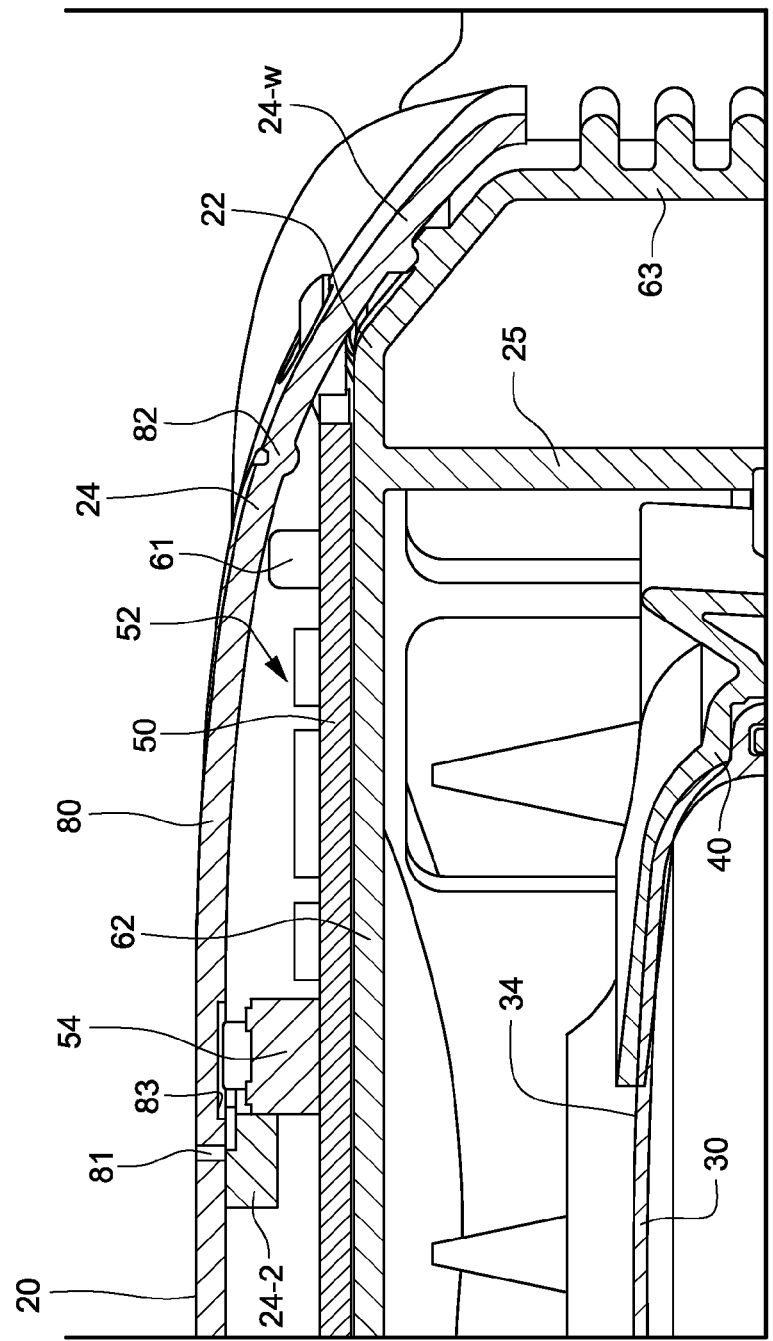
Figure 21:
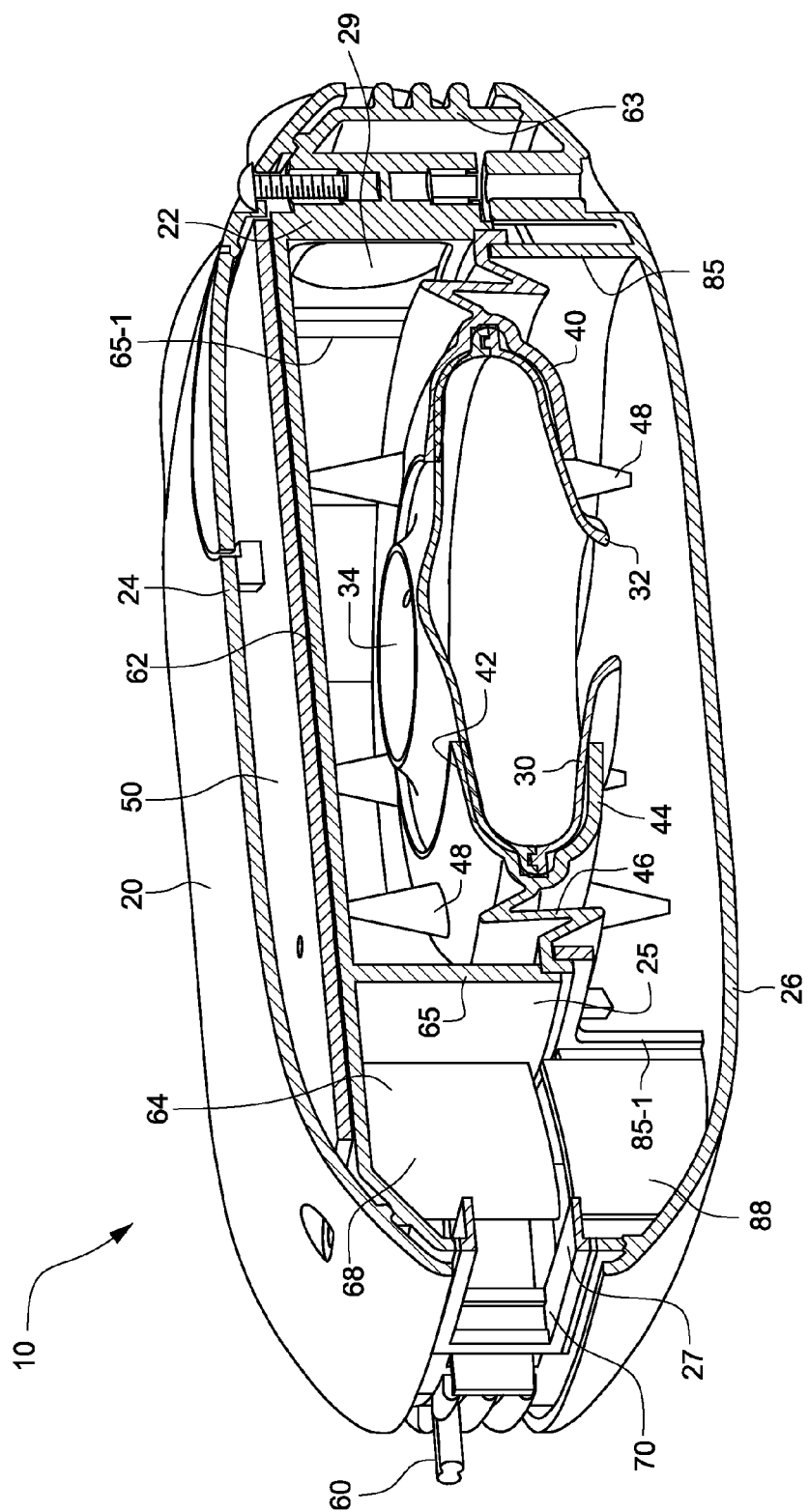

As best shown in FIG. 20, the button 80 is movably mounted to a top cover wall 24-*w* of the top cover 24 to allow the button to activate a switch 54 provided to the PCB 50. A gap 81 is provided between the button and the top cover wall 24-*w*, and a living hinge 82 interconnects the button 80 with the top cover wall 24-*w*, which arrangement allows the button 80 to flex with respect top cover wall 24-*w*. A stop structure 24-2 is provided to the top cover wall 24-*w* to provide a hard stop and limit the range of movement of the button 80 in use. In use, the button 80 may be depressed to activate the switch 54 provided underneath the button 80. A groove 83 may be provided to the underside of the button 80 to receive and align the switch 54 with the button 80.

Figures 1, 48:
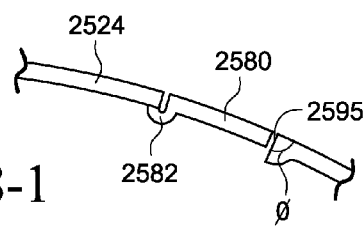
Figures 2, 48:
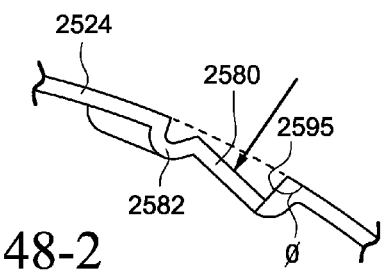

However, it should be appreciated that the interface button 80 may be movably mounted or otherwise provided to the top cover 24 in other suitable arrangements. For example, FIGS. 48-1 and 48-2 show another example of a button 2580 movably mounted to the top cover 2524 by a living hinge 2582. In this example, the opening in the top cover 2524 adjacent the free end of the button opposite the living hinge 2582 includes a tapered surface 2595 (e.g., $\Phi > 90°$). The tapered surface 2595 allows movement of the button 2580 but also provides a stop to prevent further deflection, i.e., tapered surface allows travel of the button 2580 up to a certain distance at which point the free end of the button 2580 contacts the tapered surface 2595 to prevent further deflection.

Figure 49:
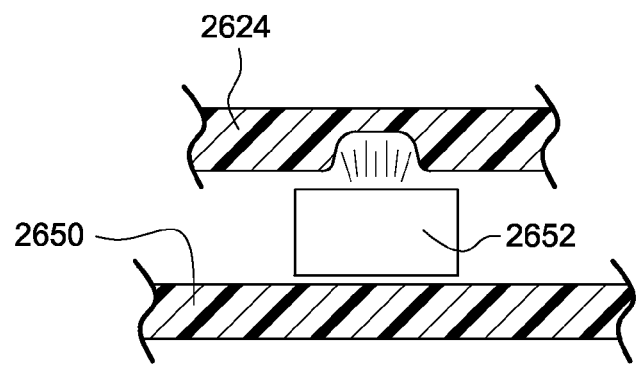

FIG. 49 shows an example in which the top cover 2624 is spaced sufficiently away from the PCB 2650 to accommodate display 2652 provided to a center of the PCB 2650. As illustrated, the top cover 2624 may include a thinned cross-section to allow display to shine therethrough.

Figure 50:
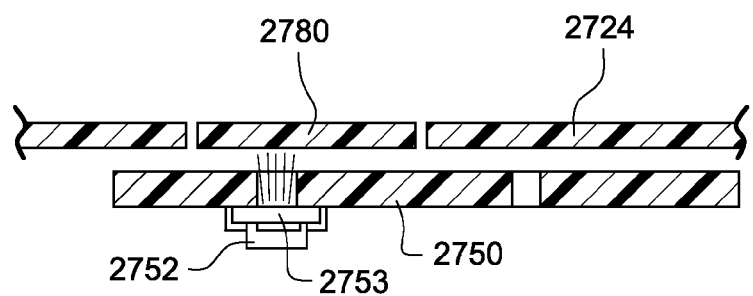

FIG. 50 shows an example in which the PCB 2750 includes a display 2752 in the form of an LED array 2753. In the illustrated example, the LED array 2753 may be mounted to rear of the PCB with the PCB including an opening to allow the LED array 2753 to shine through to the button 2780 on the top cover 2724.

Figure 51:
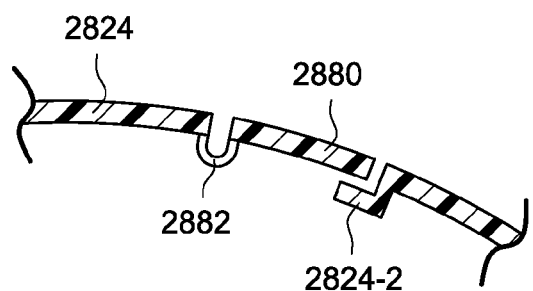

FIG. 51 shows another example of a button 2880 movably mounted to the top cover 2824 by a living hinge 2882. In this example, the opening in the cover adjacent the free end of the button opposite the hinge includes a stop structure 2824-2 to prevent further deflection of the button. In an example, the stop structure may be positioned to allow the button about 0.2-0.3 mm, e.g., 0.25 mm, of travel.

Figures 1, 52:
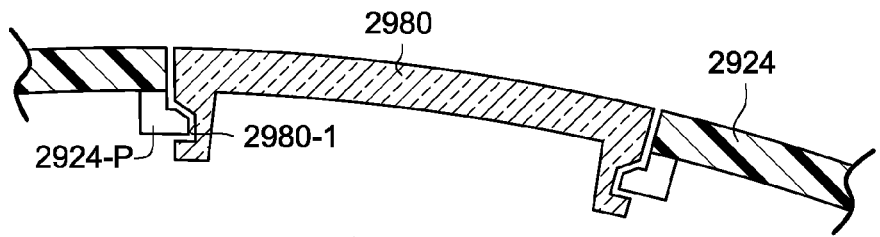
Figures 2, 52:
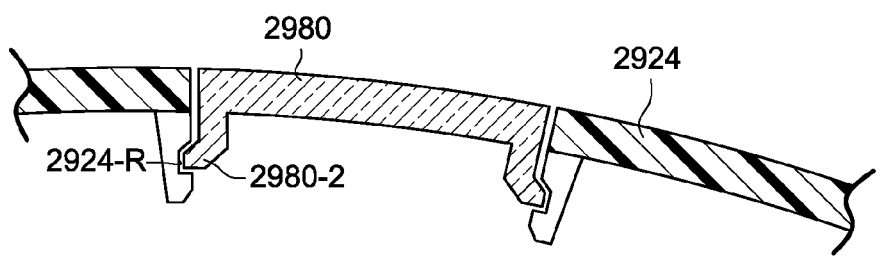

FIGS. 52-1 and 52-2 show another example of a button 2980 provided within an opening in the top cover 2924. In FIG. 52-1, the button includes a button recess 2980-1 along its perimeter adapted to receive a cover protrusion 2924-P extending from the opening in the top cover. In an alternative example, as shown in FIG. 52-2, the button 2980 includes a button protrusion 2980-2 along its perimeter adapted to engage within a cover recess 2924-R provided to the opening in the top cover. The button recess 2980-1 and the cover recess 2924-R provided to the button and top cover opening respectively are sufficiently wide to provide the button 2980 with a range of movement.

Figure 84:
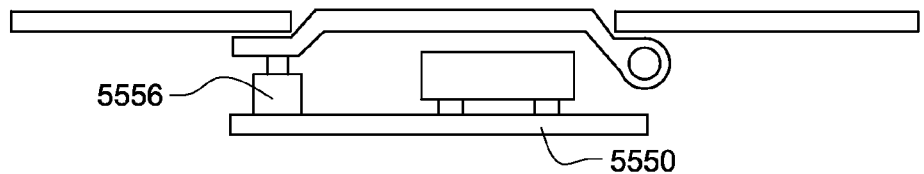
FIGS. 84 to 86 show alternative examples for activating features provided on the PCB of a flow generator according to alternative examples of the present technology.
Figure 85:
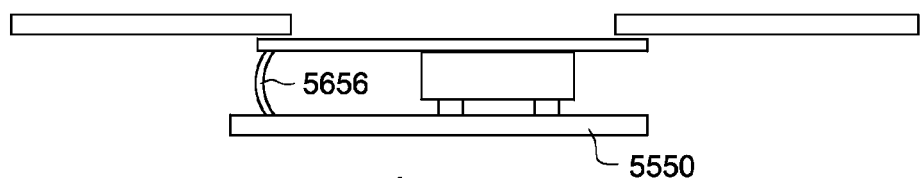
Figure 86:
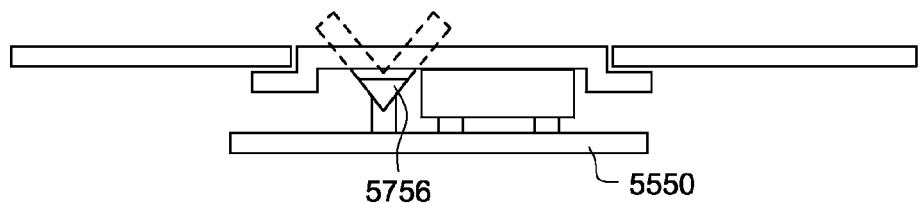

FIGS. 84 to 86 illustrate alternative examples for activating features 5556 provided by the PCB 5550, e.g., micro-switch 5556 (FIG. 84), resistive film 5656 (FIG. 85), or capacitive sensor 5756 (FIG. 86).

2.1.3 Bottom Cover

The bottom cover 26 is secured to the chassis 22 to enclose the chassis interior 62-1 and support and retain the blower 30 within the chassis interior 62-1. One or more fastener openings 26-1 (e.g., see FIGS. 8 and 12) are provided in the bottom cover 26 to receive fasteners that engage respective fastener receptacles 69-1 (e.g., see FIGS. 9 and 14) provided within the chassis interior to secure the bottom cover 26 to the chassis 22. However, the bottom cover 26 may be secured to the chassis in other suitable manners.

The bottom cover 26 includes a second blower chamber wall 85 that defines a portion of the blower chamber 25 configured to receive the blower 30. The second blower chamber wall 65 generally has an annular shape to hold the blower 30 but the shape may vary to accommodate other shaped blowers. The first and second blower chamber walls 65, 85 of the chassis 22 and bottom cover 26 cooperate and align to define the blower chamber 25. The second blower chamber wall 85 of the bottom cover 26 includes one or more openings 85-1 to allow air to flow from the air flow inlet 27 of the FG housing 20 to the blower inlet 32.

The bottom cover 26 includes bottom dividing walls 86 (e.g., see FIG. 12) that cooperate and align with the top dividing walls 66 of the chassis 22 to direct or guide air towards the air flow outlet 29. Also, the bottom cover 26 includes one or more bottom air flow vanes 88 that cooperate and align with the inlet air flow vanes 68 of the chassis 22 to direct or guide air through the openings 85-1 in the blower chamber wall 85 and towards the blower inlet 32.

2.2 Suspension Device

The suspension device 40 (e.g., constructed of elastomer material such as silicone) is supported or otherwise captured within the blower chamber 25 between the chassis 22 and bottom cover 26 (see FIGS. 9, 11, 15-22). The suspension device 40 keeps the blower 30 out of contact with the FG housing 20 and allows movement of the blower 30 with respect to the FG housing 20 in use, e.g., acts like a spring to isolate vibration. The blower 30 is nested within the suspension device 40, which retains and supports the blower 30 to allow operation of the flow generator 10 in any orientation. Preferably, the suspension device 40 has a substantially symmetrical shape to assist in allowing the flow generator 10 to operate in any orientation. In addition, the suspension device 40 acts as a pressure seal between low and high pressure sides of the blower 30.

As illustrated, the suspension device 40 includes an overall exterior shape that substantially matches the shape of the blower 30, i.e., a generally cylindrical shape or disk shaped. However, the suspension device may include other suitable shapes that may not correspond to the blower 30 shape, e.g., suspension device includes shape corresponding to shape of housing or chassis interior. The suspension device 40 surrounds the blower 30 to substantially enclose or encase the blower without blocking the blower inlet 32 or blower outlet 34. The suspension device 40 may include clearances around the blower inlet 32, blower outlet 34 and the adjacent walls of the blower, for example clearances of about 1 mm to about 20 mm, e.g., about 5 mm, about 10 mm, or about 15 mm. However, it is to be understood that clearances of other sizes may be used.

Figure 18:
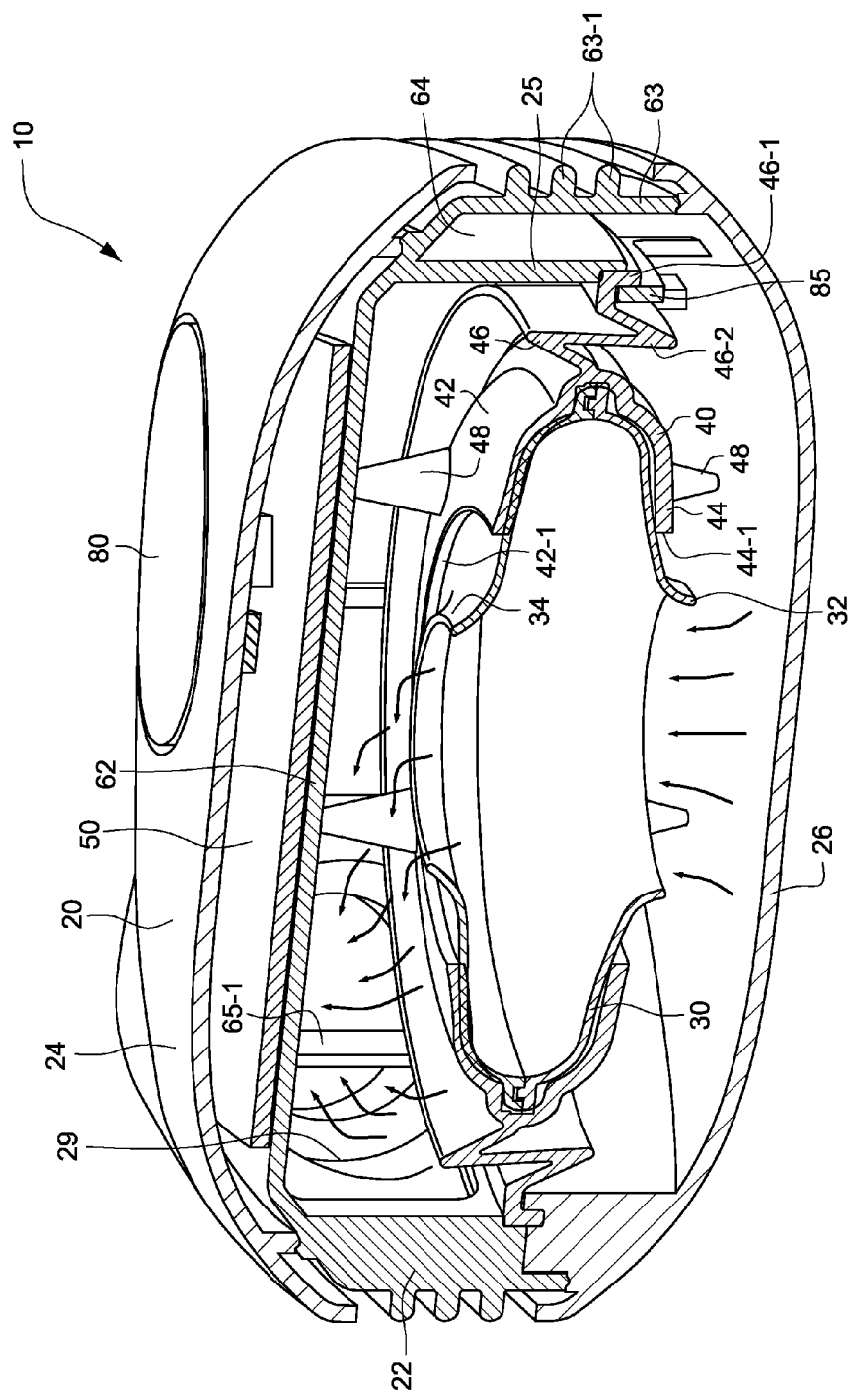
Figure 19:
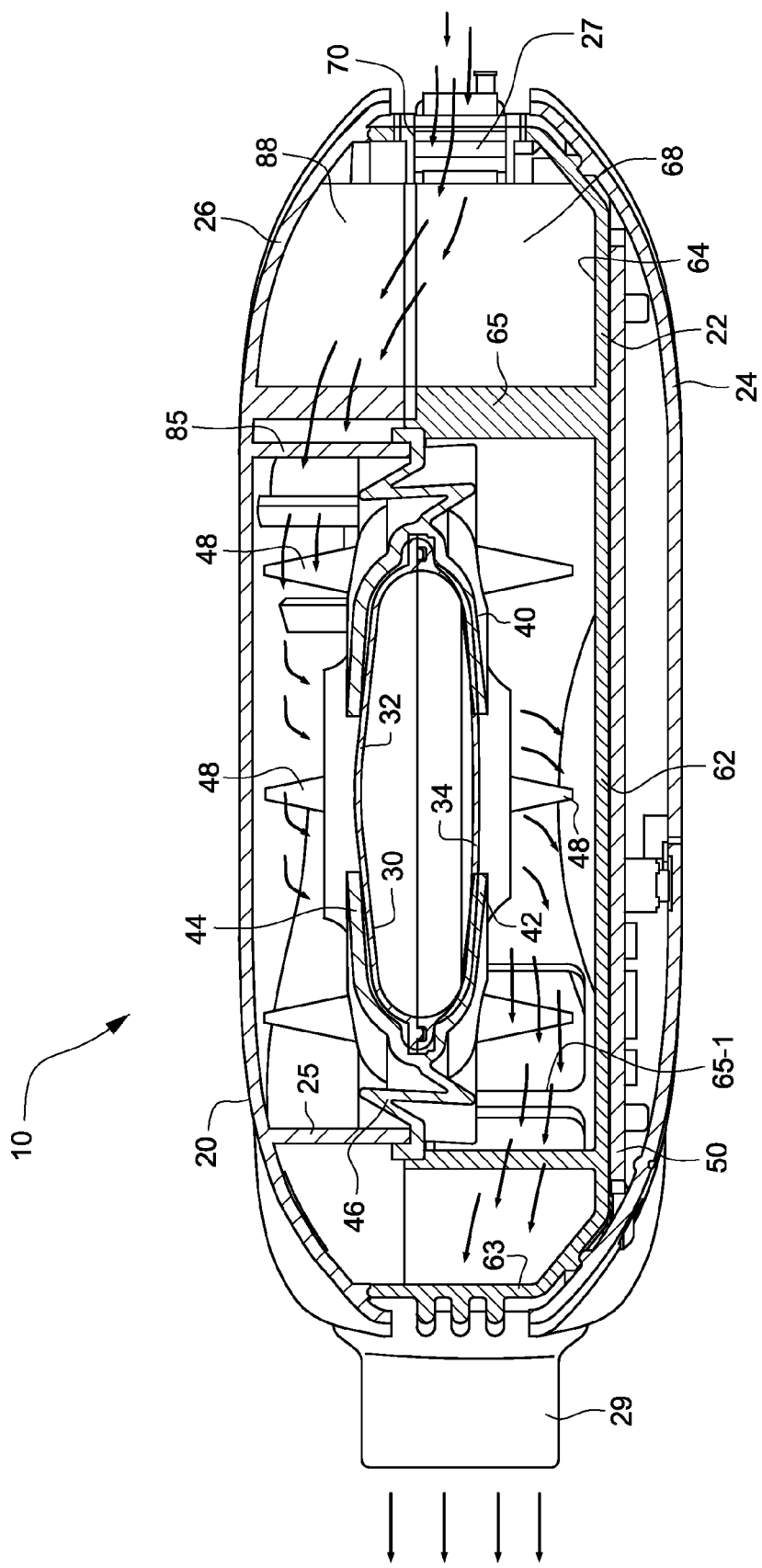

As illustrated in FIG. 18, the suspension device 40 includes opposing suspension walls 42, 44 that support the blower therebetween and an annular support member 46 extending from the suspension walls 42, 44. The support member 46 has a support end portion 46-1 sandwiched or otherwise supported between the first blower chamber wall 65 of the chassis 22 and second blower chamber walls 85 of the bottom cover 26 defining the blower chamber 25. The support member 46 also includes a generally S-shaped or bellows-like support portion 46-2 between the support end portion 46-1 and the suspension walls 42, 44 structured to resiliently support the blower 30 within the FG housing 20 and absorb shock applied to sides of the FG housing 20 as well as top and bottom of the housing, e.g., absorb impact shock applied both axially and radially. Suspension apertures 42-1, 44-1 are provided to respective walls 42, 44 to accommodate the blower inlet 32 and blower outlet 34 of the blower 30.

In addition, each suspension wall 42, 44 includes multiple flexible feet, pegs, or cones 48 (e.g., 3, 4, 5, or more cones) adapted to extend towards upper and lower walls of the chassis interior 62-1 and act as shock absorbers to absorb shock applied to top and bottom of the FG housing 30, e.g., absorb impact shock applied axially. In an example, the pegs or cones 48 may not be in contact with adjacent walls at all times, i.e., only during shock. The pegs or cones 48 may be relatively sharp or pointed to reduce stiffness. The pegs or cones 48 are arranged concentrically, however other cone arrangements are possible.

In an example, one or more suspension slits 49 (e.g., 3 slits) may be provided to at least one of the walls to facilitate assembly of the blower 30 within the suspension device 40 between the opposing suspension walls 42, 44 (e.g., see FIG. 9). Each suspension slit 49 may extend radially from the opening in the suspension wall 42, 44, however other suitable suspension slit arrangements are possible.

The support device 40 (also referred to as a divider seal) suspends/supports the blower 30 in the FG housing 20 and divides or seals the inlet side 32 of the blower from the outlet side 34 of the blower (i.e., divides or separates low and high pressure sides), e.g., to avoid the need for a connection tube that directs flow towards the outlet of the housing.

The support device 40 provides an arrangement that avoids the need for inlet and outlet seals adjacent the blower inlet 32 and blower outlet 34 of the blower. In addition, the support device is constructed of an elastomeric material that isolates (e.g., vibration isolated) and/or serves as a suspension between the blower 30 and the FG housing 20. The annular support member 46 and multiple pegs or cones 48 provided to the top, bottom, and sides of the blower 30 support the blower 30 within the FG housing 20 so that the FG housing 20 and the blower 30 may be oriented in any direction, e.g., FG housing 20 may be positioned on its side rather than vertically.

In an example, the suspension device 40 (e.g., constructed of silicone) is sufficiently stiff to maintain structural integrity and shock resistance and sufficiently compliant to produce a low resonant frequency to isolate vibration (e.g., resonant frequency for the blower in suspension device may be between about 20-80 Hz, e.g., 25-40 Hz).

In an alternative example, the suspension device 40 may provide one or more flow passages for directing air through the FG housing 20, e.g., in addition to and/or in lieu of flow passages provided by the FG housing 20. Such silicone flow passages provided by the suspension device 40 may provide vibration and sound isolation.

Housing Seal and Exterior Grip

Figures 1, 24:
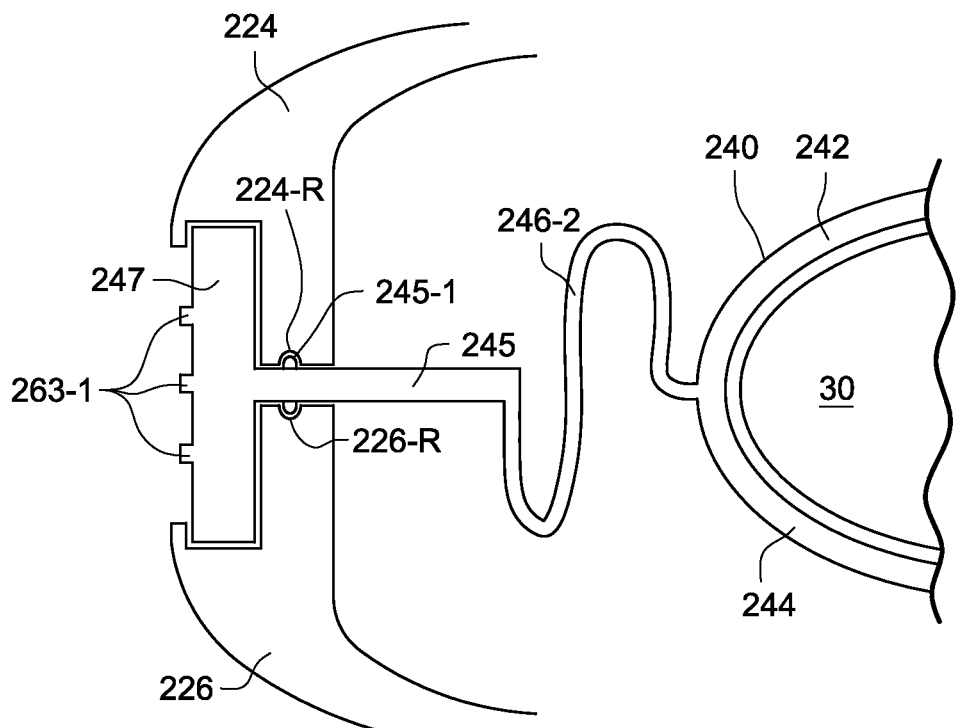
Figures 2, 24:
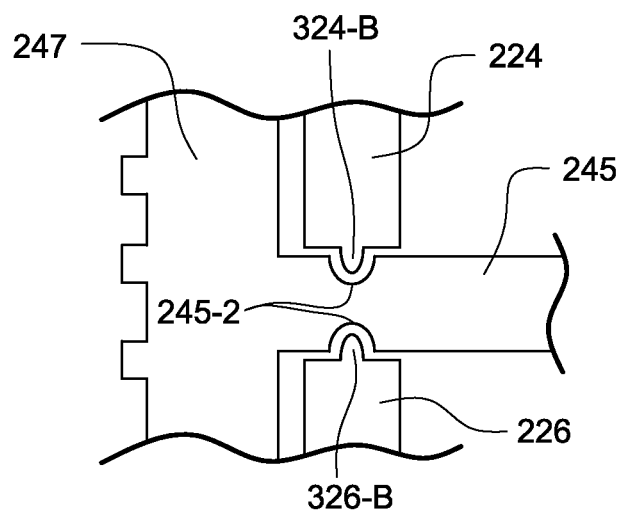

In an example, as shown in FIG. 24-1, the suspension device 40 may include a portion adapted to extend outside the FG housing 20 and along a side wall of the FG housing 20 to provide an exterior decorative detail to the FG housing 20 as well as provide grip to the FG housing 20 when holding the device, e.g., to prevent slipping.

In the illustrated example, the suspension device 240 (e.g., made from silicone which may be clear or colored) includes opposing suspension walls 242, 244 supporting blower 30, an S-shaped or bellows-like suspension portion 246-2 to absorb shock, suspension support member 245, and suspension exterior portion 247.

The suspension support member 245 is sandwiched between top and bottom housing parts 224, 226 (e.g., constructed of plastic) and includes a suspension bead detail or opposing suspension beads 245-1 adapted to engage within corresponding housing recesses 224-R, 226-R in the housing parts 224, 226. In an alternative example, as shown in FIG. 24-2, the suspension support member 245 may include opposing suspension recesses 245-2 adapted to engage respective beads or bead detail 224-B, 226-B provided to the housing parts 224, 226. The bead detail provides a seal between the housing parts to prevent air from leaking out of the housing. However, it should be appreciated that other suitable structures may be provided to the suspension support member to provide a seal between the housing parts. In addition, the suspension device provides a seal between low and high pressure sides of the blower as described above.

The silicone suspension exterior portion 247 along the side wall of the FG housing 220 includes one or more wall ribs 263-1. As described above, such wall ribs along the housing side wall may be provided for aesthetics and to hide or otherwise blend the air filter at the inlet opening into the housing. In addition, such silicone suspension exterior portion 247 with its silicone wall ribs 263-1 provide grip to the FG housing 220 when handling the device.

2.3 Air Filter

In the illustrated example, the air filter 70 may be in the form of an air filter cartridge structured to be removable mounted within the air flow inlet 27 of the FG housing 20, e.g., to allow cleaning and/or replacement of the filter. The air filter cartridge 70 includes a cartridge body 72 that supports a filter media 74 to filter air drawn into the FG housing 20 by the blower 30.

Figure 22:
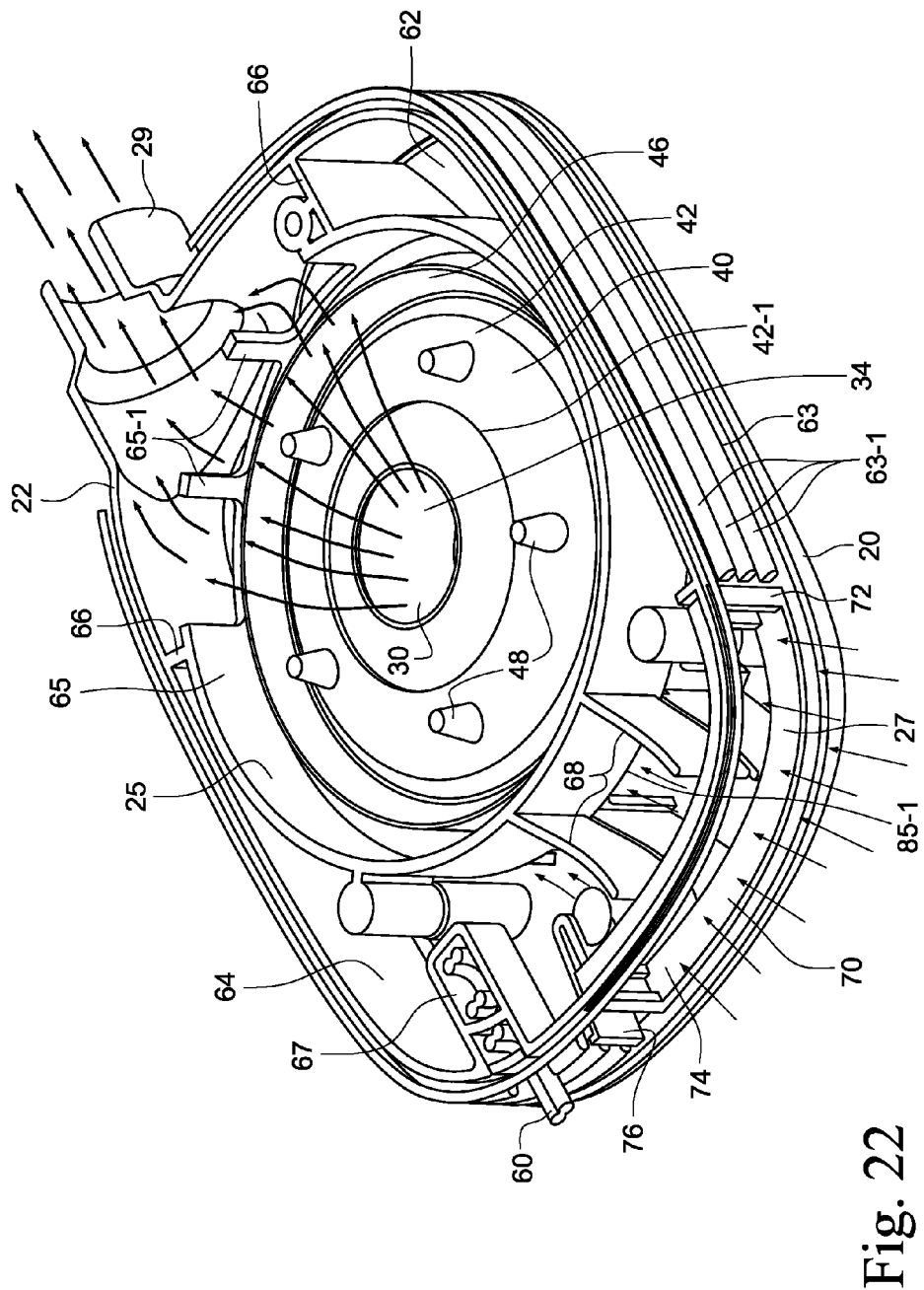

As best shown in FIGS. 9 and 22, one end of the cartridge body 72 includes a resilient clip portion 76 adapted to engage the side wall surrounding the air flow inlet 27 with a snap fit. In use, the end of the air filter cartridge 70 opposite the clip portion 76 is interlock or otherwise engaged within the air flow inlet 27 and then pivoted into the air flow inlet 27 until the clip portion 76 resiliently deflects into engagement with the FG housing 20, and a locking portion or shoulder provided to the clip portion 76 reaches a locking position with respect to the housing side wall adjacent the air flow inlet 27.

Figures 1, 92:
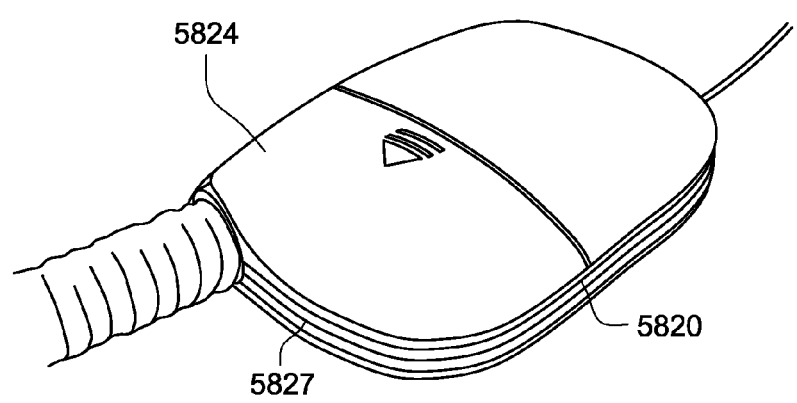
Figures 2, 92:
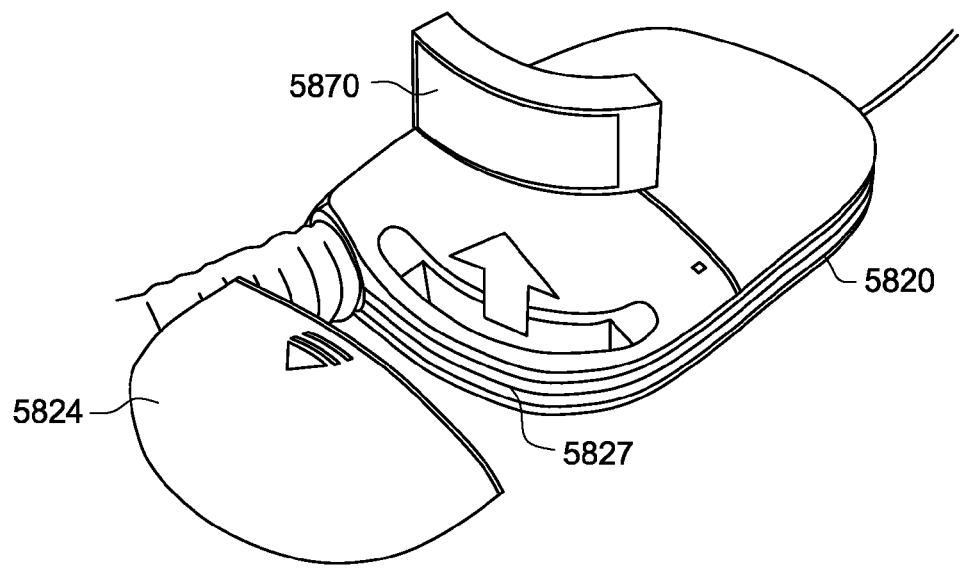

The air filter 70 may be mounted or otherwise provided to the flow generator 10 adjacent the air flow inlet 27 of the FG housing 20 in other suitable manners. For example, FIGS. 92-1 and 92-2 shows a FG housing 5820 with a slidably removable top cover 5824 to expose a slot that releasably supports an air filter 5870 adjacent the air flow inlet 5827. Because the air filter 70 is completely hidden, it may be made of relatively inexpensive materials.

Figures 1, 93:
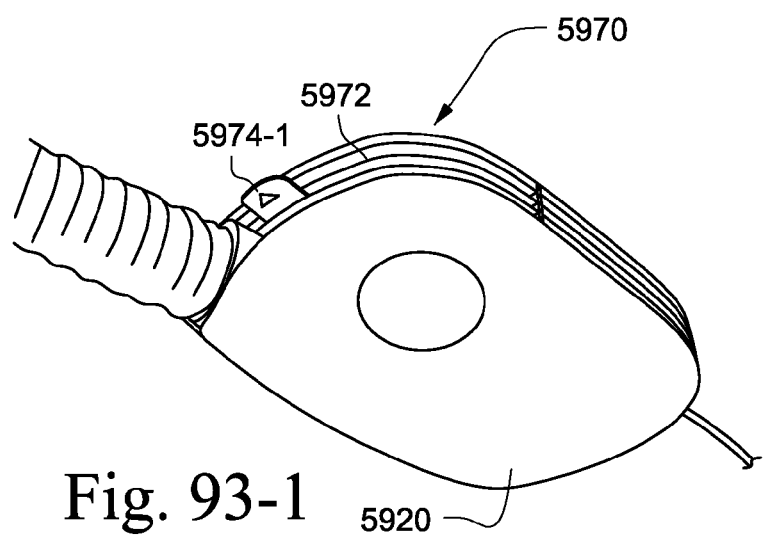
Figures 2, 93:
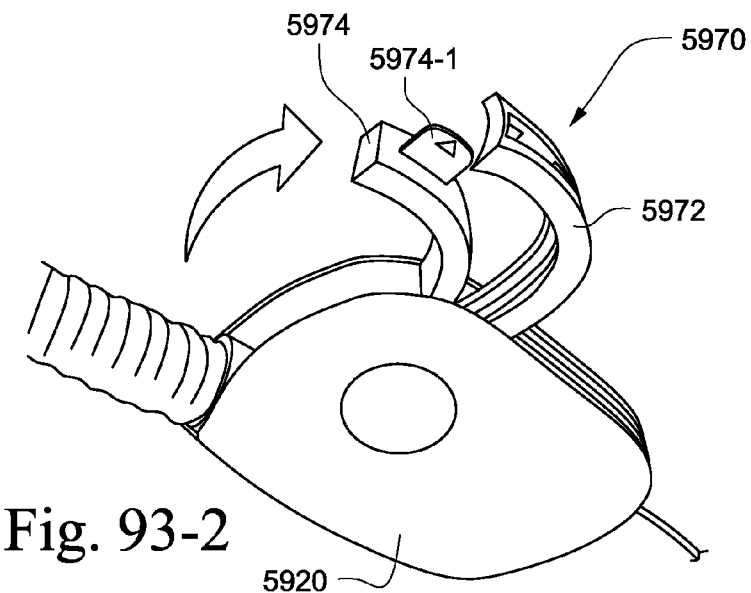

FIGS. 93-1 and 93-2 show an air filter 5970 arrangement including a filter media 5974 and a cartridge body 5972 having a pivotal door structure to enclose the filter media within the FG housing 5920. The filter media 5974 includes a filter pull-tab 5974-1 that protrudes through the door structure to allow the user to pull the filter pull-tab 5974-1 to pivot open the door structure for removal/replacement/cleaning of the filter media 5974. The filter pull-tab 5974-1 may be structured to change colors to indicate that filter should be cleaned/replaced, e.g., air-activated pull-tab that changes color based on length of exposure.

Figures 1, 94:
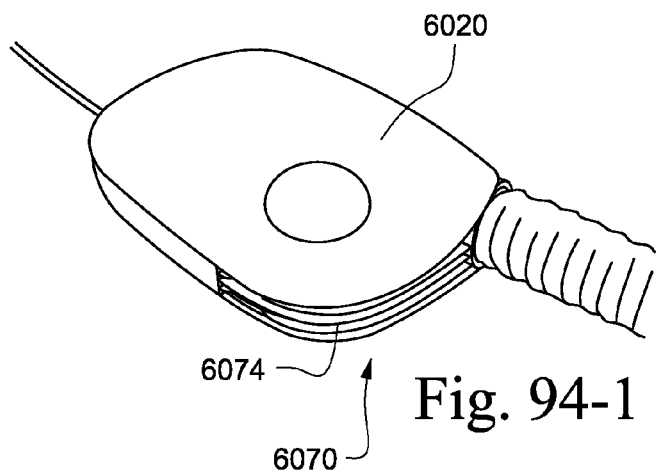
Figures 2, 94:
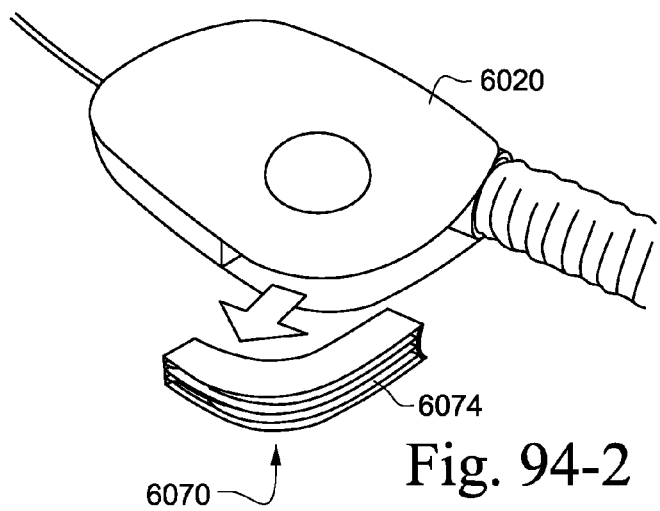

FIGS. 94-1 and 94-2 shows an air filter 6070 arrangement including a filter media 6074 that is releasably supported within a slot provided to the side of the housing 6020. The filter media provides part of the outer surface of the FG housing so it is easily accessible and easily visible to determine cleaning/replacement, e.g., filter media may be structured to change color or may be visibly dirty.

Figure 95:
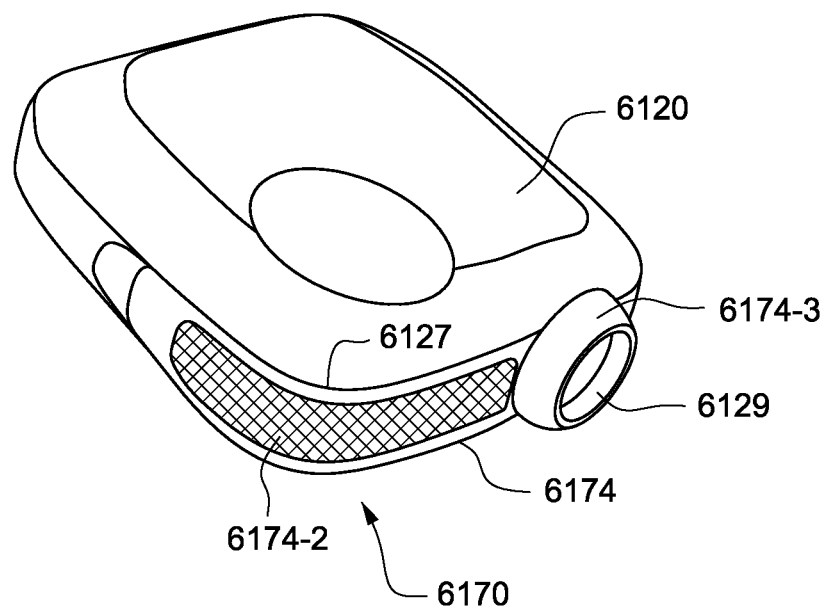
Figure 95:
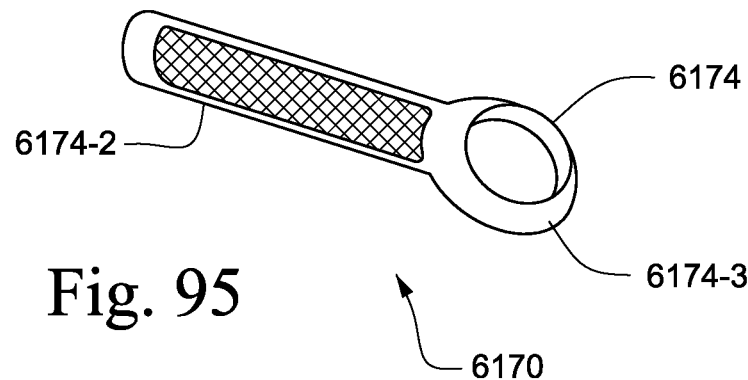
Figure 99:
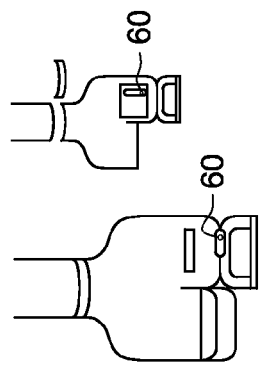
FIGS. 96 to 100 show alternative arrangements for routing a lead wire or cable from the PCB to outside the housing of a flow generator according to alternative examples of the present technology.
Figure 100:
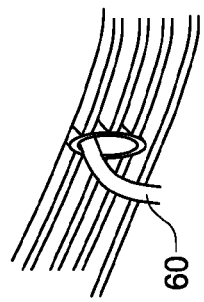
Figure 97:
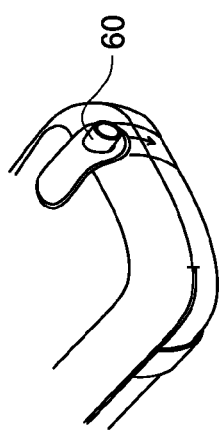
Figure 98:
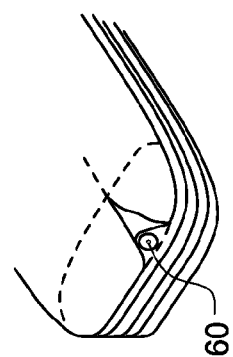
Figure 96:
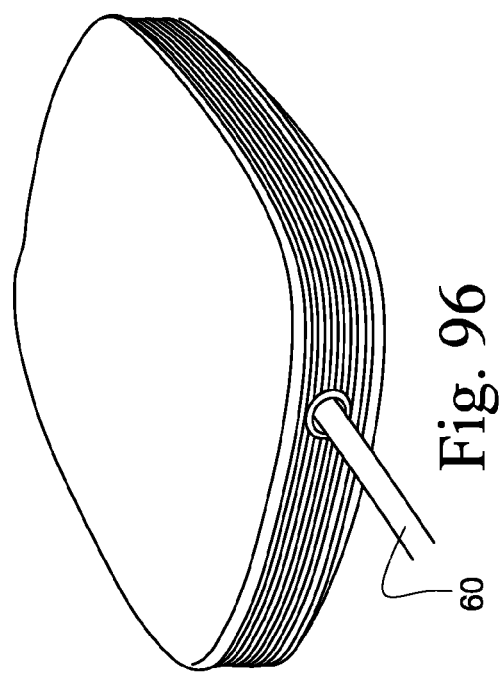

FIG. 95 shows an air filter 6170 arrangement including a filter media 6174 (e.g., constructed of elastomeric material such as TPE). The filter media includes a filter media ring portion 6174-3 adapted to attach to the air flow outlet 6129 of the FG housing 6120 and a filter media body portion 6174-2 providing a filter structure adapted to wrap over and cover the air flow inlet 6127 of the FG housing 6120. The filter media provides part of the outer surface of the FG housing 6120 so it is easily accessible and easily visible to determine cleaning/replacement, e.g., filter visibly dirty.

Figures 1, 102:
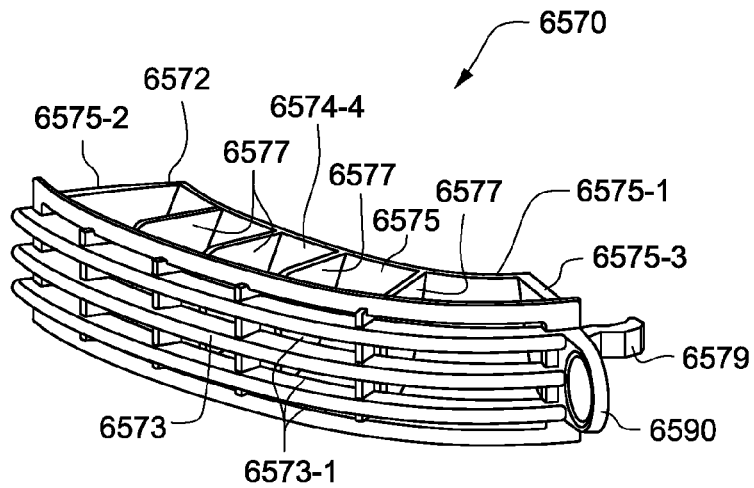
Figures 2, 102:
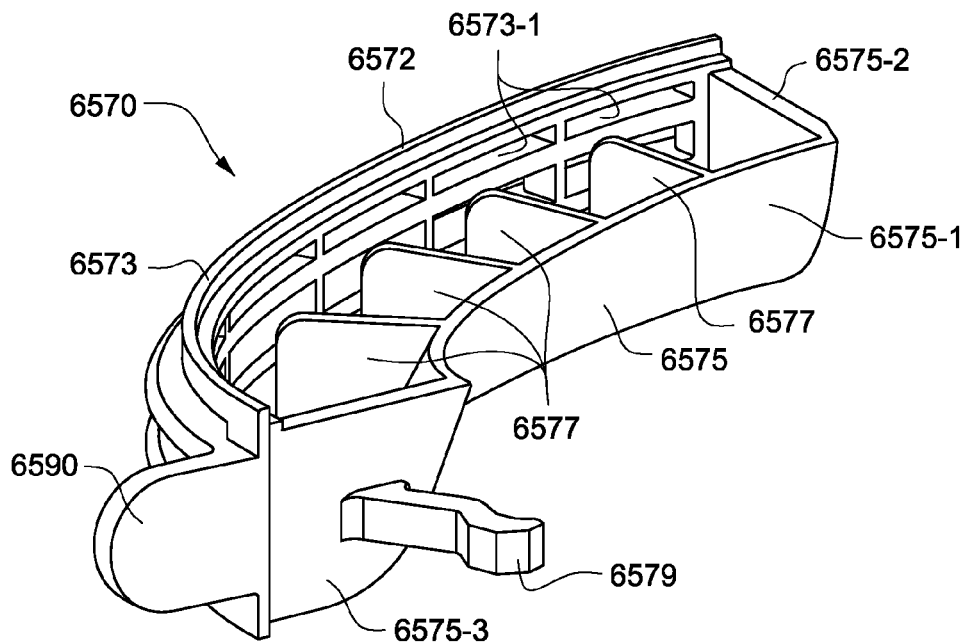
Figures 3, 102:
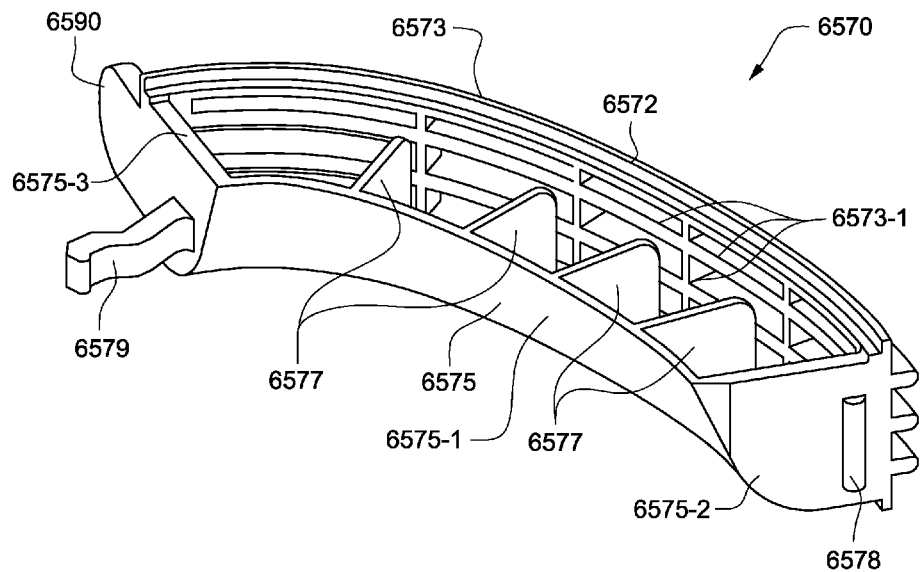
Figures 4, 102:
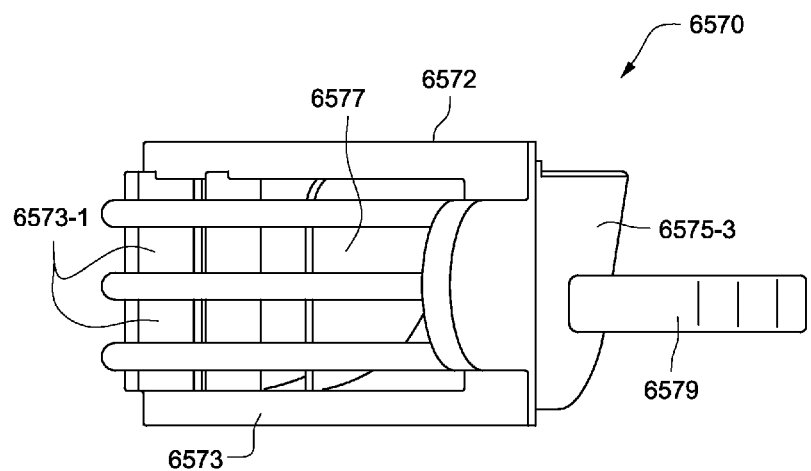
Figures 5, 102:
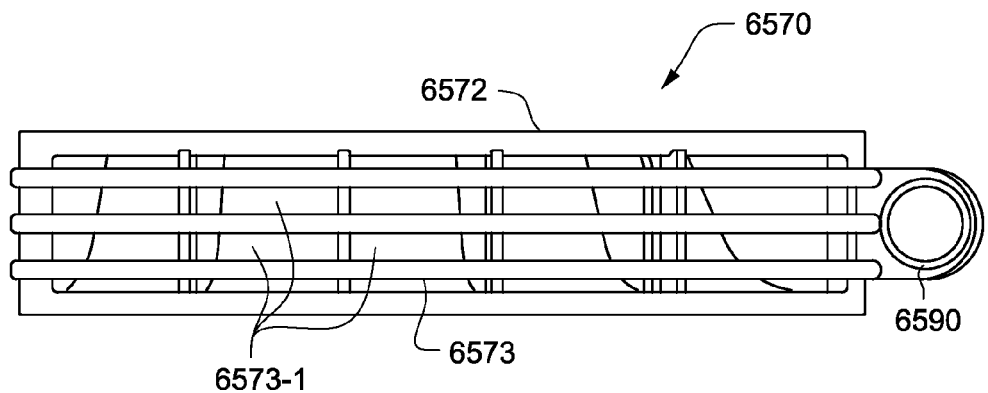
Figures 6, 102:
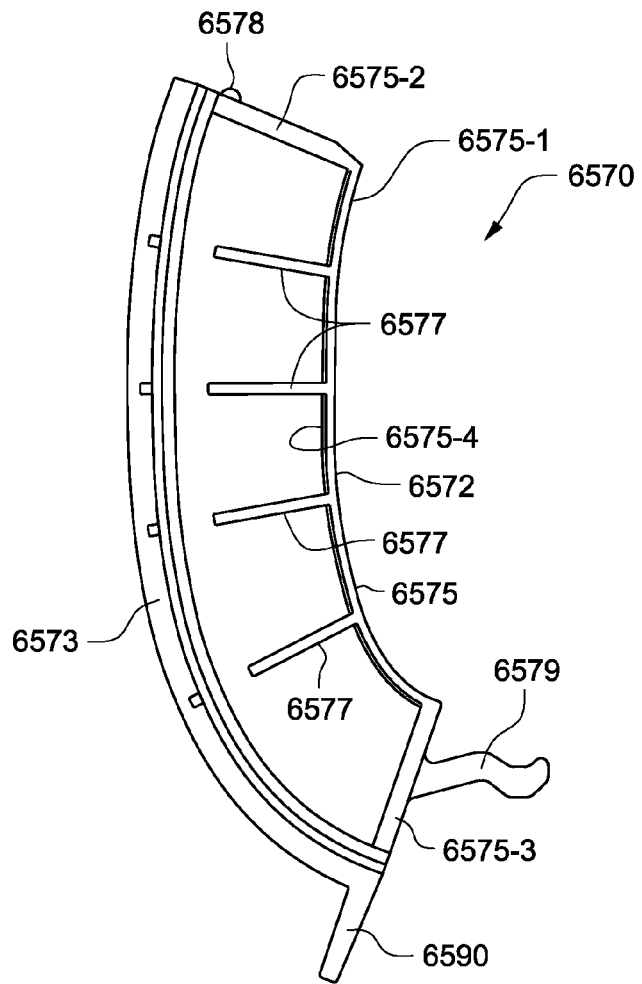
Figures 7, 102:
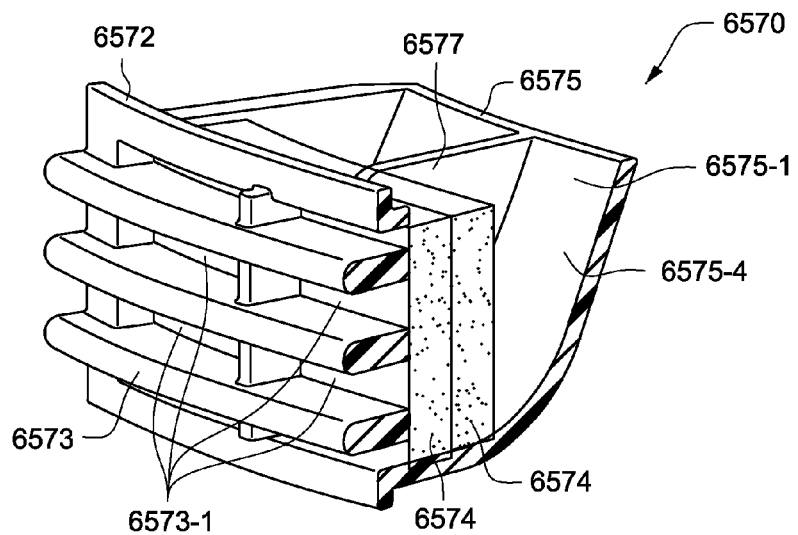
Figures 8, 102:
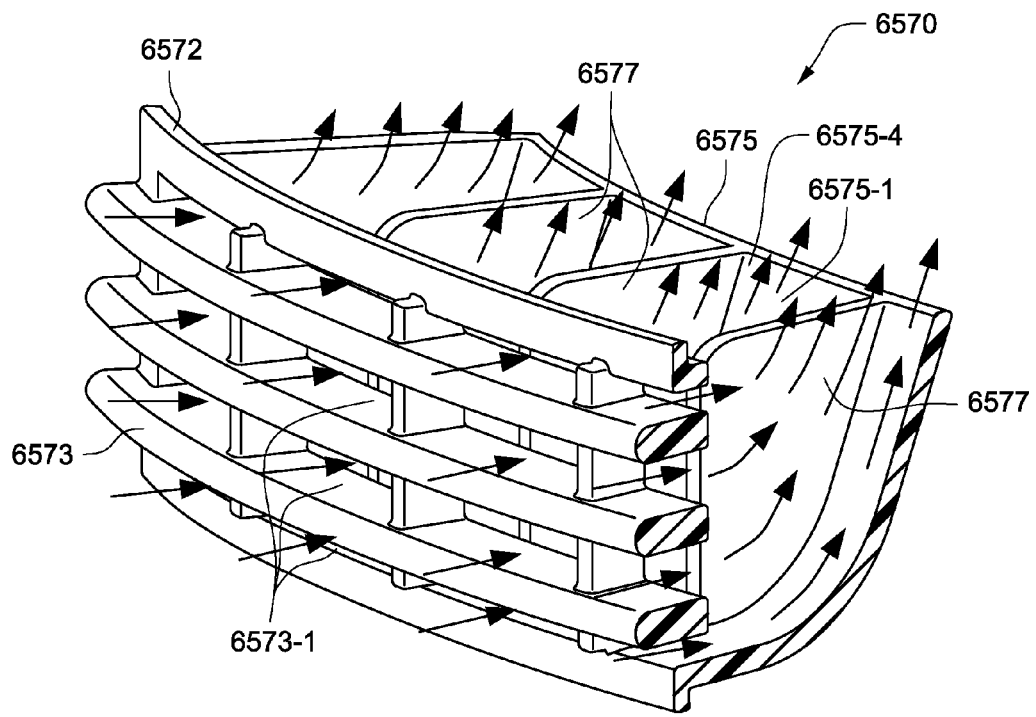
Figures 9, 102:
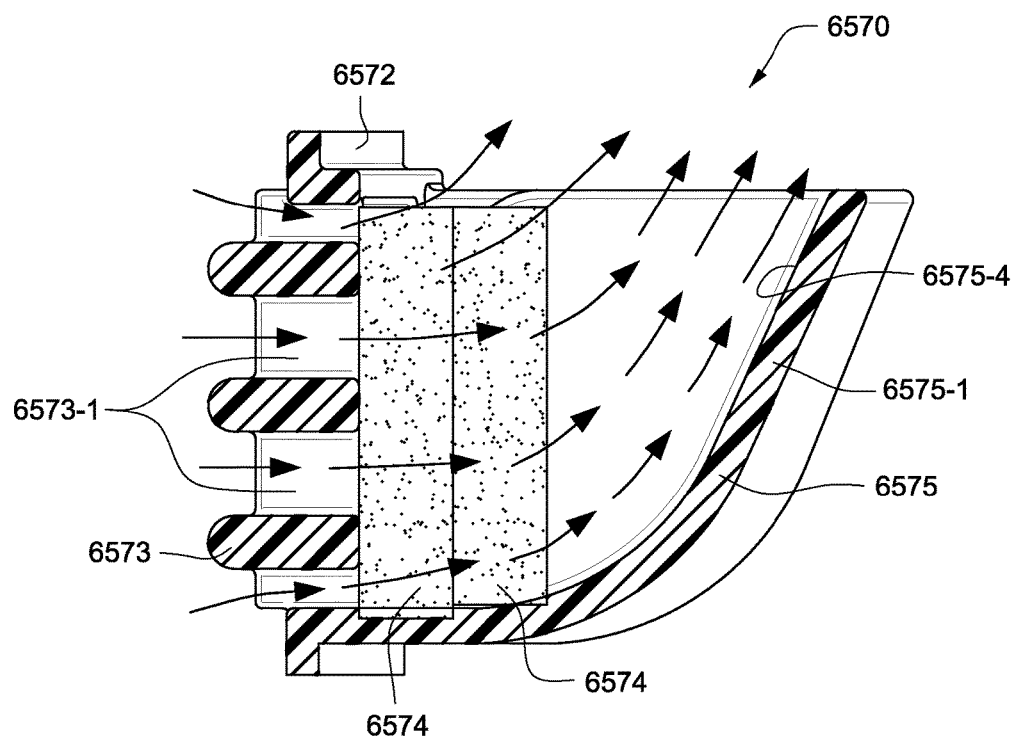

FIGS. 102-1 to 102-9 show an air filter cartridge 6570 according to another example of the present technology. FIGS. 101-1 to 101-11 show such air filter cartridge 6570 positioned within the inlet opening of the flow generator housing 6520 in use.

The air filter cartridge 6570 includes a cartridge body 6572 that supports an air filter 6574. As illustrated, the cartridge body 6572 includes a cartridge front portion 6573 with a grill-like structure or grate, a cartridge rear portion 6575 with an arcuate-shaped cartridge air directing wall 6575-1, and end walls 6575-2, 6575-3 each including structure to retain the cartridge body 6572 within the air flow inlet 6527 of the flow generator housing 6520.

The grill-like or grate front portion 6573 includes horizontally and vertically extending walls that define inlet openings 6573-1 into the air filter cartridge 6570. Such arrangement prevents access to the filter media 6574 supported within the air filter cartridge 6570, prevent user's fingers from poking into the FG housing 6520 and/or prevents large particles from be sucked into the FG housing 6520 through the inlet openings 6573-1.

The arcuate-shaped cartridge air directing wall 6575-1 provides a generally concave surface 6575-4 to direct air flow (see FIG. 102-7). Also, a plurality of cartridge air directing vanes 6577 are provide along the wall, e.g., 4 vanes illustrated however less than 4 vanes or more than 4 vanes are possible. As shown in FIGS. 101-10, 101-11, 102-8 and 102-9, the filter cartridge 6570 is structured to direct the airflow away from the blower chamber inlet and through the plurality of cartridge air directing vanes 6577 that act as manifolds to reduce turbulence within the blower 6530.

As shown in FIG. 102-3, one of the cartridge end walls 6575-2 includes an elongated ridge 6578 adapted to interlock or otherwise engage along one side of the air flow inlet, and the other of the end walls 6576-3 includes an elongated clip arm 6579 adapted to interlock or otherwise engage the other side of the air flow inlet 6527, e.g., ridge end engaged within one side of the air flow inlet and then the air filter cartridge 6570 is pivoted into the air flow inlet until the clip arm 6579 resiliently deflects into engagement with the other side of the air flow inlet 6527 with a snap fit. A cartridge pull-tab 6590 protrudes from the front portion adjacent the clip arm side to allow the user to pull the cartridge pull-tab 6590 to pivot open the air filter cartridge 6570 for removal/replacement/cleaning of the media filter 6574.

The air filter 6570 includes a filter media 6574 designed to filter the incoming air. In an example, the filter media 6574 may include Acousorb Foam (Air Safety Limited:

Grade ASMSB160), which is a tri-laminate sheet composite (e.g., a polyether polyeurethane flexible foam core for sound absorption, a polypropylene sheet backing provided to one side of the foam core for structural stiffness, and a polyurethane film provided to the other side of the foam core for soiling resistance) structured for noise absorption in medical applications. However, it should be appreciated that other suitable foams or filter media may be used.

The filter media 6574 is designed to be thicker to assist in reducing noise radiated back through the air inlet. In an example, the filter media 6574 may include a thickness of about 5-15 mm, e.g., 5 mm, 10 mm. In an example, as shown in FIG. 102-7 and 102-9, two 5 mm pieces of filter media 6574 may be combined to provide a 10 mm thick filter media. In an example, 5 mm pieces of such filter media 6574 may be used for the pieces of acoustic foam 6535 provided along the housing adjacent the blower inlet 6532 and the blower outlet 6534 described above (e.g., see FIGS. 101-5, 101-6, 101-8, and 101-9).

2.4 Air Flow Path

Air is drawn into the FG housing 20 by the blower 30 through the air flow inlet 27, passes through the air filter 70 at the air flow inlet 27, along the inlet air flow vanes 68 and bottom air flow vanes 88, and into the low pressure side of the blower chamber 25 via openings 85-1 in the second blower chamber wall 85. Air is drawn into the blower inlet 32 of the blower 30 and a supply of pressurized air exits the blower 30 at the blower outlet 34 and passes into the high pressure side of the blower chamber 25. The pressurized air exits the blower chamber 25 via apertures 65-1 in the first blower chamber wall 65 and passes through the air flow outlet 29 for delivery to the patient.

Alternative Air Flow Paths

It should be appreciated that the FG housing 20 and/or suspension device 40 may include and/or support alternative structures, e.g., to provide alternative air flow paths, to support the PCB 50, and/or to absorb sound, etc.

Figures 1, 29:
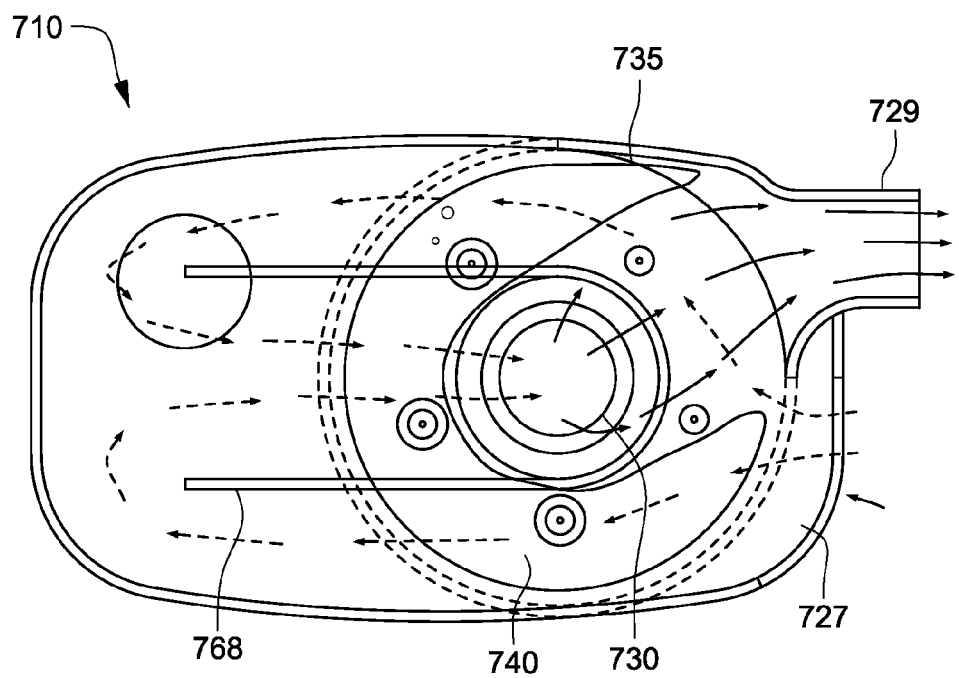
Figures 2, 29:
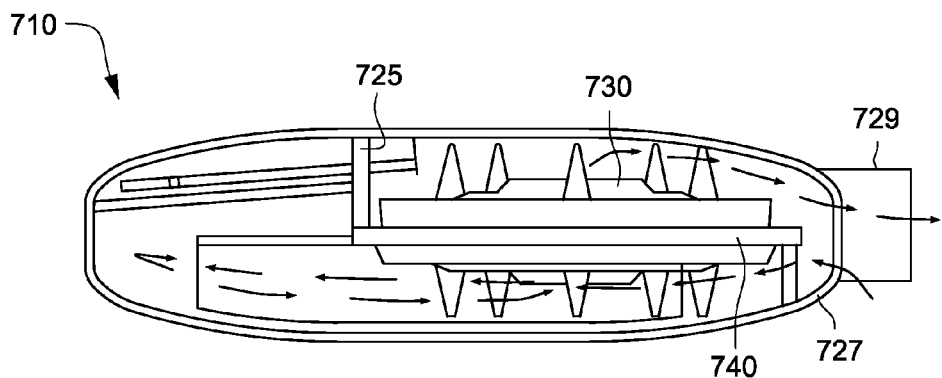
Figures 3, 29:
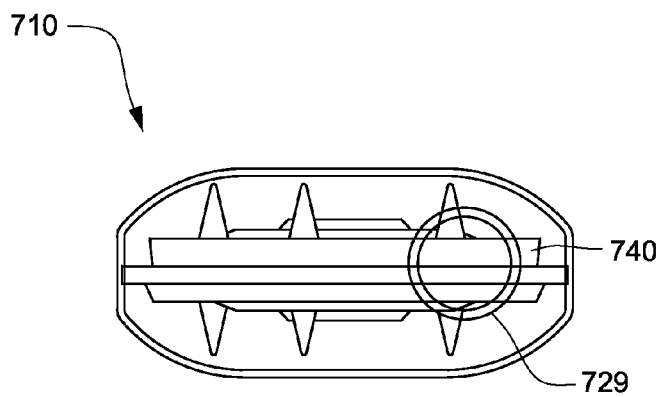

For example, FIGS. 29-1 to 29-3 show a flow generator 710 according to another example of the present technology. In this example, the air flow inlet 727 and the air flow outlet 729 are provided on the same side of the FG housing 720. The blower 730 is supported within the blower chamber 725 by the suspension device 740 which provides a seal between the low pressure side and the high pressure side of the blower. A U-shaped inlet air flow vane 768 (e.g., constructed of silicone) is provided to the FG housing 720 and/or suspension device 740 along the low pressure side to direct or guide air from the inlet towards the blower inlet 732. The inlet air flow vane 768 provides a relatively long inlet flow path with many surfaces to reflect sound and reduce noise back through the inlet. An arcuate or C-shaped piece of acoustic foam 735 may be provided to support the blower 730 and provide sound absorption and suspension. As shown in FIGS. 29-2 and 29-3 the suspension device 740 may be include symmetrical top and bottom portions to support the blower 730 substantially within the middle of the FG housing 720, e.g., top and bottom edges of the suspension device equidistant from transverse axis of the blower.

Figure 30:
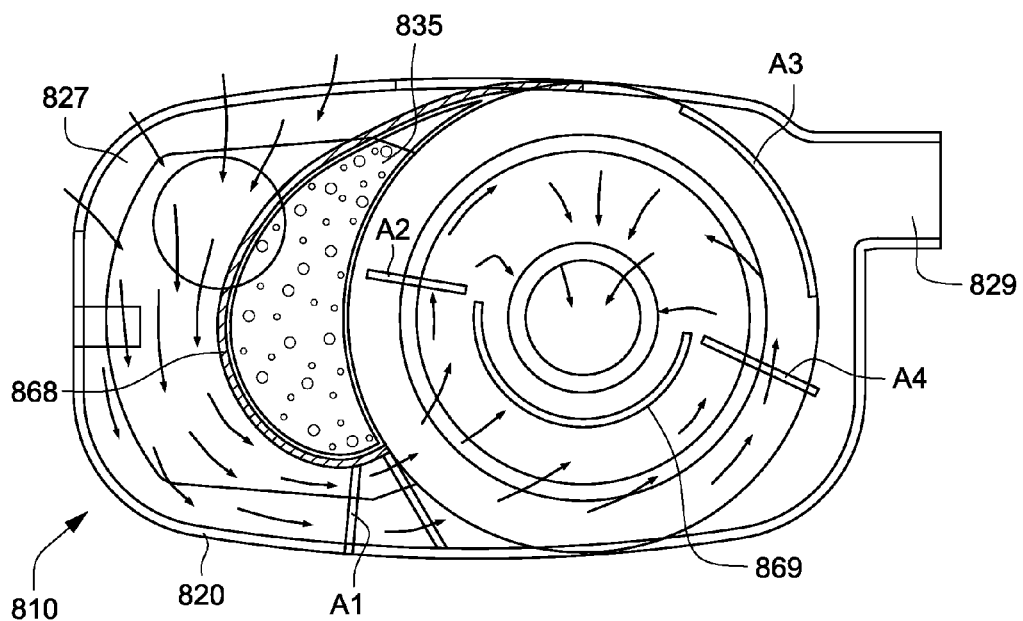
FIG. 30 shows a flow generator according to another example of the present technology.

FIG. 30 shows a flow generator 810 according to another example of the present technology. In this example, the air flow inlet 827 and the air flow outlet 829 are provided on opposite sides of the FG housing 820. A curved or arcuate inlet air flow vane 868 directs air from the air flow inlet 827 towards the blower inlet 832, and provides a relatively long inlet flow path to reflect sound and reduce noise back through the inlet. A piece of acoustic foam 835 is provided along the inlet air flow vane 868 and an arcuate wall or blower baffle wall 869 (e.g., constructed of silicone) is provided adjacent to and at least partially surrounds the blower inlet 832. The inlet air flow vane 868 may be constructed of a hard (e.g., plastic) or soft (e.g., silicone) material. In an alternative example, a piece of acoustic foam 835 alone may be used as the air flow vane, i.e., air flow vane not provided.

The cross-sectional areas A1, A2, A3, and A4 in FIG. 30 include a suitable size to prevent turbulent airflow around the blower. For example, such cross-sectional areas are of a sufficient size to provide a flow rate less than 10 m/s, e.g., about 5-6 m/s.

Figures 1, 31:
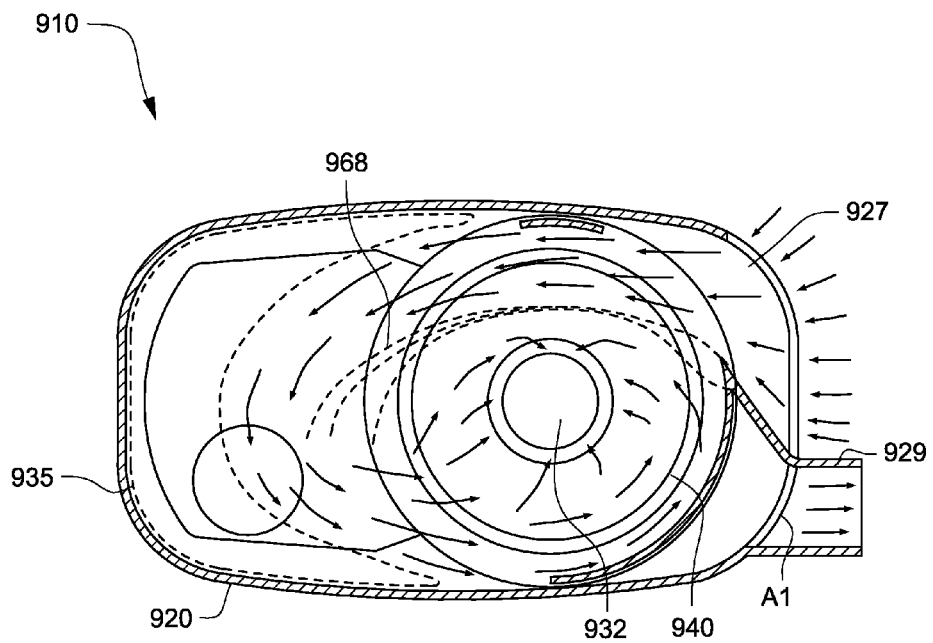
Figures 2, 31:
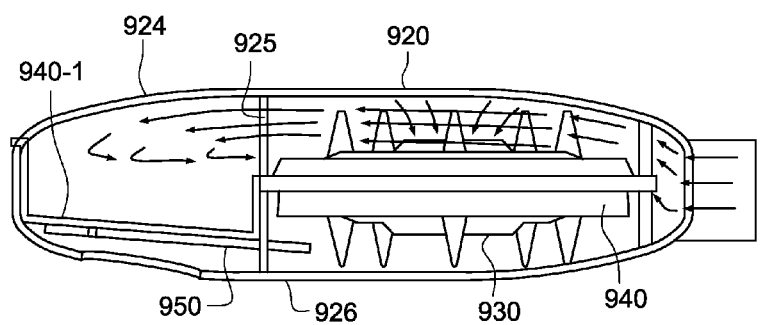

FIGS. 31-1 and 31-2 show a flow generator 910 according to another example of the present technology. In this example, the air flow inlet 927 and the air flow outlet 929 are provided on the same side of the FG housing 920. The blower 930 is supported within the blower chamber 925 by the suspension device 940 which provides a seal between the low pressure side and the high pressure side of the blower. A silicone wall 940-1 (e.g., which may be an extended section of the suspension device) is provided to seal the air path from the PCB 950. The PCB 950 may be attached to the silicone wall 940-1 (e.g., heat staking), and the silicone wall 940-1 may include an end portion positioned between top housing 924 and bottom housing 926 parts to provide a seal between the housing parts and provide a sealed outlet for wires from the PCB. A semi-rigid inlet air flow vane 968 (e.g., constructed of silicone and may be optionally molded as part of the suspension device) directs air from the air flow inlet 927 towards the blower inlet 932. The inlet air flow vane 968 may be at least partly flexibly to allow the vane to at least partly flex during use, e.g., as indicated by multiple outlines of the vane in dashed lines. A piece of acoustic foam 935 may be provided to an end of the FG housing 920 to direct air and provide sound absorption.

The flow generator 910 provides sufficient clearance for air leaving the air flow outlet 929, i.e., choke points have sufficient cross-section area. Also, the cross-section area A1 of the region prior to the air flow outlet 929 is larger than the outlet diameter to prevent turbulent flow at this point.

Figures 1, 32:
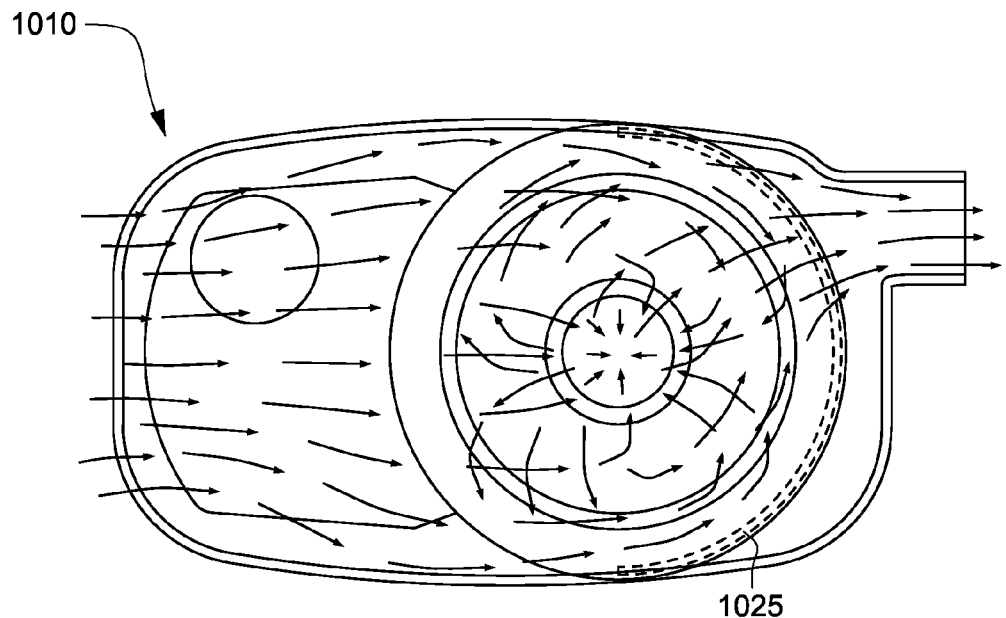
Figures 2, 32:
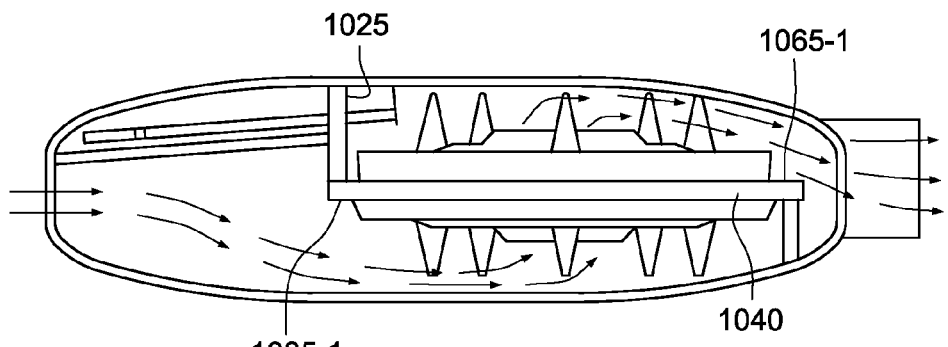
Figures 3, 32:
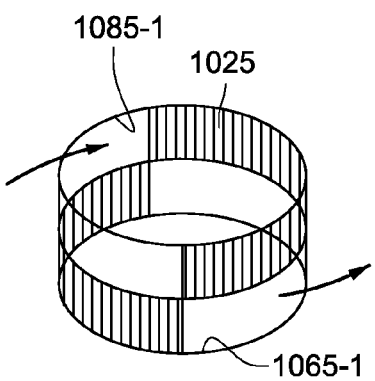

FIGS. 32-1 to 32-3 show a flow generator 1010 according to another example of the present technology. This example shows an alternative cylindrical blower chamber 1025 with at least one opening 1085-1 to allow air to enter the blower on the low pressure side and at least one aperture 1065-1 for the air to exit the blower chamber 1025 on the high pressure side. The suspension device 1040 provides the seal between the low and high pressure sides of the blower chamber.

Figures 1, 34:
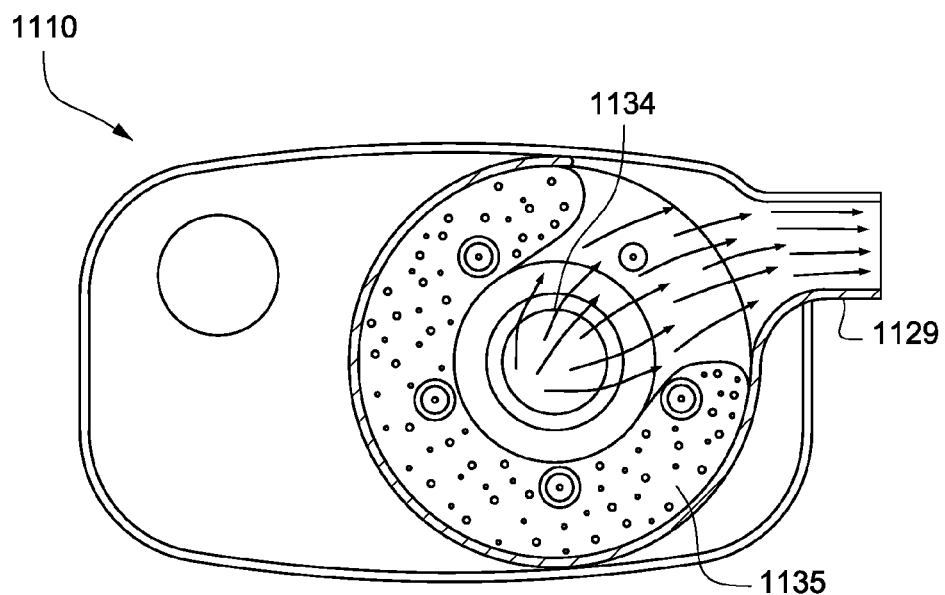
Figures 2, 34:
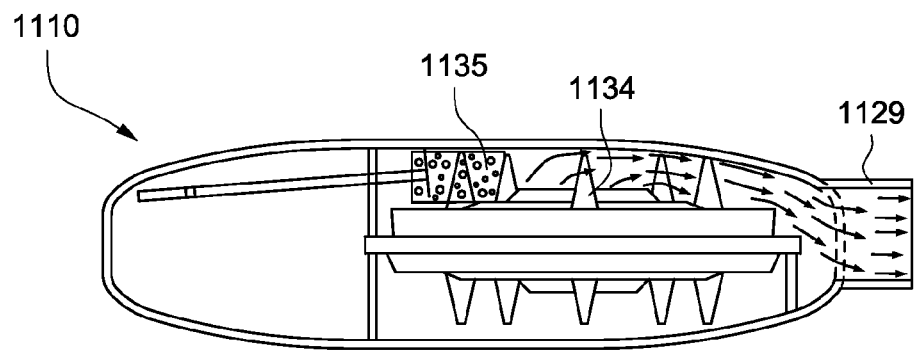

FIGS. 34-1 and 34-2 show a flow generator 1110 according to another example of the present technology. In this example, an arcuate or U-shaped piece of acoustic foam 1135 is provided adjacent to the blower outlet 1134 and at least partially surrounds the blower outlet 1134 to direct air towards the air flow outlet 1129 and provide sound absorption.

Figures 1, 35:
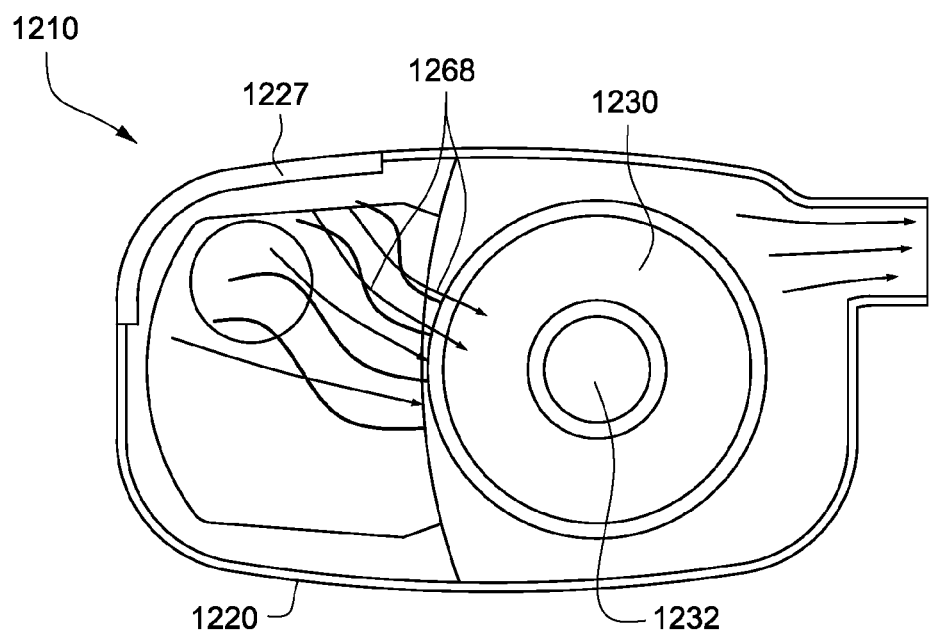
Figures 2, 35:
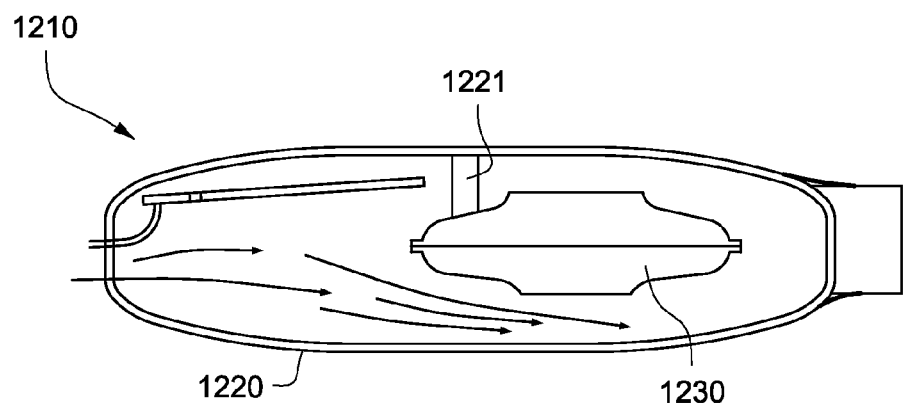

FIGS. 35-1 and 35-2 show a flow generator 1210 according to another example of the present technology. In this example, the blower 1230 may be suspended within the FG housing 1220 by blower wall member 1221. Also, air flow through the FG housing 1220 may help to suspend the blower 1230 within the FG housing 1220. One or more straight or curved inlet air flow vanes 1268 may be provided to direct air from the air flow inlet 1227 to the blower inlet 1232 of the blower 1230.

Figures 1, 36:
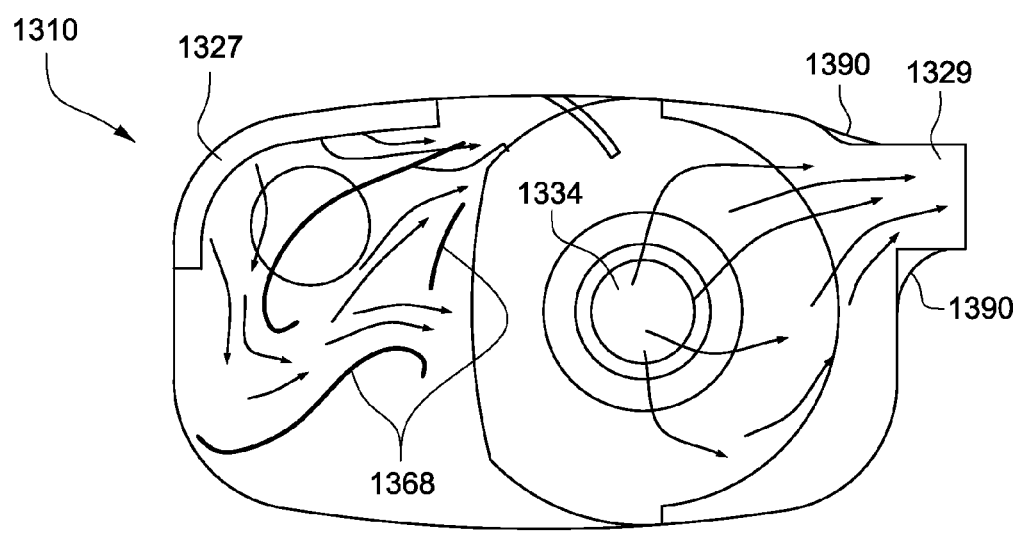
Figures 2, 36:
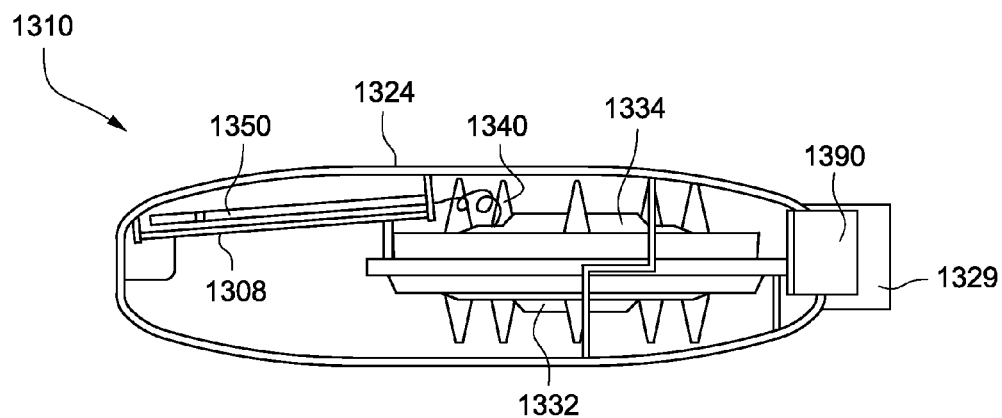
Figures 3, 36:
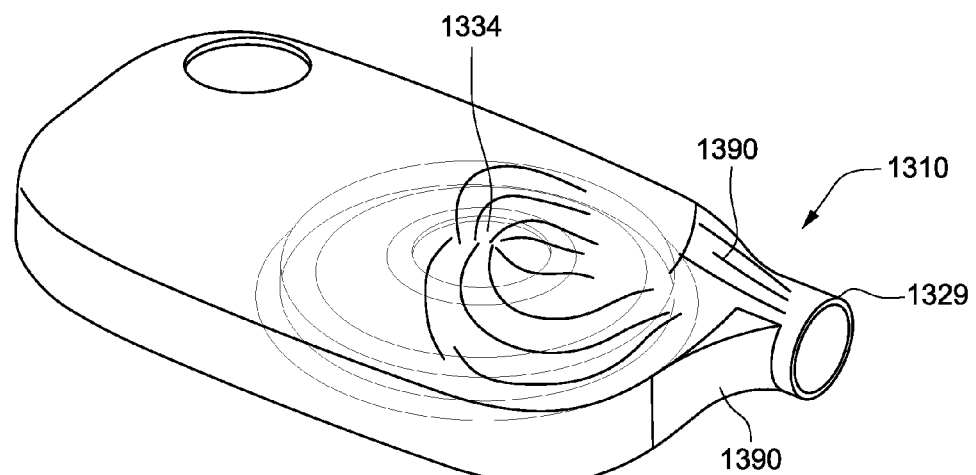

FIGS. 36-1 to 36-3 show a flow generator 1310 according to another example of the present technology. In this example, inlet air flow vanes and/or internal walls 1368 are provided to direct air from the air flow inlet 1327 towards the blower inlet 1332. In addition, outlet air flow vanes 1390 are provided adjacent the air flow outlet 1329 to direct air from the blower outlet 1334 towards the air flow outlet 1329. A sealing cover 1308 provided to the top cover 1324 or suspension device 1340 encloses and seals the PCB 1350 from the air flow path.

Figure 37:
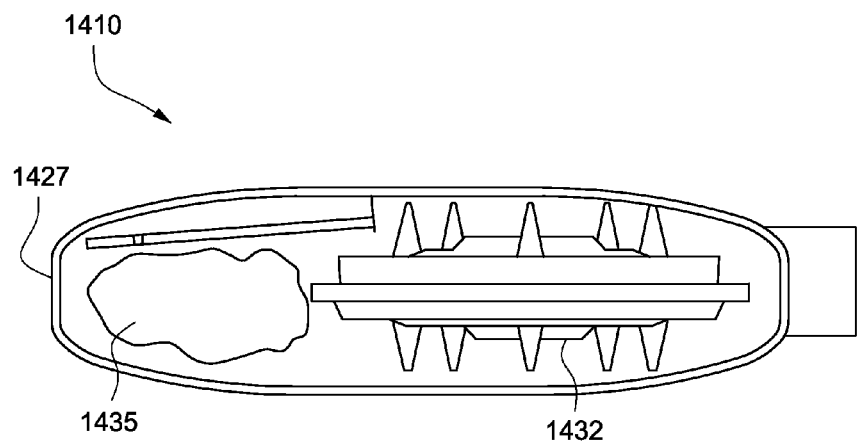
FIG. 37 shows a flow generator according to another example of the present technology.

FIG. 37 shows a flow generator 1410 including sound absorbing material or acoustic foam 1435 provided to the air flow path between the air flow inlet 1427 and the blower inlet 1432.

Figure 38:
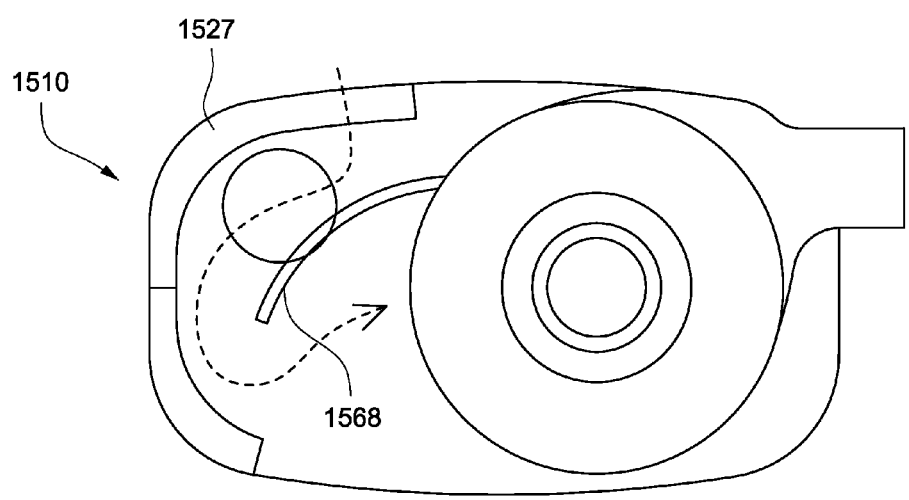
FIG. 38 shows a flow generator according to another example of the present technology.

FIG. 38 shows a flow generator 1510 including an arcuate inlet air flow vane 1568 to direct air from the air flow inlet 1527 towards the blower inlet 1532.

FIGS. 40 to 47 show alternative examples of flow generators including walls and/or pieces of acoustic foam for directing air flow and absorbing sound.

Figure 40:
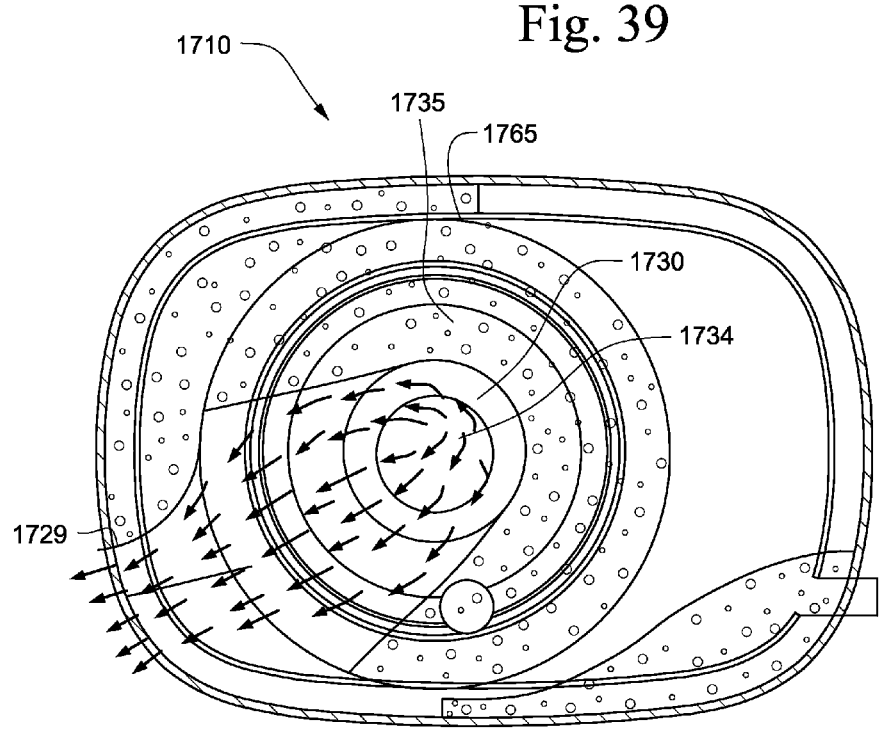
FIGS. 40 to 47 are schematic views of flow generators according to alternative examples of the present technology.

For example, FIG. 40 shows a flow generator 1710 in which the high pressure side includes an annular wall or first blower chamber wall 1765 surrounding the blower outlet 1734 to direct air towards the outlet 1729. In addition, an arcuate or C-shaped piece of acoustic foam 1735 may be provided to support the blower 1730, provide sound absorption and suspension, and direct air towards the air flow outlet 1729.

Figure 41:
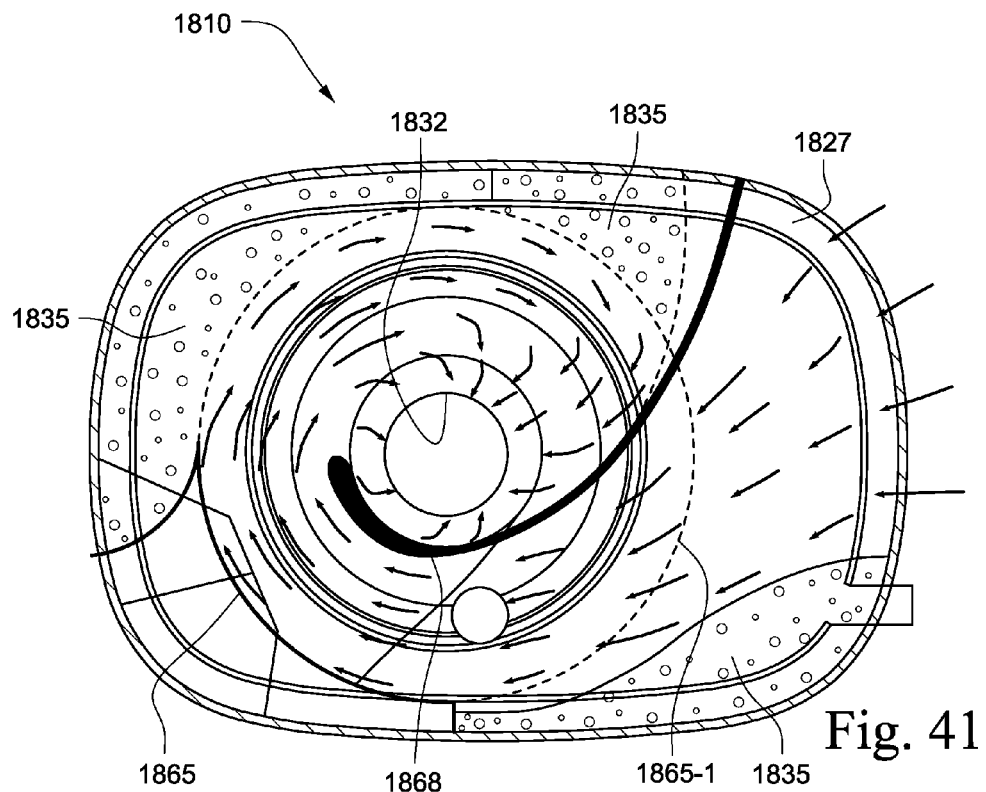

FIG. 41 shows a flow generator 1810 according to another example of the present technology. In this example, the low pressure side includes an annular wall or first blower chamber wall 1865 surrounding the blower inlet 1832. One or more apertures 1865-1 are provided in the first blower chamber wall 1865 to allow air to flow from the air flow inlet 1827 to the blower inlet 1832. An arcuate inlet air flow vane 1868 is provided to direct air from the air flow inlet 1827 towards the blower inlet 1832. In an example, the inlet air flow vane 1868 may be semi-rigid (e.g., constructed of 60-80 Shore A durometer silicone) to allow some flexibility for directing air flow, e.g., the location and shape of the air flow vane may be modified to accommodate flow. Also, pieces of acoustic foam 1835 may be provided along the air flow path to absorb sound and direct air towards the blower inlet 1832.

Figure 42:
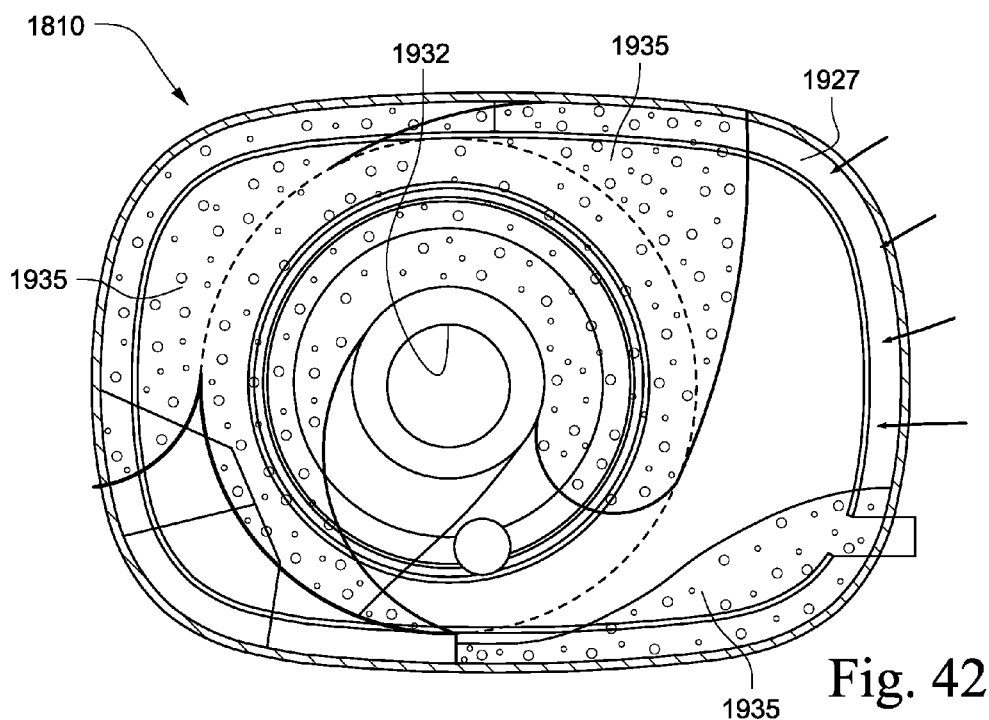

FIG. 42 shows a flow generator 1910 according to another example of the present technology. In this example, the low pressure side includes pieces of acoustic foam 1935 along the air flow path to absorb sound and to direct air from the air flow inlet 1927 towards the blower inlet 1932.

Figure 43:
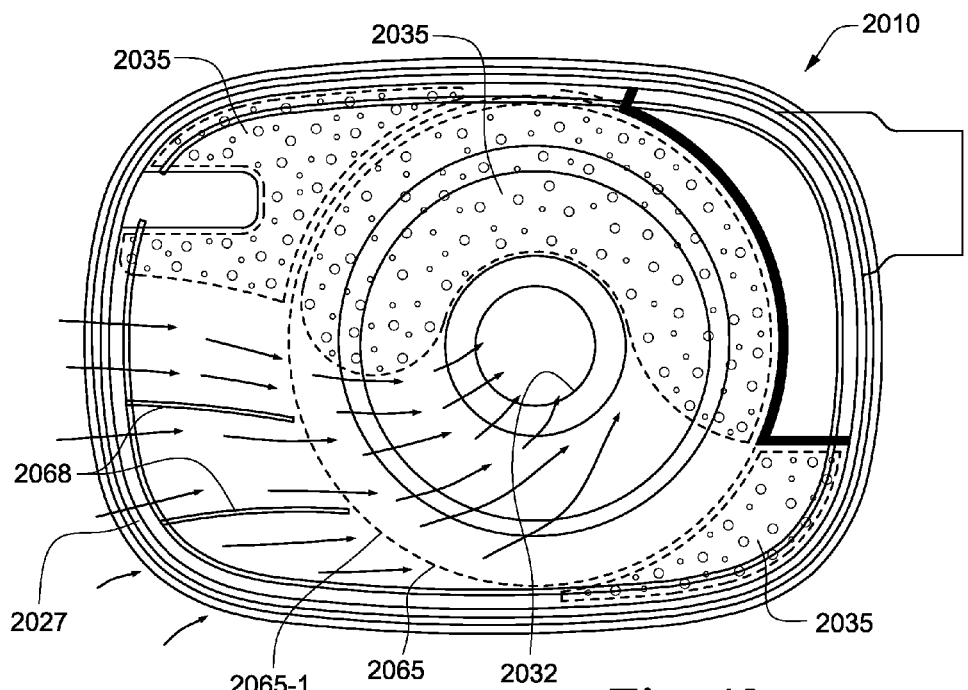

FIG. 43 shows a flow generator 2010 according to another example of the present technology. In this example, the low pressure side includes an annular wall or first blower chamber wall 2065 surrounding the blower inlet 2032. One or more apertures 2065-1 are provided in the first blower chamber wall 2065 to allow air to flow from the air flow inlet 2027 to the blower inlet 2032. Inlet air flow vanes 2068 (e.g., 2 vanes illustrated, but 1, 3, 4, or more vanes are possible) are provided to direct air from the air flow inlet 2027 towards the apertures 2065-1 in the first blower chamber wall 2065. The shape of the inlet air flow vanes may vary to provide different flow path designs. Also, pieces of acoustic foam 2035 may be provided to absorb sound and direct air towards the air flow inlet 2027.

Figure 44:
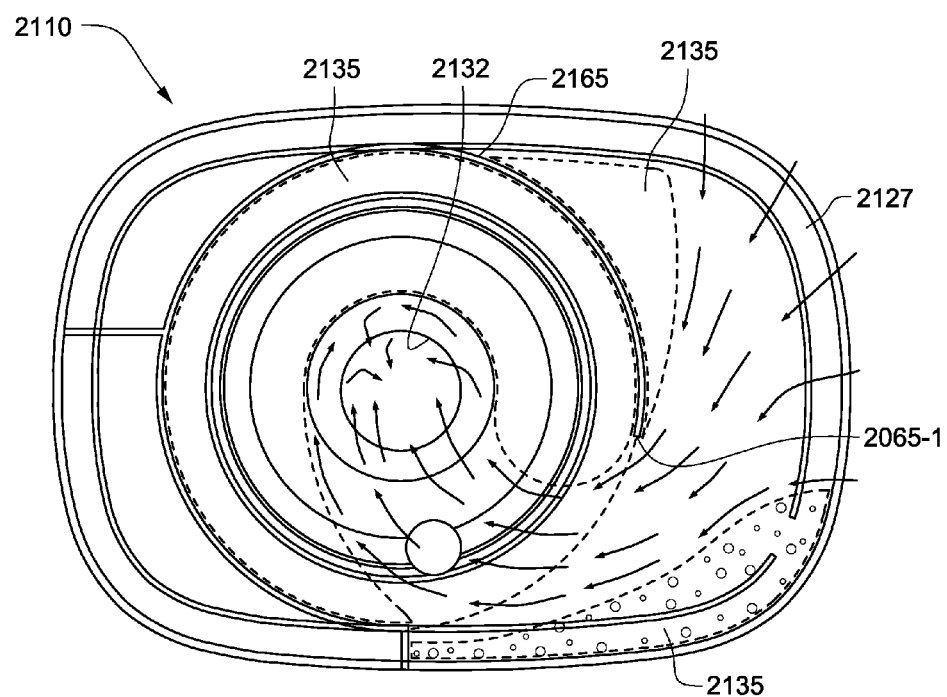

FIG. 44 shows a flow generator 2110 according to another example of the present technology. In this example, the low pressure side includes an annular wall or first blower chamber wall 2165 surrounding the blower inlet 2132. One or more apertures 2165-1 are provided in the first blower chamber wall 2165 to allow air to flow from the air flow inlet 2127 to the blower inlet 2132. Pieces of acoustic foam 2135 are provided along the air flow path to absorb sound and to direct air from the air flow inlet 2127 towards the blower inlet 2132.

Figure 45:
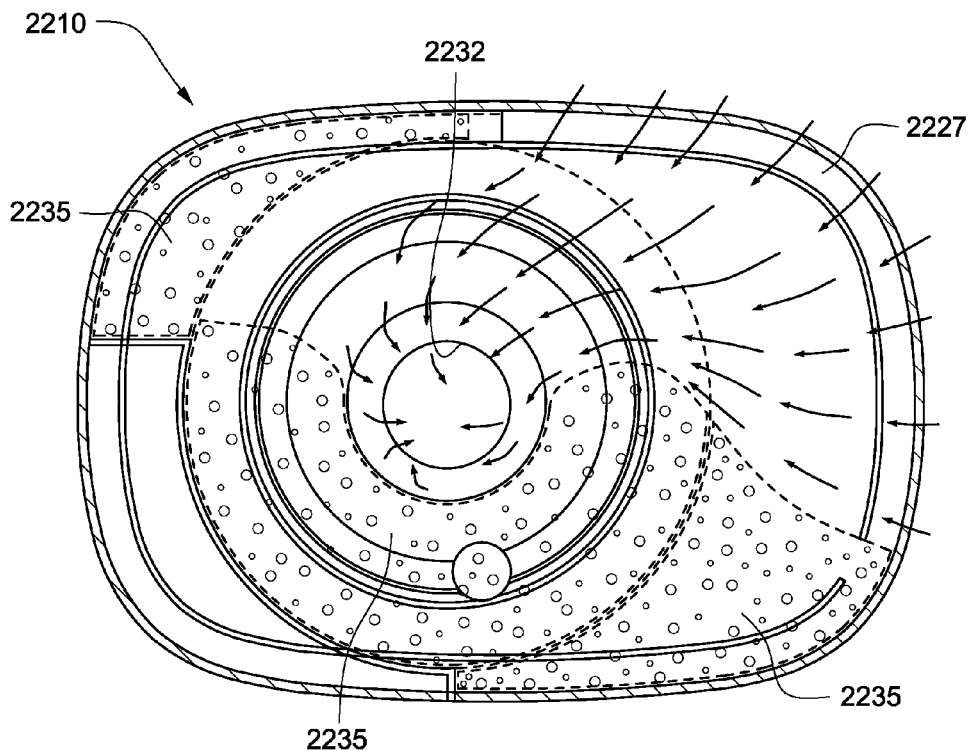

FIG. 45 shows another example of a flow generator 2210 including an alternative arrangement of pieces of acoustic foam 2235 along the air flow path to absorb sound and to direct air from the air flow inlet 2227 towards the blower inlet 2232.

Figure 46:
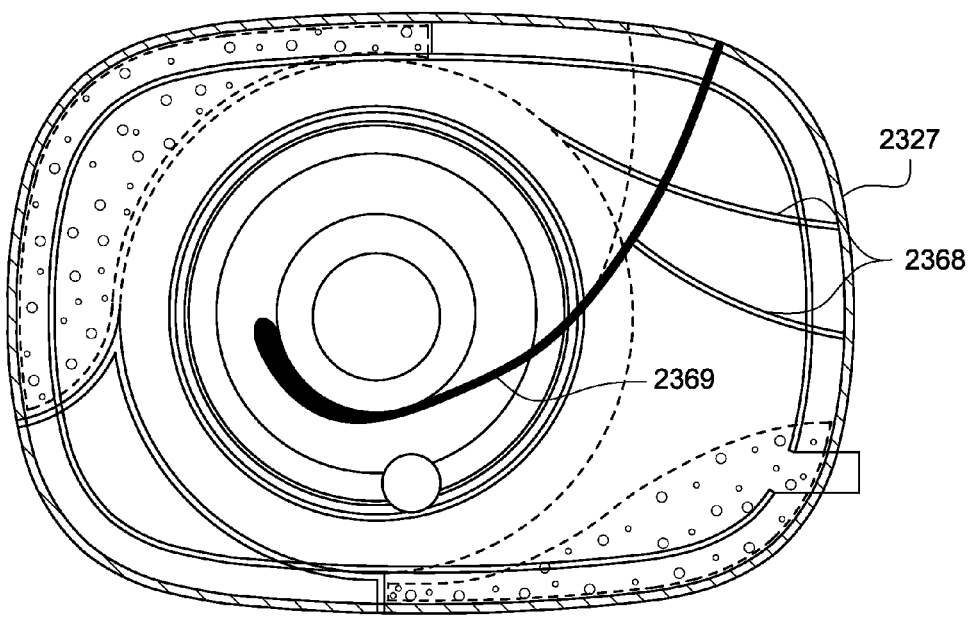

FIG. 46 shows a flow generator 2310 similar to that shown in FIG. 41. In this example, one or more inlet air flow vanes 2368 may be provided adjacent the air flow inlet 2327 in addition to or as an alternative to the arcuate blower baffle wall 2369.

Figure 47:
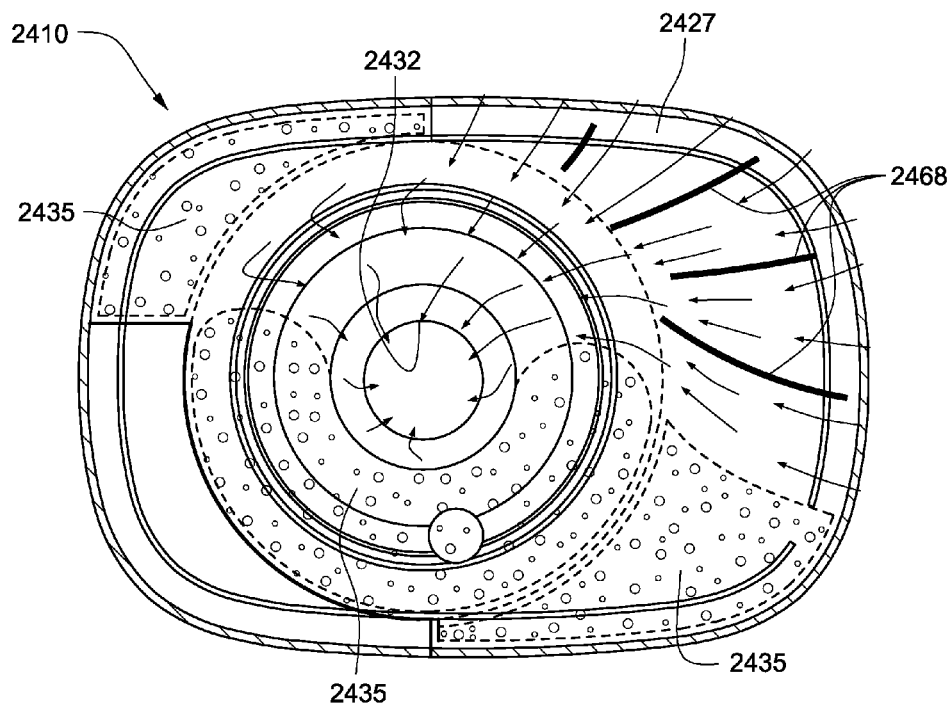

FIG. 47 shows another example of a flow generator 2410 including air flow vanes 2468 adjacent the inlet and an alternative arrangement of pieces of acoustic foam 2435 along the air flow path to absorb sound and to direct air from the air flow inlet 2427 towards the blower inlet 2432.

Figure 58:
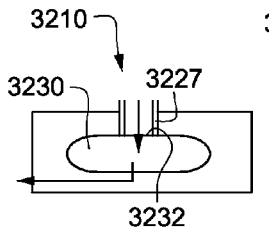
FIGS. 58 to 71 show alternative housing and/or suspension arrangements for a flow generator according to alternative examples of the present technology.

FIG. 58 shows another example of a flow generator 3210 including a ducted air flow inlet 3227 towards the blower inlet 3232 of the blower 3230.

Figure 59:
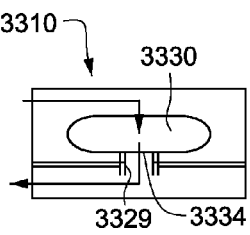

FIG. 59 shows another example of a flow generator 3310 including a ducted air flow outlet 3329 from the blower outlet 3334 of the blower 3330.

Figure 60:
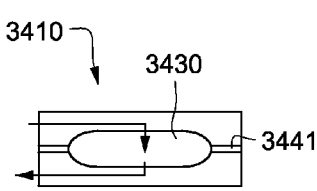

FIG. 60 shows another example of a flow generator 3410 including a pressure seal 3441 along the perimeter of the blower 3430 to separate low and high pressure sides.

Figure 61:
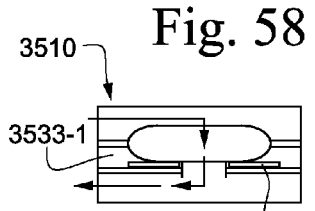

FIG. 61 shows another example of a flow generator 3510 including a PCB chamber 3533-1 within the housing interior (e.g., along a side of the blower) for the PCB 3550.

Figure 62:
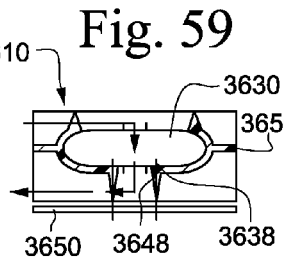

FIG. 62 shows another example of a flow generator 3610 in which blower lead wires 3638 from the blower 3630 extend through the suspension device 3640 to the PCB 3650, e.g., lead wires extend through pegs or cones 3648 of the suspension device.

Figure 63:
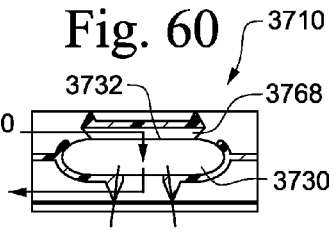

FIG. 63 shows an example of a flow generator 3710 similar to FIG. 62. In contrast, pre-swirl inlet air flow vanes 3768 are provided to the blower 3730 (e.g., overmolded) to direct air into the blower inlet 3732 of the blower 3730.

Figure 64:
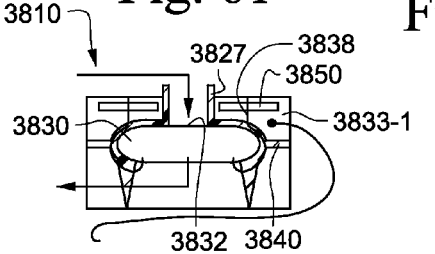

FIG. 64 shows another example of a flow generator 3810 in which the suspension device 3840 for the blower 3830 includes a ducted air flow inlet 3827 towards the blower inlet 3832 of the blower 3830, which arrangement provides a sealed PCB chamber 3833-1 for the PCB 3850. Blower lead wires 3838 from the blower 3830 may extend to the PCB 3850 through the wall of the ducted air flow inlet 3827 and/or through the side wall of the suspension device 3840 supporting the blower 3840.

Figure 65:
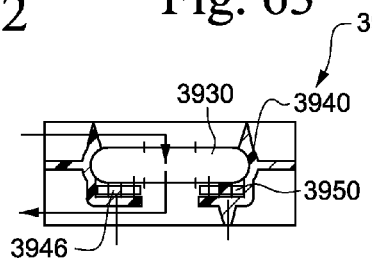

FIG. 65 shows another example of a flow generator 3910 in which the suspension device 3940 supports the PCB 3950 adjacent to the blower 3930. As illustrated, the PCB 3950 may include one or more pass through holes to receive support members 3946 of the suspension device 3940.

Figure 66:
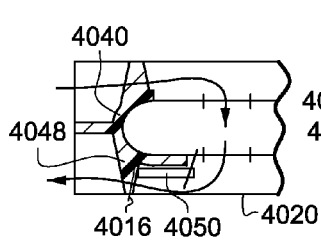
Figure 67:
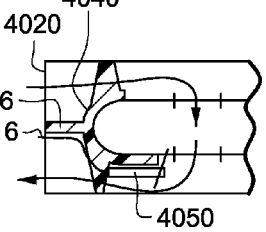

FIGS. 66 and 67 show examples for routing a power cord 4016 from the PCB 4050 to outside the FG housing 4020, e.g., along a cone 4048 of the suspension device 4040 and through a wall of the FG housing 4020 (FIG. 66) or along a support member 4046 of the suspension device 4040 and through the wall of the FG housing 4020 (FIG. 67).

Figure 68:
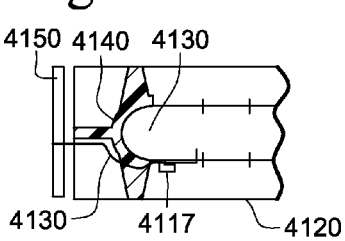

FIG. 68 shows an example of a hitching post 4117 for routing blower lead wires 4138 from the blower 4130, along the suspension device 4140 to the PCB 4150 outside the FG housing 4120.

Figure 69:
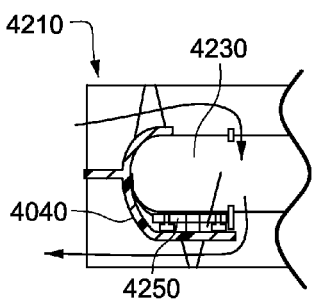

FIG. 69 shows another example of a flow generator 4210 in which the suspension device 4240 supports the PCB 4250 adjacent to the blower 4230.

Figure 70:
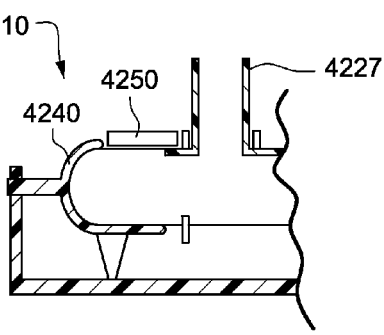

FIG. 70 shows another example of a flow generator 4210 including a ducted inlet 4227 and suspension device 4240 which provides a sealed chamber for the PCB 4250.

Figure 71:
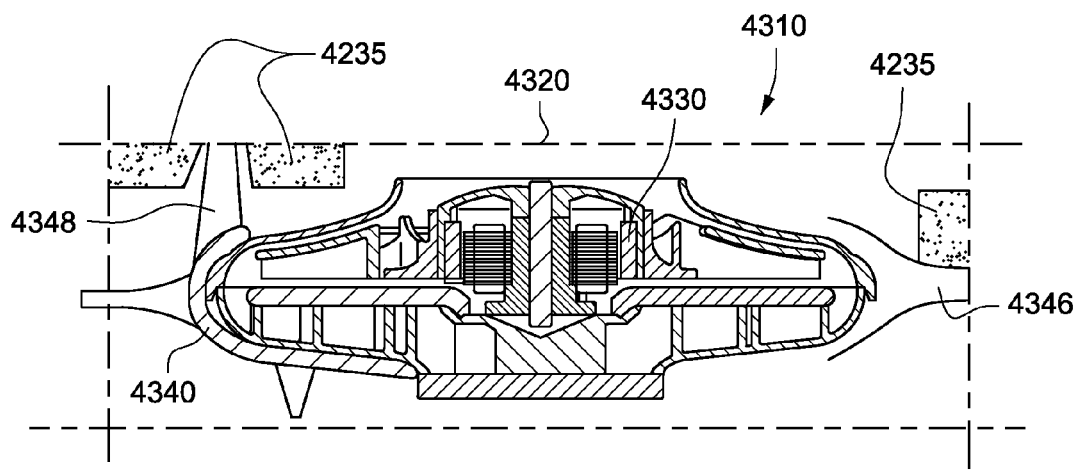

FIG. 71 shows another example of a flow generator 4310 including a suspension device 4340 to support the blower 4330 within the FG housing 4320 at appropriate clearing from housing walls for pneumatics and noise attenuation. Also, acoustic foam 4235 may be provided along the suspension device 4340 (e.g., along the cones 4348 and/or support member 4346 of the suspension device 4340), e.g., to absorb sound.

Figure 73:
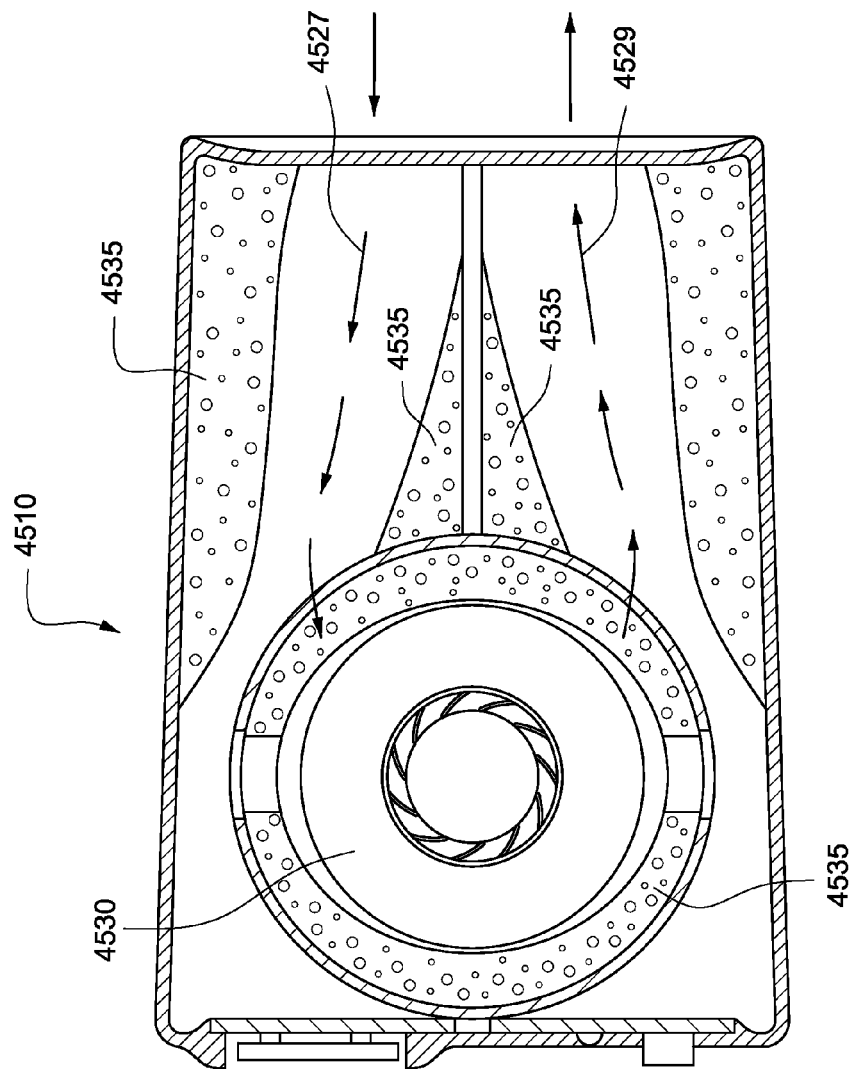
FIG. 73 shows a flow generator according to another example of the present technology.

FIG. 73 shows another example of a flow generator 4510 including pieces of acoustic foam 4535 that define an air flow inlet 4527 path to the blower 4530, define an air flow outlet 4529 path from the blower 4530, and support the blower 4530, while absorbing sound.

Figure 74:
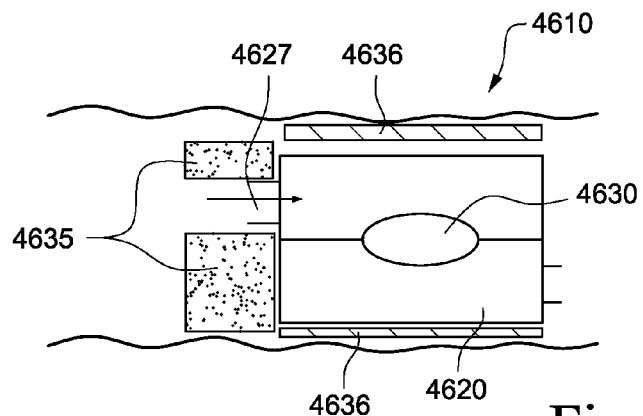
FIG. 74 shows a flow generator according to another example of the present technology.
Figure 75:
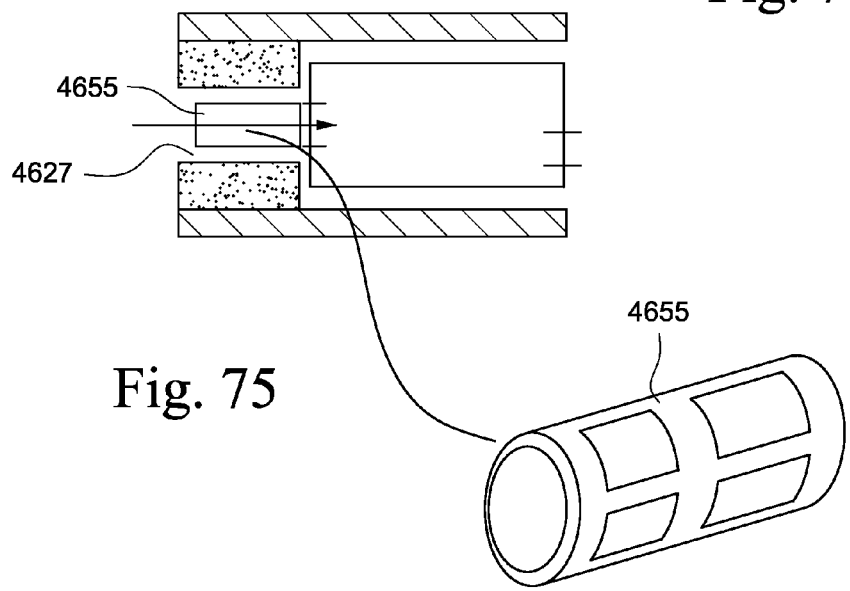
FIG. 75 shows a flow generator according to another example of the present technology.

FIG. 74 shows another example of a flow generator 4610 including pieces of acoustic foam or silicone 4635 that define an air flow inlet 4627 path to the blower 4630, while absorbing sound. Pieces of acoustic foam or silicone 4636 may also be provided to top and bottom portions of the FG housing 4620, e.g., for absorbing shock and sound. In an alternative example, as shown in FIG. 75, a muffler 4655 (e.g., tube with one or more openings along its length) may be provided within the inlet flow path 4627 between the foam or silicone pieces 4635, e.g., to enhance sound absorption.

Figure 76:
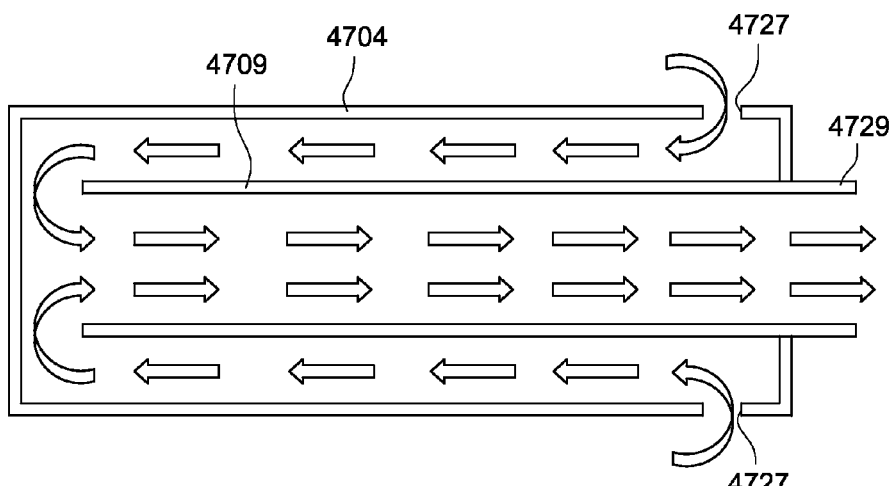
FIGS. 76 to 79 are schematic views of flow generators including air flow paths according to alternative examples of the present technology.

FIG. 76 is a schematic view of an air flow path arranged to reduce conducted noise. As illustrated, the air flow path is defined by concentric inner and outer circular tubes 4704, 4709 including an air flow inlet 4727 along the side wall of the outer tube 4704 and an air flow outlet 4729 provided by the inner tube 4709.

Figure 77:
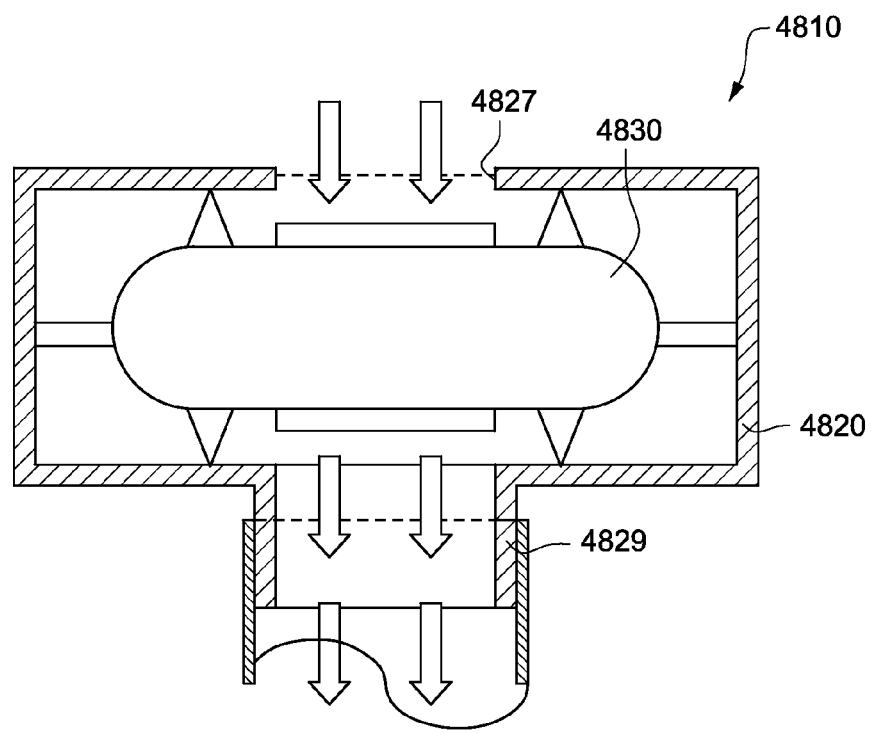

FIG. 77 is a schematic view of a flow generator 4810 including an air flow inlet 4827 and air flow outlet 4829 of the FG housing 4820 axially aligned with the blower 4830.

Figure 78:
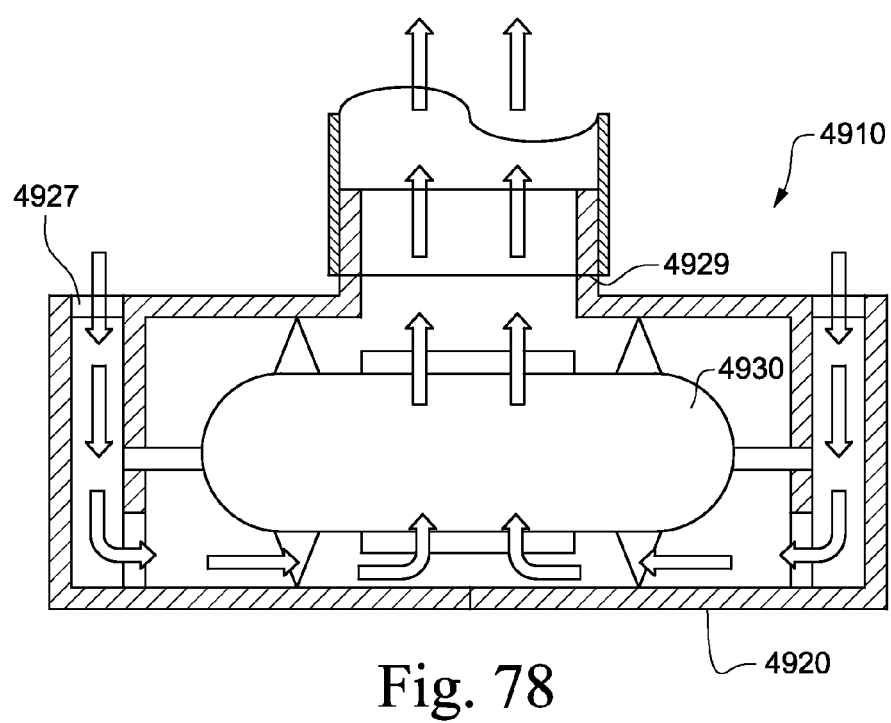

FIG. 78 is a schematic view of a flow generator 4910 including an air flow outlet 4929 of the FG housing 4920 axially aligned with the blower 4930 and an annular air flow inlet 4927 arranged concentrically outwardly from the blower 4930 such that the air flow inlet paths extend along sides of the blower 4930.

Figure 79:
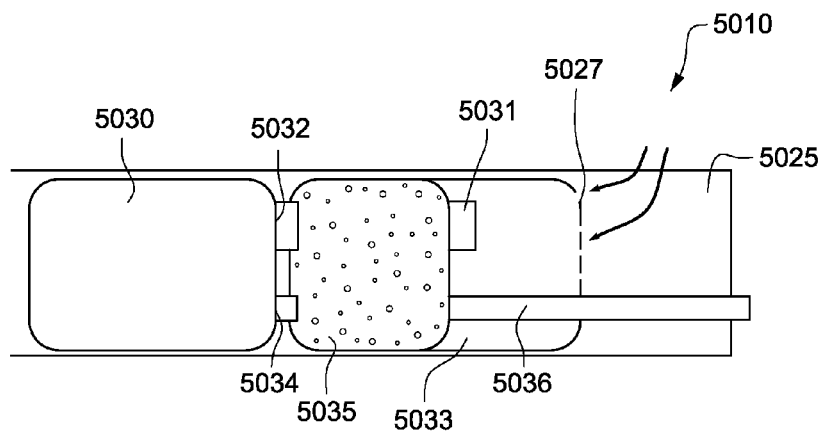

FIG. 79 is a schematic view of a flow generator 5010 including a blower 5030 and an inlet chamber 5033. The inlet chamber 5033 includes air flow inlet 5027 to allow air into the inlet chamber 5033, and an inlet tube 5031 extends from the blower inlet 5032 and at least partially into the inlet chamber 5033 for directing air into the blower inlet. An outlet tube 5036 extends from the blower outlet 5034 to outside the blower chamber 5025. Acoustic foam 5035 (e.g., silicone foam) is provided within the inlet chamber 5033, e.g., to absorb sound.

Figures 1, 80:
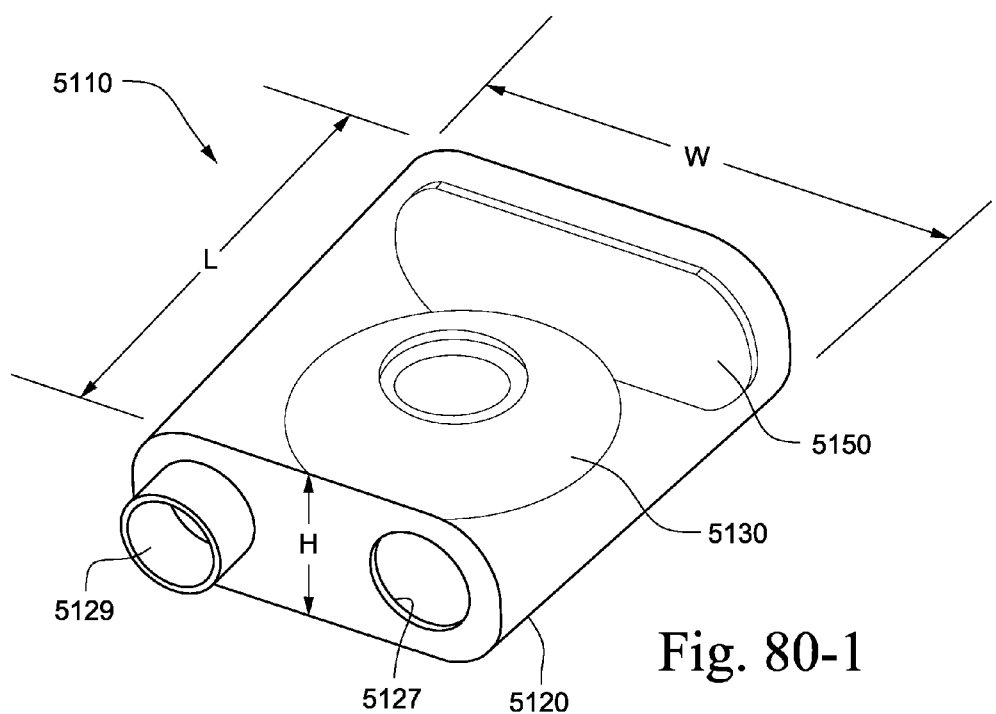
Figures 2, 80:
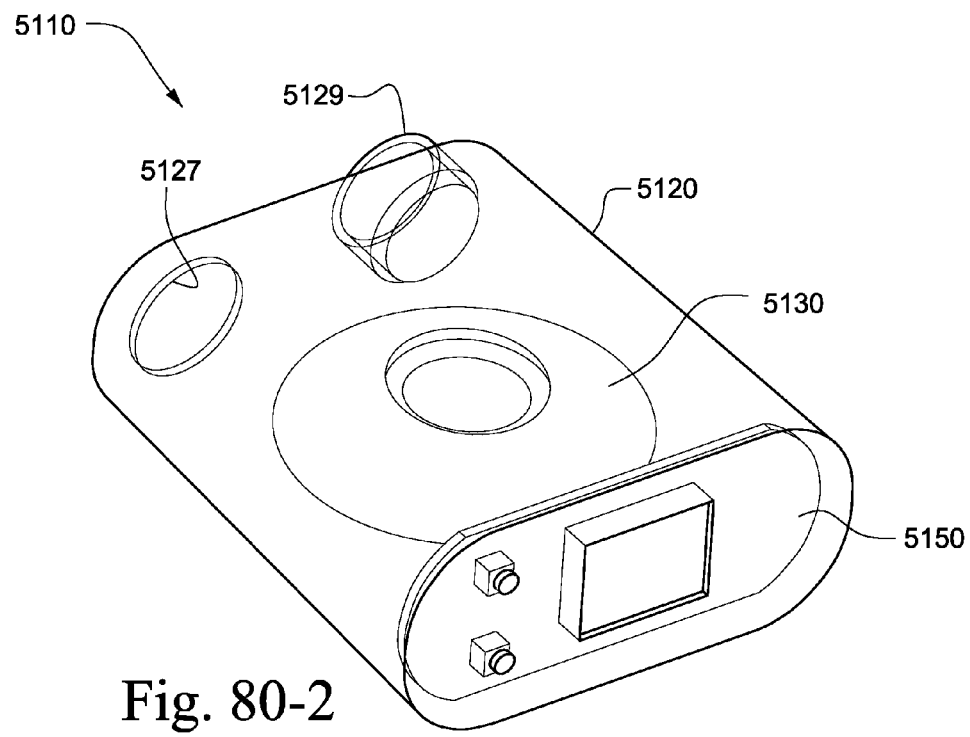
Figures 3, 80:
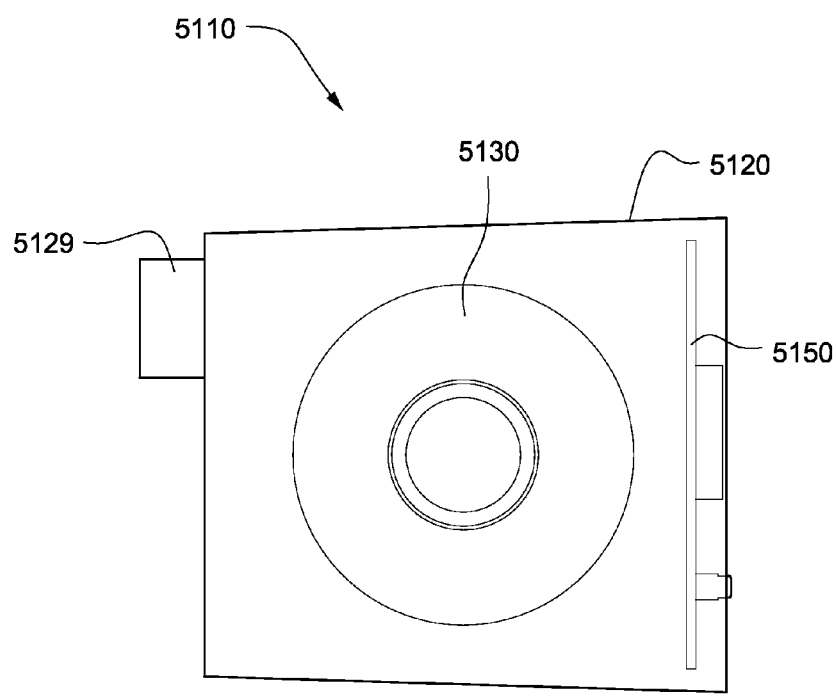
Figures 4, 80:
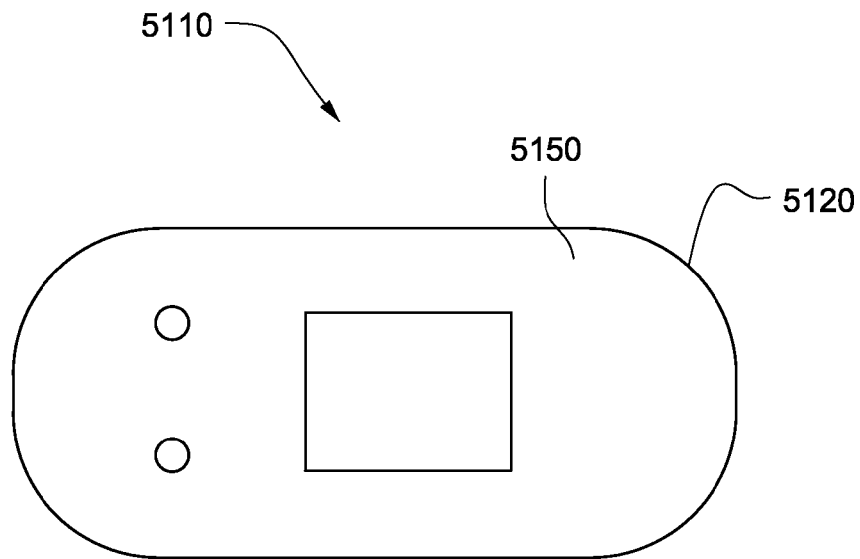
Figures 5, 80:
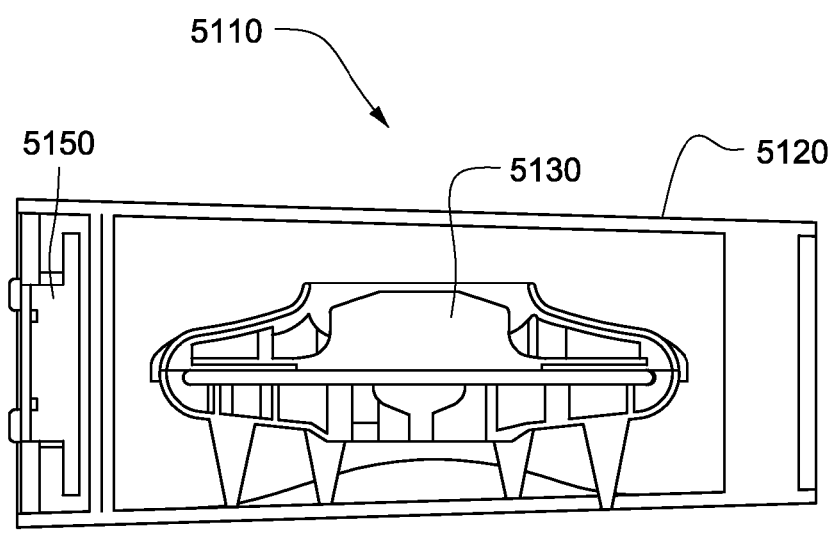

FIGS. 80-1 to 80-5 show a flow generator 5110 according to another example of the present technology. In this example, the air flow inlet 5127 and the air flow outlet 5129 are provided on the same side of the FG housing 5120. The PCB 5150 for controlling the blower 5130 is provided to a rear wall of the FG housing 5120 with the display and controls of the PCB 5150 visible along a rear side of the flow generator 5110 opposite to the side of the air flow inlet 5127 and air flow outlet 5129. In an example, as shown in FIG. 80-1, the flow generator 5110 may have a length L of about 85-105 mm (e.g., 97 mm), a width W of about 75-95 mm (e.g., 88 mm), and a height H of about 30-50 mm (e.g., 40 mm). However, it should be appreciated that other suitable dimensions are possible.

Figures 1, 81:
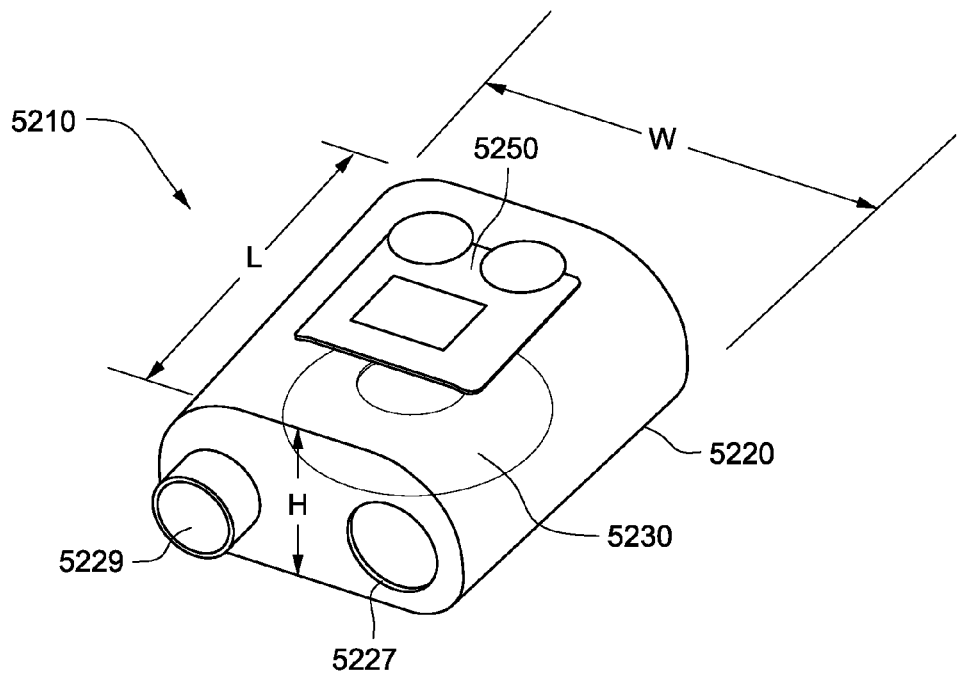
Figures 2, 81:
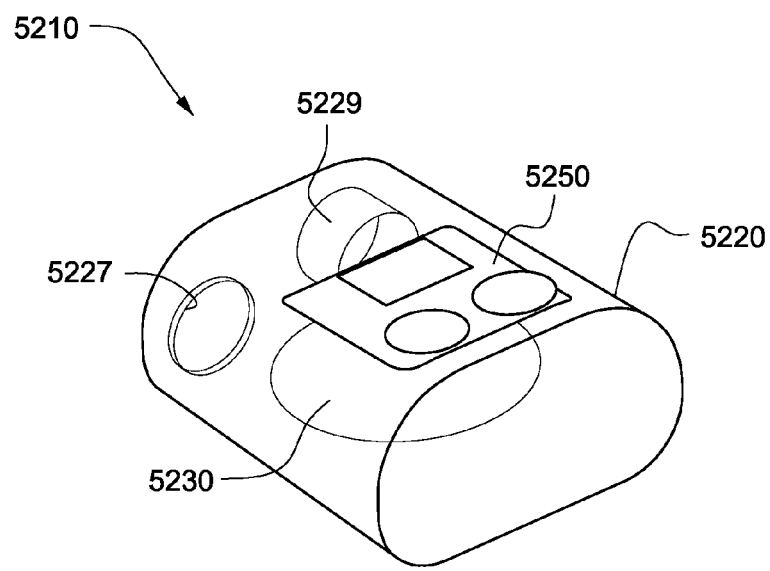
Figures 3, 81:
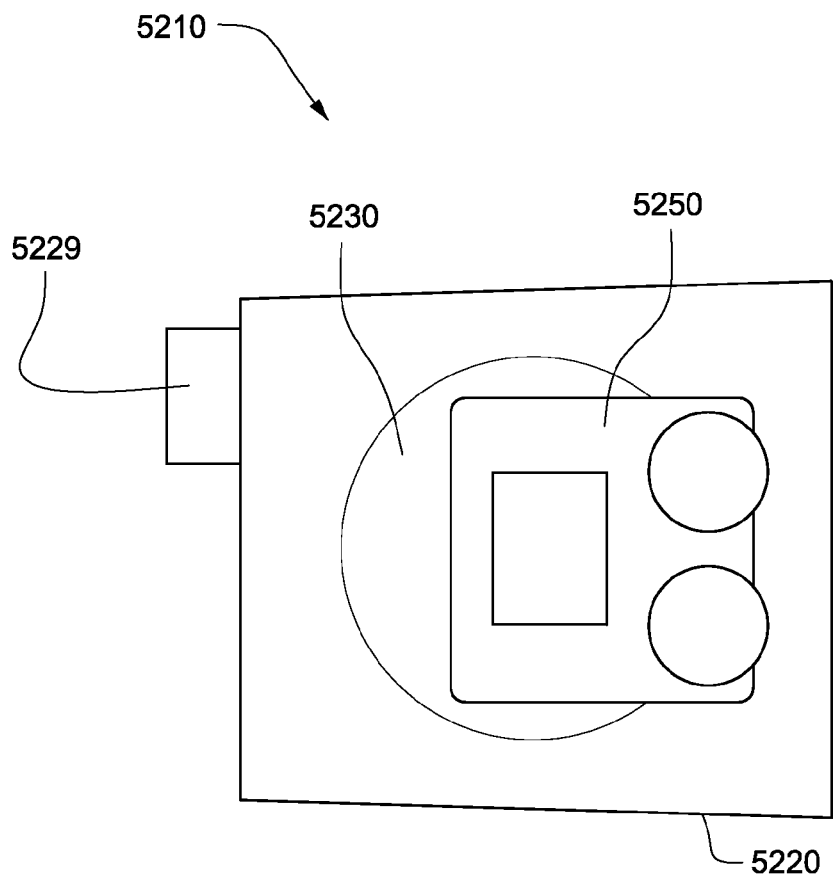
Figures 4, 81:
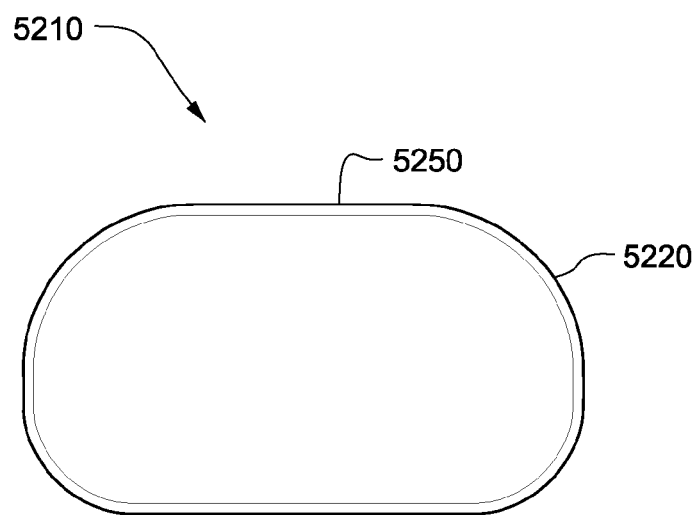
Figures 5, 81:
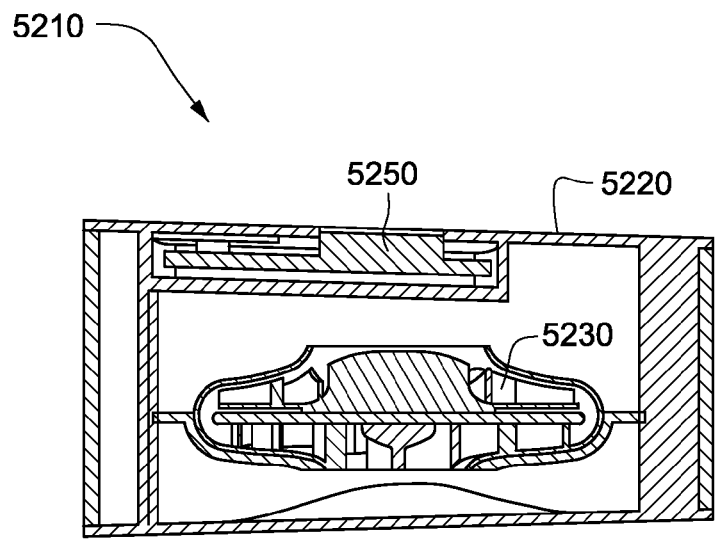

FIGS. 81-1 to 81-5 show a flow generator 5210 according to another example of the present technology. In this example, the air flow inlet 5227 and the air flow outlet 5229 are provided on the same side of the FG housing 5220. The PCB 5250 for controlling the blower 5230 is provided to a top wall of the FG housing 5220 with the display and controls of the PCB 5250 visible along a top side of the flow generator 5210. In an example, as shown in FIG. 81-1, the flow generator 5210 may have a length L of about 85-105 mm (e.g., 97 mm), a width W of about 75-95 mm (e.g., 88 mm), and a height H of about 40-60 mm (e.g., 49 mm). However, it should be appreciated that other suitable dimensions are possible.

Figures 1, 82:
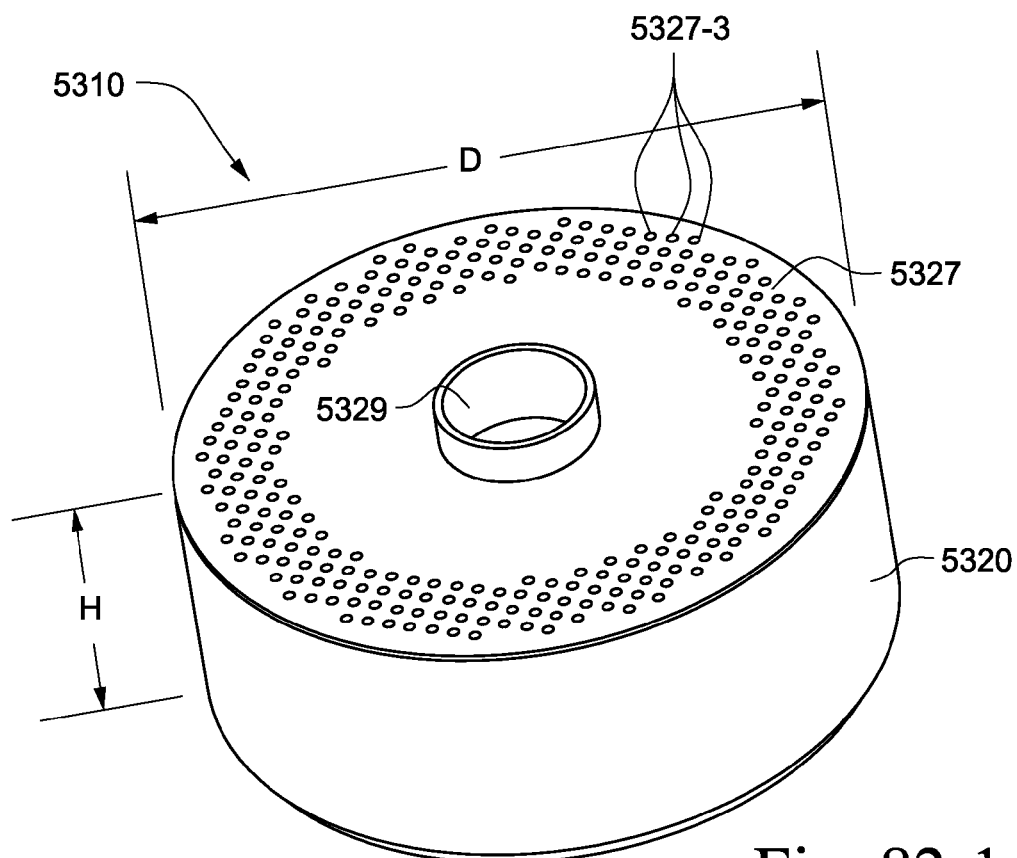
Figures 2, 82:
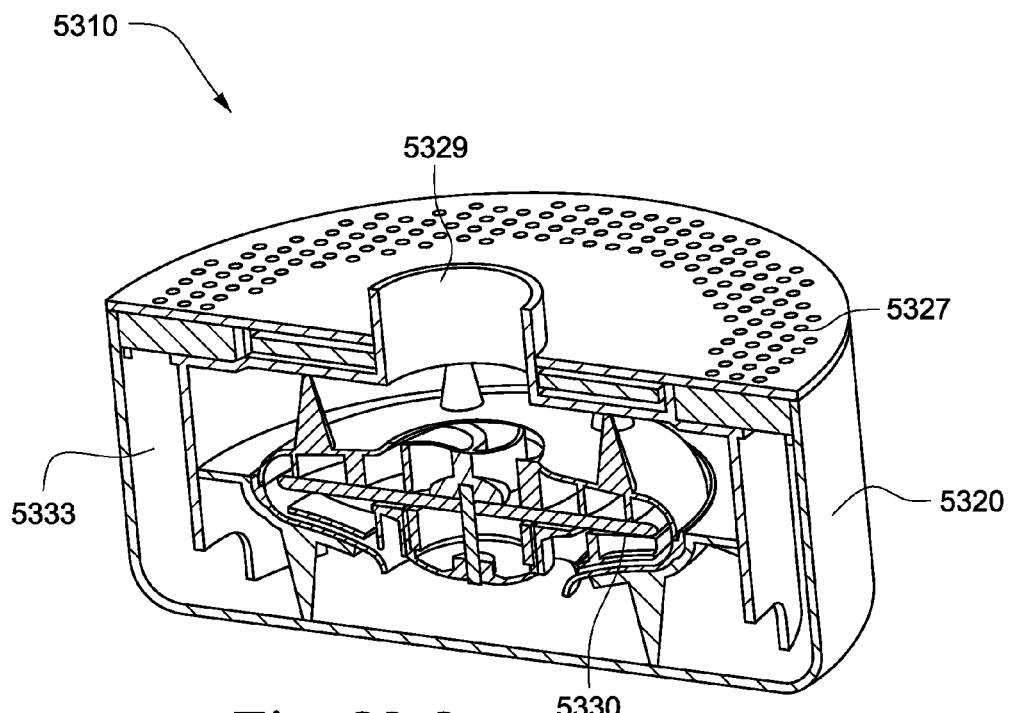
Figures 3, 82:
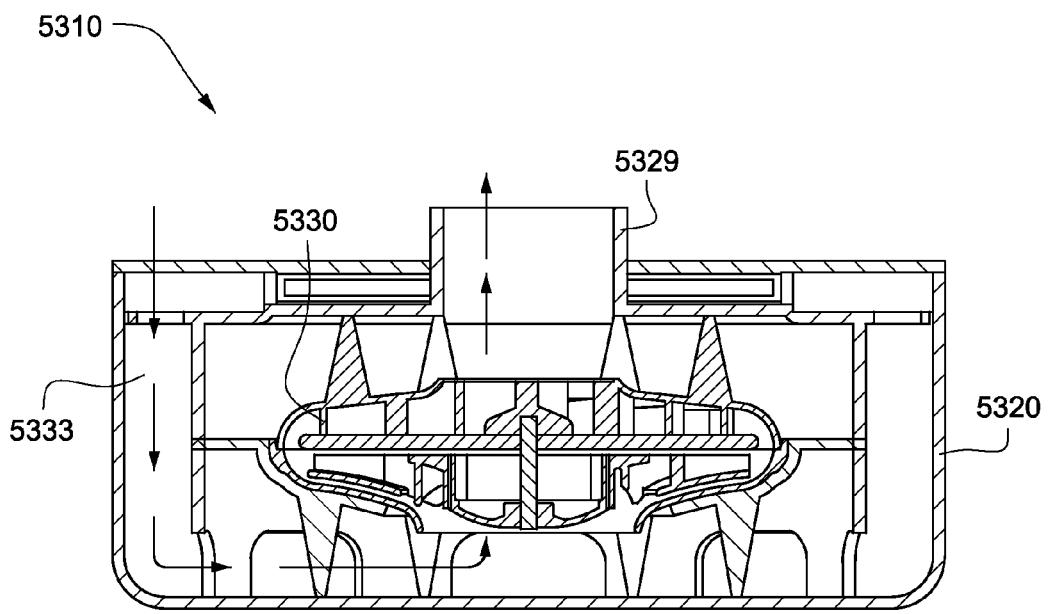

FIGS. 82-1 to 82-3 show a flow generator 5310 according to another example of the present technology. In this example, the air flow outlet 5329 of the FG housing 5320 is axially aligned with the blower 5330 and the air flow inlet 5327 includes an annular array of inlet apertures 5327-3 that are arranged concentrically outwardly from the air flow outlet 5329. The FG housing 5320 provides an annular inlet chamber 5333 that provides an inlet air flow path along sides of the blower 5330.

In an example, as shown in FIG. 82-1, the flow generator 5310 may have a diameter D of about 90-120 mm (e.g., 104 mm) and a height H of about 30-60 mm (e.g., 44 mm). However, it should be appreciated that other suitable dimensions are possible.

Figures 1, 83:
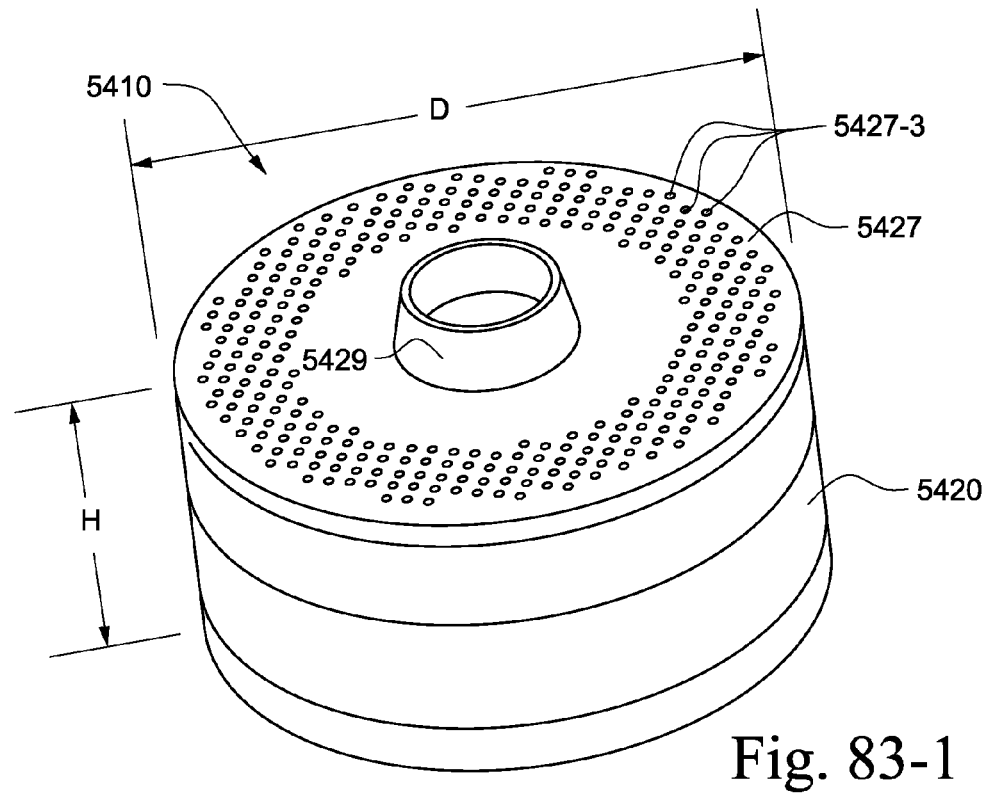
Figures 2, 83:
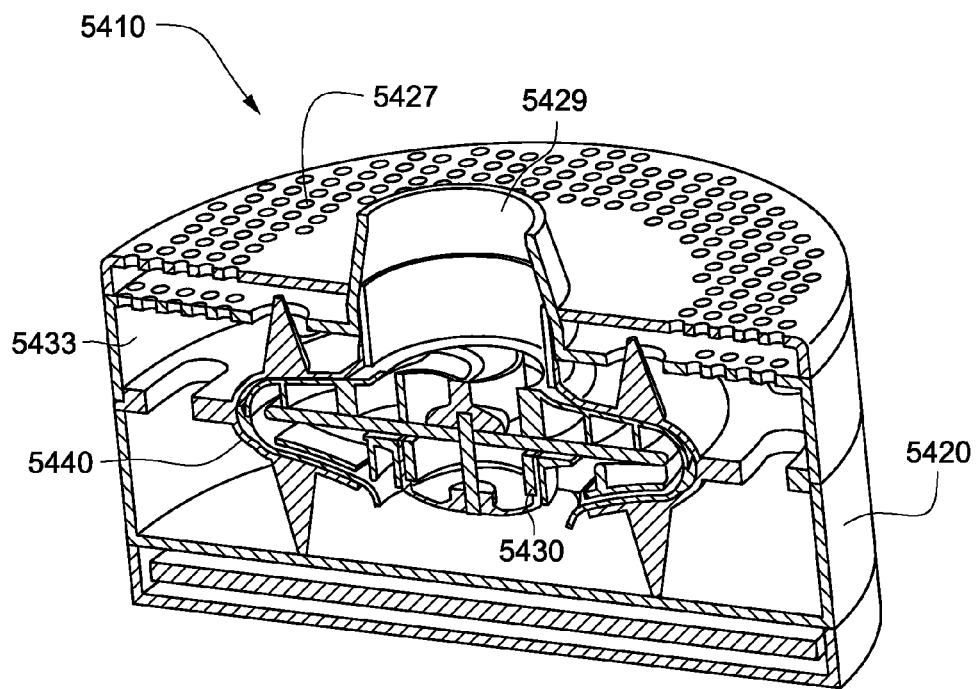
Figures 3, 83:
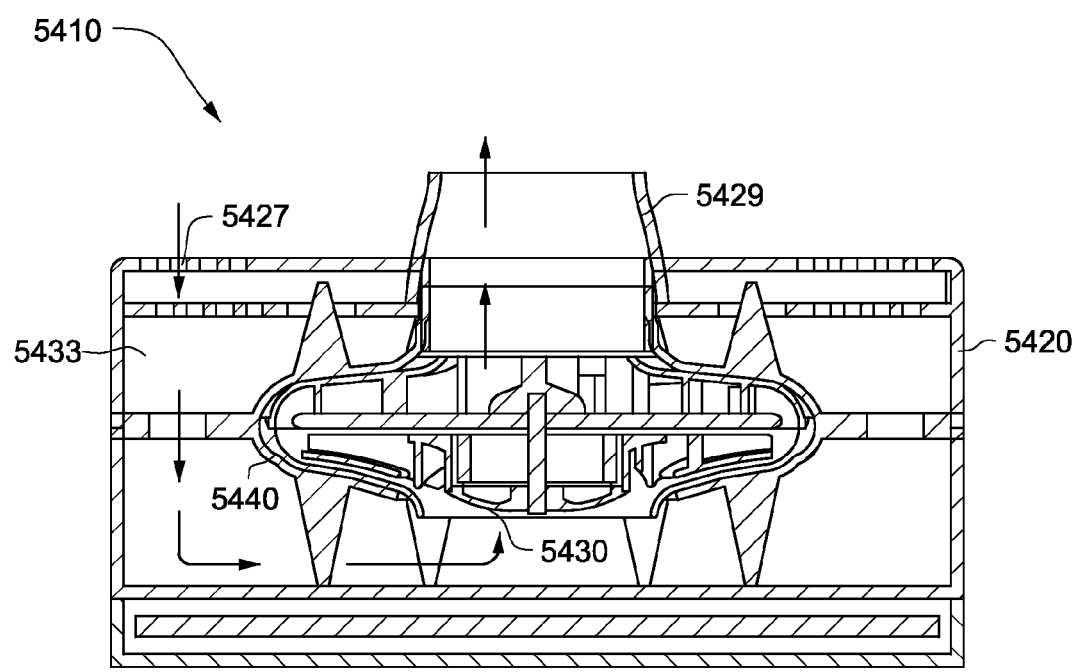

FIGS. 83-1 to 83-3 show a flow generator 5410 according to another example of the present technology. In this example, the air flow outlet 5429 of the FG housing 8420 is axially aligned with the blower 5430 and the air flow inlet 5427 includes an annular array of inlet apertures 5427-3 that are arranged concentrically outwardly from the air flow outlet 5429. The suspension device 5440 for the blower 5430 provides an annular inlet chamber 5433 that provides an inlet air flow path along sides of the blower 5430.

In an example, as shown in FIG. 83-1, the flow generator 5410 may have a diameter D of about 90-120 mm (e.g., 100 mm) and a height H of about 30-60 mm (e.g., 48 mm). However, it should be appreciated that other suitable dimensions are possible.

3. Flow Generator with Flexible Housing

Figure 28:
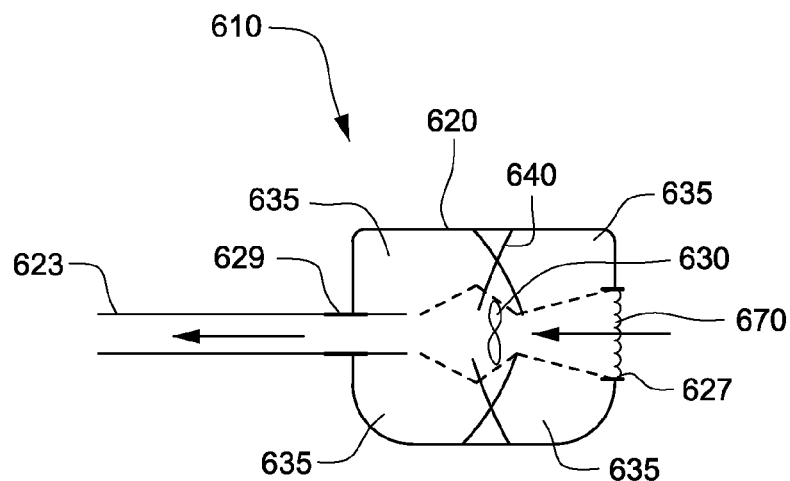
FIG. 28 is a schematic view of a flow generator according to another example of the present technology.

FIG. 28 shows a flow generator 610 according to another example of the present technology. In this example, the flow generator 610 includes a bag-like FG housing 620, e.g., flexible housing constructed of fabric, plastic, or metal wire skeleton. The blower 630 is supported within the FG housing 620 by a suspension device 640, e.g., constructed of an elastomer material. Pieces of acoustic foam or fiber 635 are also provided within the FG housing 620 to support the blower 630 and provide sound absorption and suspension. The air flow inlet 627 and the air flow outlet 629 (i.e., provided to an outlet housing 623) may be provided by perforated elastomer portions provided to the FG housing 620. An air filter 670 may be provided adjacent the air flow inlet 627.

In use, the shape of the flow generator 610 may be changed from generally cylindrical to spherical or ellipsoidal, which may shift the air flow inlet 627 and air flow outlet 629 axially. In an example, the maximum length in the longitudinal direction may be reduced on the outlet side. Also, the central axis of the blower 630 may be oriented generally perpendicular to a vertical axis of the FG housing 620 (as shown in FIG. 28), or the blower 630 may be oriented at an angle to the vertical axis.

4. Flow Generator with Alternative Chamber Design

Figure 39:
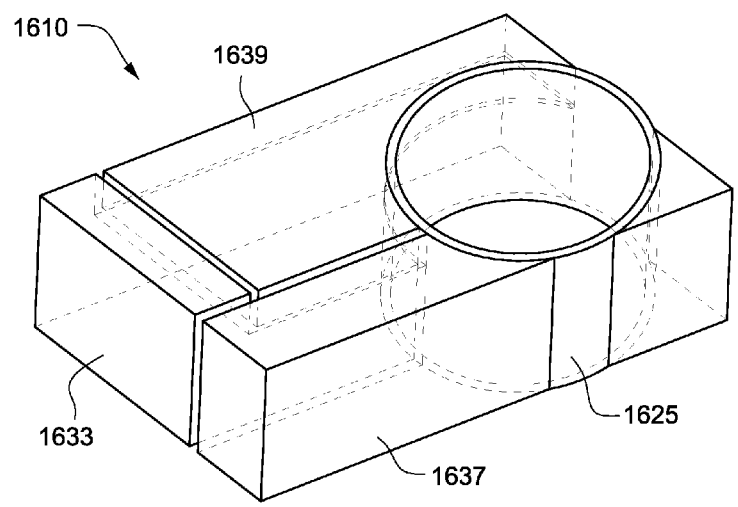
FIG. 39 shows a flow generator according to another example of the present technology.

FIG. 39 shows a flow generator 1610 according to another example of the present technology. In this example, the flow generator 1610 includes different chambers, each chamber providing a specific purpose for the air flow path. For example, the flow generator 1610 includes an air inlet chamber 1633 to direct air from the air flow inlet towards the blower inlet, a blower chamber 1625 to support the blower (not shown), an air outlet chamber 1637 to direct air from the blower outlet towards the air flow outlet, and a PCB chamber 1639 to support the PCB.

5. Microphone Support

In an example, a microphone may be provided to the PCB 50, 550, 950, 1350, 1650, 2650, 2750, 3050, 3150, 3350, 3550, 3650, 3850, 3950, 4050, 4150, 4250, 5150, 5250, 5550 to monitor the patient's breathing and noises imparted while the patient sleeps (e.g., snoring), which information may be used to determine a score or evaluation of the patient. Further details of such evaluation are disclosed in U.S. Provisional Application Nos. 61/457,273, filed Feb. 16, 2011, and 61/457,858, filed Jun. 21, 2011, each of which is incorporated herein by reference in its entirety.

Figure 53:
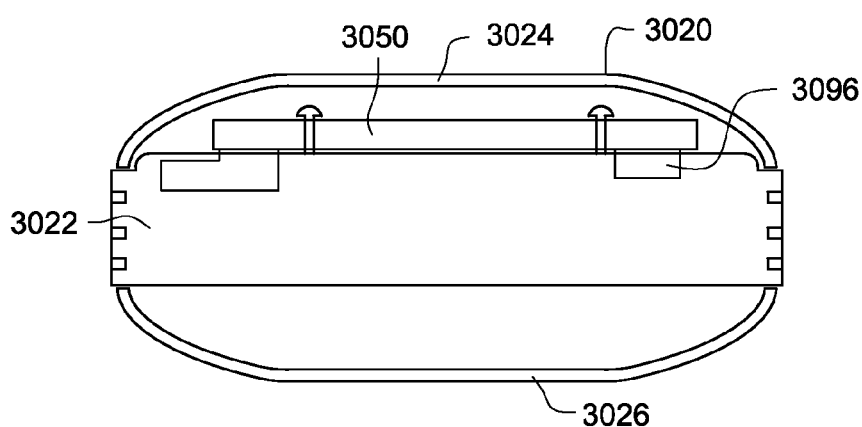
FIGS. 53 to 57 show alternative arrangements for mounting a microphone within a flow generator according to alternative examples of the present technology.

FIGS. 53 to 57 show alternative arrangements for mounting or otherwise supporting a microphone 3096 with the housing of the flow generator. For example, FIG. 53 shows a flow generator housing 3020 with top cover 3024, chassis 3022, and bottom cover 3026. The PCB 3050 supports the microphone 3096 such that is positioned in the air flow path provided by the chassis 3022.

Figure 54:
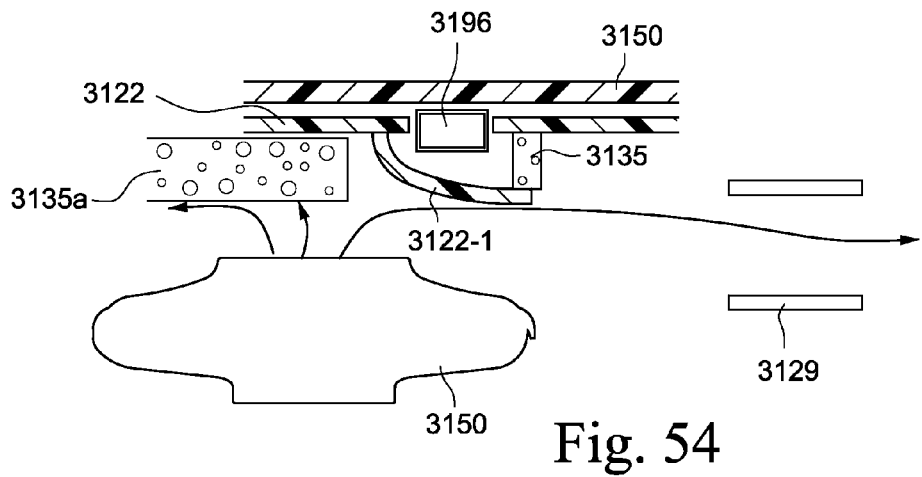

FIG. 54 shows PCB 3150 supporting microphone 3196 within the high pressure side air path. As illustrated, the microphone 3196 extends through an opening in the chassis 3122 and an arcuate wall 3122-1 extends from the chassis 3122 to protect the microphone 3196 as air flow from the blower 3150 to the air flow outlet 3129. Foam 3135 is provided within the opening defined by the arcuate chassis wall 3122-1 that communicates with the air flow path, e.g., to protect the microphone 3196 but allow monitoring by the microphone. Additional foam pieces 3135a may be provided with the chassis 3122, e.g., for sound absorption.

Figure 55:
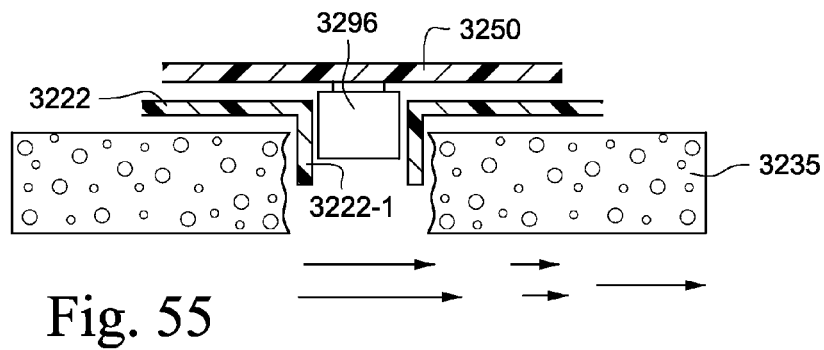

FIG. 55 shows PCB 3250 supporting microphone 3296 within the high pressure side air path. As illustrated, the microphone 3296 extends through an opening in the chassis 3222 and a chassis wall 3222-1 surrounds the opening to protect the microphone 3296. Foam 3235 may be provided along the upper wall of the chassis 3122 and around the chassis wall 3222-1, e.g., for sound absorption.

Figure 56:
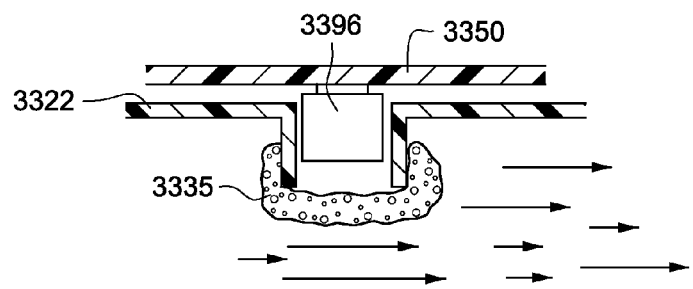

FIG. 56 shows PCB 3350 supporting microphone 3396 within the high pressure side air path. As illustrated, the microphone 3396 extends through an opening in the chassis 3322 and a chassis wall 3322-1 surrounds the opening to protect the microphone 3396. Foam 3335 covers the opening defined by the chassis wall 3322-1, e.g., to protect the microphone 3396 but allow monitoring by the microphone 3396.

Figure 57:
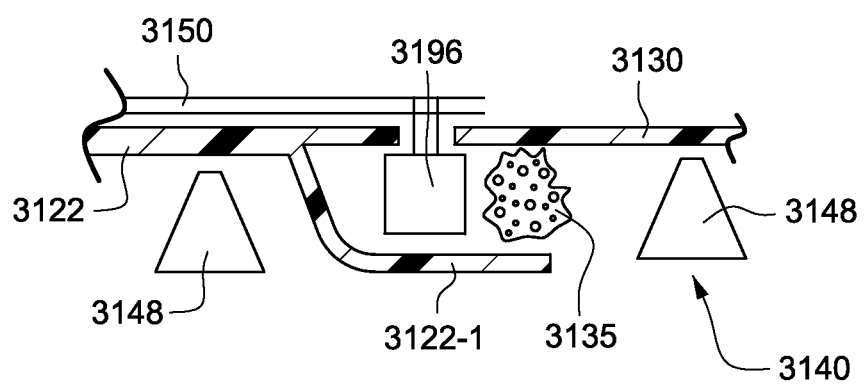

FIG. 57 shows an example similar to FIG. 54 and indicated with similar reference numerals. This example shows exemplary positioning of the microphone 3196 with respect to flexible cones 3148 of the suspension device 3140 that supports the blower 3130 as described above, i.e., no mechanical contact between microphone 3196 and blower 3130.

6. Blower Clearance

Figure 87:
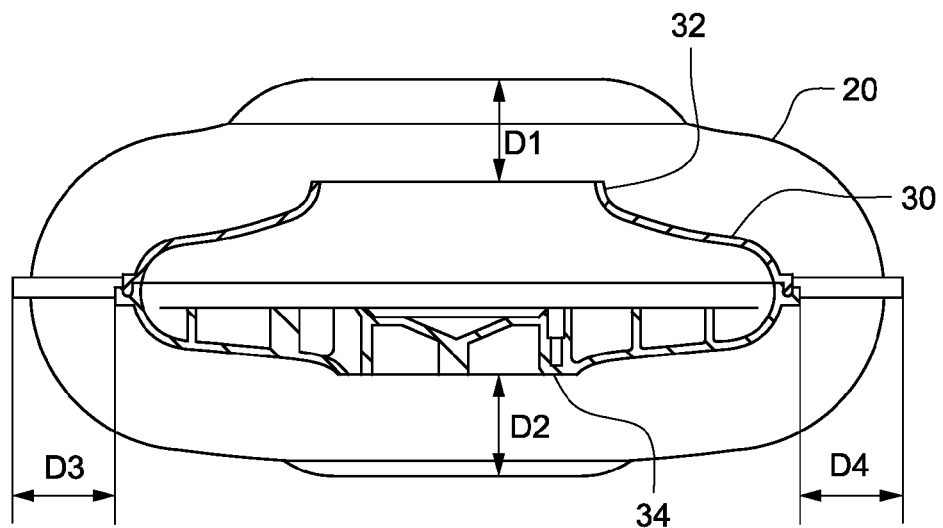
FIG. 87 is a schematic view showing clearance dimensions for a flow generator according to an example of the present technology.

In an example, the blower 30, 330, 430, 530, 630, 730, 930, 1230, 1630, 3130, 3230, 3330, 3430, 3630, 3730, 3830, 3930, 4130, 4230, 4330, 4430, 4530, 4630, 4830, 4930, 5030, 5130, 5230, 5330, 5430, 6530 is supported within the interior of the FG housing 40, 240, 640, 740, 940, 1040, 3140, 3640, 3840, 3940, 4040, 4140, 4240, 4340, 4440, 5440, 6540 such that the blower inlet 32, 332, 732, 832, 932, 1132, 1432, 1532, 1632, 1832, 1932, 2032, 2132, 2232, 2432, 3232, 5032, 6532, blower outlet 34, 334, 734, 834, 1134, 1334, 1634, 1734, 3334. 5034, 6534, and sides of the blower are sufficiently spaced from the walls the housing, e.g., for air flow, acoustics. For example, as shown in FIG. 87, the blower inlet 32 and blower outlet 34 are spaced from top and bottom walls of the FG housing 20 by distances D1, D2 or about 5-20 mm (e.g., 8 mm, 10 mm) and the sides of the blower 30 are spaced from side walls of the FG housing 20 by distances D3, D4 of about 5-20 mm (e.g., 10 mm, 12 mm). However, it should be appreciated that other suitable clearances are possible, e.g., depending on air flow paths.

Further aspects of the technology include the following:

1. A flow generator, comprising:
    a housing;
    a blower structured to generate a flow of pressurized breathable air to be provided to an air flow path; and
    a suspension device to support the blower within the housing and provide a pressure seal between low and high pressure sides of the blower,
    wherein the suspension device includes a bellows-like portion provided along a perimeter of the blower to absorb shock applied at least radially to the blower and one or more cones provided along upper and/or lower sides of the blower to absorb shock applied at least axially to the blower.
2. A flow generator according to aspect 1, wherein the suspension device is constructed of an elastomeric material.
3. A flow generator according to any one of aspects 1-2, wherein the suspension device includes an overall exterior shape that substantially matches the shape of the blower.
4. A flow generator according to any one of aspects 1-3, wherein the suspension device includes a generally cylindrical shape.
5. A flow generator according to any one of aspects 1-4, wherein the suspension device includes opposing walls that support the blower therebetween and an annular support member extending from the walls.
6. A flow generator according to aspect 5, wherein the support member includes the bellows-like portion and an end portion supported by the housing.
7. A flow generator according to any one of aspects 5-6, wherein each wall includes the one or more cones.
8. A flow generator according to any one of aspects 1-7, wherein the cones are arranged concentrically.
9. A flow generator according to any one of aspects 1-8, wherein the housing includes a blower chamber to retain the blower and suspension device within the housing.
10. A flow generator according to aspect 9, wherein the blower chamber includes at least one opening to allow air to enter the blower on the low pressure side thereof and at least one aperture to allow air to exit the blower chamber on the high pressure side thereof.
11. A flow generator according to any one of aspects 1-10, wherein the housing is structured to receive and support a PCB outside the air flow path.
12. A flow generator according to any one of aspects 1-11, wherein the housing includes an air flow inlet and air flow outlet provided on opposite sides thereof.
13. A flow generator according to aspect 12, further comprising an air filter provided to the air flow inlet.

14. A flow generator according to any one of aspects 1-13, wherein the housing includes one or more wall ribs along a perimeter of its side wall.
15. A flow generator according to any one of aspects 1-14, further comprising a PCB to control the blower, wherein the PCB is supported within the housing and includes a power lead wire for power that extends directly from the PCB to outside the housing.
16. A flow generator according to any one of aspects 1-15, further comprising a PCB to control the blower, wherein the blower includes magnet wire directly connected to the PCB.
17. A flow generator according to any one of aspects 1-16, further comprising one or more pieces of acoustic foam along the air flow path to direct air and provide sound absorption.
18. A flow generator, comprising:
   a housing including an air flow inlet and an air flow outlet; and
   a blower provided to the housing and structured to generate a flow of pressurized breathable air,
   wherein the housing includes an air flow path from the air flow inlet to the air flow outlet providing cross-sectional areas along its length of a sufficient size to prevent turbulent airflow.
19. A flow generator according to aspect 18, wherein the cross-sectional areas are of sufficient size to provide a flow rate less than 10 m/s.
20. A flow generator according to any one of aspects 18-19, wherein the cross-sectional areas are of sufficient size to provide a flow rate of about 5-6 m/s.
21. A flow generator, comprising:
   a housing including an air flow inlet and an air flow outlet; and
   a blower provided to the housing and structured to generate a flow of pressurized breathable air,
   wherein the housing includes an air flow path from the air flow inlet to the air flow outlet providing one or more reflective surfaces along its length to reduce noise.
22. A flow generator according to aspect 21, wherein the housing includes one or more air flow vanes including the reflective surfaces to provide a noise barrier for the blower and/or reflect noise from the blower so as to prevent noise emitted back through the air flow inlet.
23. A flow generator according to aspect 22, wherein the one or more air flow vanes are provided adjacent the inlet to direct incoming air flow from the inlet.
24. A flow generator, comprising:
   a housing;
   a blower structured to generate a flow of pressurized breathable air; and
   a suspension device configured to support the blower within the housing to allow operation of the flow generator in any orientation.
25. A flow generator according to aspect 24, wherein the suspension device encases the blower and clearances are provided around an inlet and an outlet of the blower.
26. A flow generator according to any one of aspects 24-25, wherein the suspension device has a substantially symmetrical shape.
27. A flow generator according to any one of aspects 24-26, wherein the suspension device further provides a pressure seal between low and high pressure sides of the blower.
28. A flow generator according to any one of aspects 24-27, wherein the suspension device includes a bellows-like portion provided along a perimeter of the blower to absorb shock applied at least radially to the blower and one or more cones provided along upper and/or lower sides of the blower to absorb shock applied at least axially to the blower.
29. A flow generator according to any one of aspects 24-27, wherein the suspension device is constructed of an elastomeric material.
30. A flow generator, comprising:
   a housing including an air flow inlet and an air flow outlet;
   a blower provided to the housing and structured to generate a flow of pressurized breathable air; and
   an air filter cartridge provided to the air flow inlet to filter air drawn into the housing by the blower, the air filter cartridge including a cartridge body and a filter media supported by the cartridge body,
   wherein the cartridge body includes structure to direct airflow away from a blower inlet of the blower.
31. A flow generator according to aspect 30, wherein the cartridge body includes a grill-like front portion or grate that defines inlet openings into the air filter cartridge.
32. A flow generator according to any one of aspects 30-31, wherein the cartridge body includes an arcuate-shaped air directing wall that provides a generally concave surface to direct air flow.
33. A flow generator according to aspect 32, wherein the air filter cartridge is provided to the air flow inlet of the housing such that the arcuate-shaped air directing wall is arranged to direct airflow away from the blower inlet of the blower.
34. A flow generator according to any one of aspects 32-33, wherein the arcuate-shaped air directing wall includes a plurality of air directing vanes that act as manifolds to reduce turbulence.
35. A flow generator according to any one of aspects 30-34, wherein the cartridge body includes an elongated ridge along one end wall adapted to interlock or otherwise engage along one side of the air flow inlet, and an elongated clip arm along the other end wall adapted to interlock or otherwise engage the other side of the air flow inlet with a snap fit.
36. A flow generator according to aspect 35, wherein the cartridge body includes a pull-tab structured to allow a user to remove the air filter cartridge from the housing.
37. A flow generator according to any one of aspects 30-36, wherein the filter media includes a thickness of about 5-15 mm.
38. A flow generator according to any one of aspects 30-37, wherein the housing includes two air flow inlets, each inlet structured to support a respective air filter cartridge.
39. A flow generator according to aspects 38, wherein the air flow inlets extend along respective corners of the housing opposite to the air flow outlet.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

| Item | Number |
|---|---|
| acoustic foam | 335, 735, 835, 935, 1135, 1435, 1735, 1835, 1935, 2035, 2135, 2235, 2435, 3135, 3235, 3335, 4235, 4435, 4535, 5035, 6535 |
| Activating features micro-switch, resistive film, capacitive sensor | 5556 |
| Additional foam pieces | 3135a |
| air delivery tube or conduit | 5 |
| air filter | 70, 670, 5870, 5970, 6070, 6170, 6570 |
| air flow inlet | 27, 327, 427, 527, 627, 727, 827, 927, 1227, 1327, 1427, 1527, 1827, 1927, 2027, 2127, 2227, 2427, 3227, 3827, 4127, 4527, 4627, 4727, 4827, 4927, 5027, 5127, 5227, 5327, 5427, 5827, 6127, 6527 |
| air flow outlet | 29, 329, 429, 729, 829, 929, 1129, 1329, 1729, 3129, 3329, 4529, 4729, 5129, 5229, 5329, 6129, 6529, 7029 |
| air flow vane | 468-1, 468-2 |
| annular foam piece | 435-1, 535-1 |
| annular inlet chamber | 5328, 5428 |
| apertures | 65-1, 1065-1, 1865-1, 2065-1 |
| bearing cartridge | 6506 |
| bearing-housing structure or diffuser | 6503 |
| blower | 30, 330, 430, 530, 630, 730, 930, 1230, 3130, 2230, 3330, 3430, 3630, 3730, 3830, 3930, 4130, 4230, 4330, 4430, 4530, 4630, 4830, 4930, 5030, 5130, 5230, 5330, 5430, 6530 |
| blower baffle walls | 569, 869, 2369, |
| blower chamber | 25, 725, 925, 1625, 4425, 5025, 6525 |
| blower housing | 6508 |
| blower inlet | 32, 332, 732, 832, 932, 1132, 1432, 1532, 1832, 1932, 2032, 2132, 2232, 2432, 3232, 5032, 6532 |
| blower lead wire | 38, 3638, 3838, 4138 |
| blower outlet | 34, 334, 734, 834, 1134, 1334, 1734, 3334, 5034, 6534 |
| blower wall member | 1221 |
| bottom air flow vanes | 88 |
| bottom dividing walls | 86 |
| bottom or second cover | 26, 3026, 6526 |
| button | 80, 2580, 2780, 2880, 2980, 6580 |
| button protrusion | 2980-2 |
| button recess | 2980-1 |
| button rim | 6580-1 |
| cartridge air directing vanes | 6577 |
| cartridge air directing wall | 6575-1 |
| cartridge body | 72, 6572, 7072 |
| cartridge end walls | 6575-2, 6575-3 |
| cartridge front portion | 6573 |
| cartridge pull-tab | 6590 |
| cartridge rear portion | 6575 |
| cartridge rib | 7079 |
| chassis or main housing | 22, 3022, 3122, 3222, 3322, 6522 |
| Chassis exterior | 62-2 |
| chassis interior | 64 |
| chassis interior | 62-1 |
| chassis wall | 3122-1, 3222-1, 3322-1 |
| clip arm | 6579 |
| clip portion | 76 |
| Concave surface | 7075-1 |
| cover protrusion | 2924-P |
| display | 52, 2652, 2752 |
| elongated ridge | 66578 |
| end walls | 7076-1, 7076-2 |
| Fastener opening | 24-1, 26-1 |
| Fastener receptacle | 69-1, 69-2 |
| filter air directing vanes | 7081 |
| filter air directing wall | 7075 |
| filter media | 74, 5974, 6074, 6174, 6574 |
| filter media body portion | 6174-2 |
| filter media ring portion | 6174-3 |
| Filter pull tab | 5974-1 |
| first air filter | 7070-1 |
| first blower chamber wall | 65, 1765, 1865, 2065, 2165 |
| First inlet | 427-1, 7027-1, |
| flexible feet, pegs or cones | 48, 3148, 3648, 4048, 4348, 6548 |
| flow generator | 10, 210, 310, 410, 510, 610, 710, 810, 910, 1010, 1110, 1210, 1310, 1410, 1510, 1610, 1710, 1810, 1910, 2010, 2110, 2210, 2310, 2410, 3210, 3310, 3410, 3510, 3610, 3710, 3810, 3910, 4210, 4310, 4410, 4510, 4610, 4810, 4910, 5010, 5110, 5210, 5310, 5410, 6510, |
| flow generator housing or FG housing | 20, 220, 320, 420, 520, 620, 720, 820, 920, 1620, 3020, 4020, 4120, 4320, 4420, 4620, 4820, 5120, 5220, 5320, 5420, 5820, 6020, 6120, 6520, 7020 |
| foam block | 435-2, 535-2 |
| gap | 81 |
| grate | 6573, 7073 |
| groove | 83 |
| hitching post | 4117 |
| horizontally extending walls | 7073 |
| housing bead | 224-B, 226-B |
| housing recess | 224-R, 226-R |
| impeller | 6501 |
| inlet air flow vanes | 68, 368, 768, 868, 968, 1568, 1868, 2068, 2368, 2468, 3768 |
| inlet apertures | 5327-3, 5427-3 |
| inlet cap | 4468 |
| inlet chamber | 33, 333, 1633, 5033, 6533 |
| inlet openings | 6573-1, 7073-1 |
| inlet tube | 5031 |
| inner concentric tube | 4709 |
| led array | 2753 |
| living hinge | 82, 2582, 2882 |
| magnet | 6502-2 |
| magnet wire | 59 |
| main chassis wall | 62 |
| microphone | 3096, 3196, 3296 |
| motor | 6502 |
| muffler | 4655 |
| opening | 85-1, 1085-1, 5385-1 |
| outer concentric tube | 4704 |
| outlet air flow vanes | 1390 |
| outlet chamber | 1637 |
| outlet housing | 623 |
| outlet tube | 5033 |
| patient interface | 7 |
| PCB chamber | 3533-1, 3833-1 |
| PCB hood or removable portion | 28 |
| pegs | 61 |
| power cord | 4016 |
| power lead wire or power cable | 60 |
| pressure seal | 3441 |
| printed circuit board (PCB) | 50, 550, 950, 1350, 2650, 2750, 3050, 3150, 3350, 3550, 3650, 3850, 3950, 4050, 4150, 4250, 5150, 5250, 5550 |
| radial bellows-like portion | 6546 |
| ridge | 6578 |
| rotor | 6507 |
| rotor cap | 6502-3 |
| sealing cover | 1308 |
| second air filter | 7070-2 |
| second blower chamber wall | 85, 1785 |
| second inlet | 427-2, 7027-2 |
| side wall | 63 |
| silicone wall | 940-1 |

| Item | Number |
| --- | --- |
| S-shaped or bellows-like support portion | 46-2 |
| Stator component | 6502-1 |
| stop structure | 24-2 |
| support end portion | 46-1 |
| support member | 46, 3946, 4046, 4346 |
| supporting microphone | 3196, 3296, 3396 |
| suspension apertures | 42-1, 44-1 |
| suspension bead | 245-1 |
| suspension exterior portion | 247 |
| suspension or support device | 40, 240, 640, 740, 940, 1040, 3140, 3640, 3840, 3940, 4040, 4140, 4240, 4340, 4440, 5440, 6540 |
| suspension recess | 245-2 |
| suspension slits | 49 |
| suspension support member | 245 |
| suspension walls | 42, 44, 242, 244 |
| switch | 54 |
| tapered surface | 2595 |
| top cover wall | 24-w |
| top dividing walls | 66 |
| top or first cover | 24, 2524, 2624, 2724, 2824, 2924, 3024, 5824, 6524 |
| wall rib | 63-1, 263-1 |
| wire guide | 67 |

What is claimed is:

1. A flow generator for generating a flow of pressurized breathable air to be delivered to a patient for respiratory therapy, the flow generator comprising:
   a housing including an air flow inlet, an air flow outlet, and an air flow path from the air flow inlet to the air flow outlet;
   a blower structured to generate the flow of pressurized breathable air to be provided to the air flow path, the blower including an inlet along an inlet side thereof and an outlet along an outlet side thereof; and
   a suspension device to support the blower within the housing and provide a pressure seal between the inlet and outlet sides of the blower,
   wherein the suspension device surrounds the blower to enclose or encase the blower, and the suspension device includes opposing suspension walls with respective suspension apertures to accommodate the inlet and the outlet of the blower,
   wherein the inlet and the outlet of the blower and respective suspension apertures of the suspension device are coaxial with one another, and
   wherein the suspension device includes a bellows portion extending radially outwardly from the opposing suspension walls and arranged along a perimeter of the blower to absorb shock applied at least radially to the blower, and the suspension device further includes one or more cones provided to each of the opposing suspension walls and arranged along respective inlet and outlet sides of the blower to absorb shock applied at least axially to the blower.

2. A flow generator according to claim 1, wherein the suspension device is constructed of an elastomeric material.

3. A flow generator according to claim 1, wherein the suspension device includes an exterior shape that corresponds to an exterior shape of the blower.

4. A flow generator according to claim 3, wherein the suspension device includes a cylindrical shape.

5. A flow generator according to claim 1, wherein the suspension device includes an annular support member extending radially outwardly from the opposing suspension walls.

6. A flow generator according to claim 5, wherein the annular support member includes the bellows portion and an end portion supported by the housing.

7. A flow generator according to claim 1, wherein said one or more cones provided to each of the opposing suspension walls comprises a plurality of said cones that are arranged in a circle.

8. A flow generator according to claim 1, wherein the housing includes a blower chamber to retain the blower and suspension device within the housing.

9. A flow generator according to claim 8, wherein the blower chamber includes at least one opening to allow air to enter the blower on the inlet side thereof and at least one aperture to allow the flow of pressurized breathable air generated by the blower to exit the blower chamber on the outlet side thereof.

10. A flow generator according claim 1, wherein the housing is structured to receive and support a printed circuit board (PCB) outside the air flow path.

11. A flow generator according to claim 1, wherein the air flow inlet and the air flow outlet of the housing are provided on opposite sides of the housing.

12. A flow generator according to claim 11, further comprising an air filter provided to the air flow inlet.

13. A flow generator according to claim 1, wherein the housing includes one or more wall ribs along a perimeter of its side wall.

14. A flow generator according to claim 1, further comprising a printed circuit board (PCB) to control the blower, wherein the PCB is supported within the housing and includes a power lead wire for power that extends directly from the PCB to outside the housing.

15. A flow generator according to claim 1, further comprising a printed circuit board (PCB) to control the blower, wherein the blower includes magnet wire directly connected to the PCB.

16. A flow generator according to claim 1, further comprising one or more pieces of acoustic foam along the air flow path to direct air and provide sound absorption.

17. A flow generator according to claim 1, wherein the air flow path provides one or more reflective surfaces along a length of the air flow path to reduce noise.

18. A flow generator according to claim 17, wherein the housing includes one or more air flow vanes including the one or more reflective surfaces to provide a noise barrier for the blower and/or to reflect noise from the blower so as to prevent noise from being emitted back through the air flow inlet.

19. A flow generator according to claim 18, wherein the one or more air flow vanes are provided adjacent the air flow inlet to direct incoming air flow from the air flow inlet.

20. A flow generator according to claim 1, wherein the suspension device is configured to support the blower within the housing to allow operation of the flow generator in any orientation.

21. A flow generator according to claim 1, wherein the suspension apertures provide clearances around the inlet and the outlet of the blower.

22. A flow generator according to claim 1, wherein the one or more cones are structured and arranged to extend outwardly from respective suspension walls in a direction away from the blower.

23. A flow generator according to claim 1, wherein the bellows portion includes one or more folds structured and arranged to allow the bellows portion to expand and contract to absorb shock.

24. A flow generator according to claim 1, wherein the air flow outlet is adapted to connect to an air delivery tube for delivery of the flow of pressurized breathable air to a patient interface.

25. A flow generator according to claim 1, further comprising an air filter provided to the air flow inlet of the housing to filter air drawn into the housing by the blower.

26. A flow generator according to claim 1, wherein the blower includes a rotor and an impeller provided to the rotor, and wherein the inlet and the outlet of the blower and respective suspension apertures of the suspension device each include a central axis that is coaxial with an axis of the rotor.

27. A flow generator according to claim 1, wherein the suspension device is configured to allow movement of the blower with respect to the housing in use and prevent contact of the blower with the housing in any orientation of the flow generator.

* * * * *